(12) United States Patent
Lim et al.

(10) Patent No.: US 9,365,590 B2
(45) Date of Patent: Jun. 14, 2016

(54) SELENOPHENE-FUSED AROMATIC COMPOUND AND MANUFACTURING METHOD THEREOF

(71) Applicants: Industry-Academia Cooperation Group of Sejong University, Seoul (KR); Samsung Life Public Welfare Foundation, Seoul (KR)

(72) Inventors: Dongyeol Lim, Seoul (KR); Do-Hyun Nam, Seoul (KR); Rashmi Dubey, Bilaspur (IN); Hangeun Lee, Seoul (KR)

(73) Assignees: Industry-Academia Cooperation Group of Sejong University, Seoul (KR); Samsung Life Public Welfare Foundation, Seoul (KR)

(*) Notice: Subject to any disclaimer, the term of this patent is extended or adjusted under 35 U.S.C. 154(b) by 0 days.

(21) Appl. No.: 14/228,493

(22) Filed: Mar. 28, 2014

(65) Prior Publication Data

US 2014/0213790 A1    Jul. 31, 2014

Related U.S. Application Data

(63) Continuation of application No. PCT/KR2012/007905, filed on Sep. 28, 2012.

(30) Foreign Application Priority Data

Sep. 28, 2011  (KR) .................. 10-2011-0098603
Dec. 7, 2011   (KR) .................. 10-2011-0130059

(51) Int. Cl.
| | | |
|---|---|---|
| *C07D 471/02* | (2006.01) | |
| *C07D 517/04* | (2006.01) | |
| *C07D 345/00* | (2006.01) | |
| *C07D 421/06* | (2006.01) | |

(52) U.S. Cl.
CPC ............ *C07D 517/04* (2013.01); *C07D 345/00* (2013.01); *C07D 421/06* (2013.01)

(58) Field of Classification Search
None
See application file for complete search history.

(56) References Cited

U.S. PATENT DOCUMENTS

2010/0272678 A1* 10/2010 Gokaraju et al. ............ 424/85.2

FOREIGN PATENT DOCUMENTS

| KR | 10-2009-0033909 | 4/2009 |
|---|---|---|
| WO | 9732850 | 9/1997 |
| WO | 2004101767 | 11/2004 |
| WO | WO 2006/084338 A1 | 8/2006 |
| WO | WO 2007/087684 A1 | 8/2007 |

OTHER PUBLICATIONS

CAPLUS 2008 1535792.*
CAPLUS 2011:743895.*
CAPLUS 1934 22660.*
CAPLUS 1982:198943.*
CAPLUS 1971:53380.*
CAPLUS 1972:405279.*
Int'l. Search Report issued in Int'l. App. No. PCT/KR2012/007905, mailed Mar. 15, 2013.
Staples et al.; "Tandem free-radical addition/substitution chemistry and its application to the preparation of novel AT$_1$ receptor antagonists"; Organic & Biomolecular Chemistry, 2011 (first published on the web; Nov. 3, 2010); vol. 9, No. 2, pp. 473-479, ISSN 1477-0520.
Arsenyan et al.; "Syntehsis, structure and cytotoxicity of 3-C,N,S,Se substituted benzo[b] selenophene derivatives"; European Journal of Medicinal Chemistry, 2011 (available online: May 13, 2011), vol. 46, No. 8, pp. 3434-3443, ISSN 0223-5234.
Baiwir et al., "NMR Studies of the Chalcogen Analogues of Benzofuran. IV-Proton, Carbon-13 and Selenium-77 Magnetic Resonance in Nitrobenzo[b]selenop henes", Organic Magnetic Resonance, vol. 18, No. 1, Jan. 1. 1982.
Baiwir et al.. "Selenium-77 Nuclear Magnetic Resonance in Mono- and Disubstituted Benzo[b]selenophenes", Organic Magnetic Resonance, vol. 16, No. 1. Jan. 1, 1981.
Murphy, "Product class7: benzo[b]selenophenes", Science of Synthesis, vol. 10. Jan. 1, 2000.
Croisy et al., "Spectrometrie de Masse D'heterocycles Selenies. III-Etude de la Fragmentation de Quelques Selenolo[2, 3-b] Pyridines", Organic Mass Spectrometry, vol. 9, No. 10. Oct. 1, 1974, Abstract Only.
Dari et al., "Synthesis of Selenopsilocine (3-dimethylaminoethyl-4-hydroxybenzo[b]selenophene)", Heterocycles, vol. 34, No. 9, 1992.
Chinese Intellectual Property Office, Office Action, Dated Nov. 17, 2015 (Submitted with Translation).

* cited by examiner

*Primary Examiner* — Heidi Reese
(74) *Attorney, Agent, or Firm* — Greer, Burns & Crain, Ltd.

(57) ABSTRACT

The present disclosure relates to a method for more easily and economically producing a selenophene-fused aromatic compound derivative containing various substituents and the selenophene-fused aromatic compound produced according to the method, and the selenophene-fused aromatic compound can be used for various purposes such as an intermediate of an anti-bacterial or anticancer substance, an indicator of which color is changed depending on a solvent, or a fluorescent substance.

17 Claims, 4 Drawing Sheets

SELENOPHENE-FUSED AROMATIC COMPOUND AND MANUFACTURING METHOD THEREOF

CROSS-REFERENCE TO RELATED APPLICATION

This application is a continuation of International Application No. PCT/KR2012/007905 filed on Sep. 28, 2012, claiming the priority based on Korean Patent Application No. 10-2011-0098803 filed on Sep. 28, 2011 and Korean Patent Application No. 10-2011-0130059 filed on Dec. 7, 2011, the contents of all of which are incorporated herein by reference in their entirety.

TECHNICAL FIELD

The embodiments described herein pertain generally to a selenophene-fused aromatic compound, and a producing method of the selenophene-fused aromatic compound.

BACKGROUND

"Benzoselenophene" as a kind of compound containing selenium (Se) at an aromatic ring is a substance having a similar structure to that of indole, benzothiophene, and benzofuran. A "selenophene-fused aromatic compound" herein refers to benzoselenophene, pyridoselenophene, thiazoloselenophene, furanoselenophene, and the like. That is, the benzoselenophene is a substance included in the "selenophene-fused aromatic compound". The selenophene-fused aromatic compound including the benzoselenophene is a highly applicable material in various fields. However, according to a conventional technology, it is not easy to synthesize derivatives thereof. Thus, it has been difficult to use the selenophene-fused aromatic compound as an intermediate or a material of drugs or as a material having a semiconducting property.

A lot of synthesis methods of indole or benzothiophene structurally similar to the benzoselenophene have already been developed, and the indole and benzothiophene have reached commercialization as medicines for various diseases, such as anticancer drugs, hormone replacement drugs, immunomodulators, diet pills, anti-diabetic drugs, and the like. The benzoselenophene is expected to be highly effective in preventing cancer due to the similarity in structure with the indole or benzothiophene and availability thereof as a photochemotherapeutic agent used for treating achromoderma or psoriasis has been highly valued. However, it has not reached commercialization due to lack of development of a synthesis method.

Some methods for synthesizing derivatives of the selenophene-fused aromatic compound including the benzoselenophene have been known. By way of example, they are disclosed in "Substituted benzodithiophenes and benzodiselenophenes (Korean Patent Laid-open Publication No. 10-2009-0033909), etc. However, if benzodithiophene derivatives are synthesized by using the conventionally known methods, the benzodithiophene derivatives can be synthesized through multiple reactions. In particular, as for a derivative containing a substituent at an aromatic site of benzoselenophene, a kind of derivative which can be synthesized is very limited.

DISCLOSURE OF THE INVENTION

Problems to be Solved by the Invention

In view of the foregoing problems, example embodiments provide a method for more easily and economically producing a selenophene-fused aromatic compound derivative containing various substituents.

Further, the example embodiments provide the selenophene-fused aromatic compound produced according to the example embodiments, and the selenophene-fused aromatic compound can be used for various purposes such as an intermediate of an anti-bacterial or anticancer substance, an indicator of which color is changed depending on a solvent, or a fluorescent substance.

However, problems to be solved by the present disclosure are not limited to the above-described problems. Although not described herein, other problems to be solved by the present disclosure can be clearly understood by those skilled in the art from the following descriptions.

Means for Solving the Problems

A first aspect of example embodiments provides a selenophene-fused aromatic compound represented by the following Chemical Formula 1:

[Chemical Formula 1]

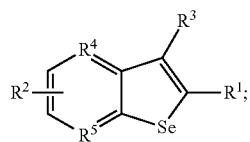

wherein in the formula, $R^1$ represents —$CO_2H$, —$CO_2R$, 4-$NO_2$-Ph, 4-CN-Ph, 4-$RO_2$C-Ph, 4-X-Ph, or the following Chemical Formula A:

[Chemical Formula A]

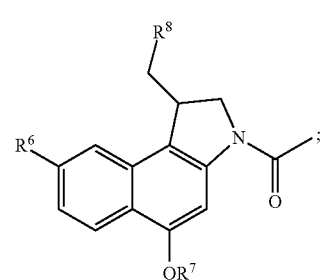

$R^2$ represents H, —$NO_2$, —NHCOR, $CX_3$, —OR, -diOR, a substitutable alkyl group, a substitutable alkoxy group, a substitutable alkylene-dioxy group, a substitutable amino group, a halo group, or a substituent represented by the following Chemical Formula B:

[Chemical Formula B]

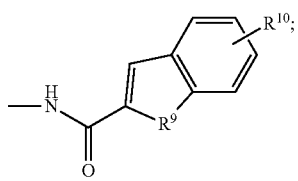

X represents a halo group, $R^3$ represents —H, —OH, —$NH_2$, a substitutable alkyl group, or a substitutable aryl group, each of $R^4$ and $R^5$ independently represents a substitutable N, O, S, C, bond or a non-bonding, $R^6$ represents H, or a substitutable alkoxy group, $R^7$ represents H, —$CONR^{17}R^{20}$, or

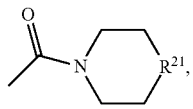

each of $R^{17}$ and $R^{29}$ independently represents H, or a substitutable alkyl group, $R^{21}$ represents C, O, N, or S, $R^8$ represents a halo group, $R^9$ represents O, NH, S, or Se, $R^{10}$ represents a substitutable alkyl group, a substitutable alkoxy group, a halo group, —$NO_2$, or —NHCOR, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

A second aspect of the example embodiments provides a producing method of a selenophene-fused aromatic compound represented by the following Chemical Formula 2, the method including:

preparing a reaction mixture containing a diselenide compound represented by a general formula of $R^{11}$—$CH_2$—Se—Se—$CH_2$—$R^{11}$, a solvent, and a reducing agent; and adding an aromatic starting material represented by the following Chemical Formula 2a and a base to the reaction mixture to be reacted:

[Chemical Formula 2a]

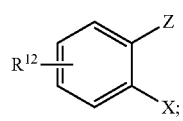

[Chemical Formula 2]

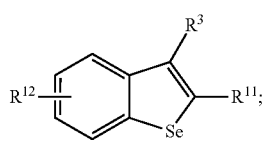

wherein in the formulas,

Z represents —$COR^{15}$, or —CN, $R^{15}$ represents —H, a substitutable alkyl group, a substitutable aryl group, or a substitutable alkoxy group, $R^3$ represents —H, —OH, —$NH_2$, a substitutable alkyl group, or a substitutable aryl group, $R^{11}$ represents —$CO_2H$, —$CO_2R$, 4-$NO_2$-Ph, 4-CN-Ph, 4-$RO_2C$-Ph, or 4-X-Ph, $R^{12}$ represents H, —$NO_2$, —NHCOR, $CX_3$, —OR, -diOR, a substitutable alkoxy group, a substitutable alkylenedioxy group, a substitutable amino group, or a halo group, X represents a halo group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

A third aspect of the example embodiments provides a producing method of a selenophene-fused aromatic compound represented by the following Chemical Formula 7, the method including:

reacting an aromatic starting material represented by the following Chemical Formula 7a and $R^{11}CH_2X$ via heating to form a reaction intermediate represented by the following Chemical Formula 7b; and adding a solvent and a base to the reaction intermediate to be reacted:

[Chemical Formula 7a]

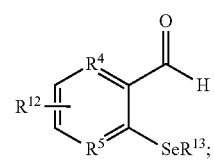

[Chemical Formula 7b]

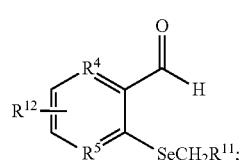

[Chemical Formula 7]

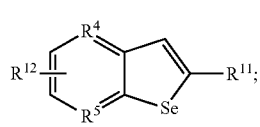

wherein in the formulas, each of $R^4$ and $R^5$ independently represents a substitutable N, O, S, C, bond or a non-bonding, $R^{11}$ represents —$CO_2H$, —$CO_2R$, 4-$NO_2$-Ph, 4-CN-Ph, 4-$RO_2C$-Ph, or 4-X-Ph, $R^{12}$ represents H, —$NO_2$, —NHCOR, $CX_3$, —OR, -diOR, a substitutable alkoxy group, a substitutable alkylenedioxy group, a substitutable amino group, or a halo group, X represents a halo group, $R^{13}$ represents a substitutable alkyl group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

A fourth aspect of the example embodiments provides a producing method of a selenophene-fused aromatic compound represented by the following Chemical Formula 10, the method including:

reacting a MCBI (7-methoxy-1,2,9,9a-tetrahydrocyclopropa[c]benz[e]indol-4-one) compound represented by the following Chemical Formula 10a and a selenium-containing aromatic compound represented by the following Chemical Formula 10b:

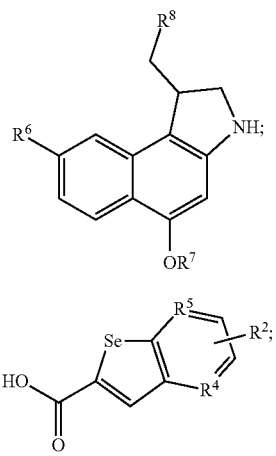
[Chemical Formula 10a]

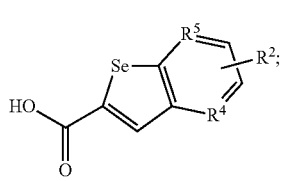
[Chemical Formula 10b]

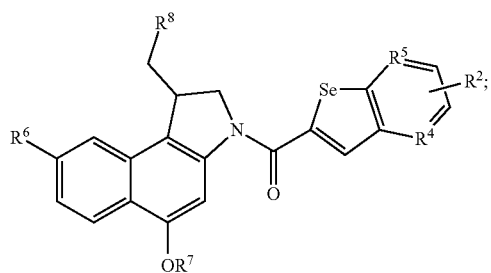
[Chemical Formula 10]

wherein in the formulas,
$R^2$ represents a substitutable alkyl group, a substitutable alkoxy group, a halo group, —$NO_2$, —NHCOR, or a substituent represented by the following Chemical Formula B, each of $R^4$ and $R^5$ independently represents a substitutable C, O, N, S, bond or a non-bonding, $R^6$ represents H, or a substitutable alkoxy group, $R^7$ represents H, —$CONR^{17}R^{20}$, or

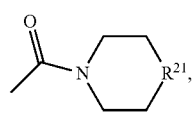

each of $R^{17}$ and $R^{20}$ independently represents H, or a substitutable alkyl group, $R^{21}$ represents C, O, N, or S, $R^8$ represents a halo group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative:

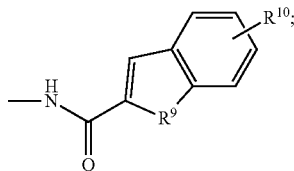
[Chemical Formula B]

wherein in the formula,
$R^9$ represents O, NH, S, or Se,
$R^{10}$ represents a substitutable alkyl group, a substitutable alkoxy group, a halo group, —$NO_2$, or —NHCOR, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

A fifth aspect of the example embodiments provides a producing method of a selenophene-fused aromatic compound represented by the following Chemical Formula 11, the method including:

reacting a MCBI compound represented by the following Chemical Formula 11a and a
selenium-containing aromatic compound represented by the following Chemical Formula 11b:

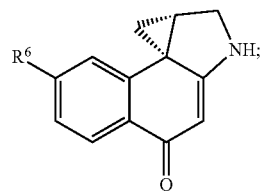
[Chemical Formula 11a]

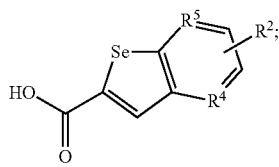
[Chemical Formula 11b]

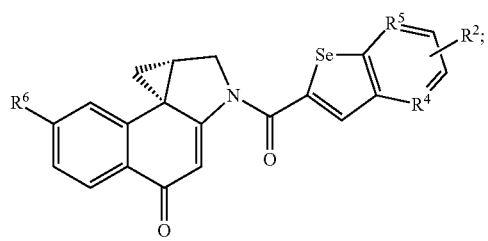
[Chemical Formula 11]

wherein in the formulas,
$R^2$ represents a substitutable alkyl group, a substitutable alkoxy group, a halo group, —$NO_2$, —NHCOR, or a substituent represented by the following Chemical Formula B, each of $R^4$ and $R^5$ independently represents a substitutable C, O, N, S, bond or a non-bonding, $R^6$ represents H, or a substitutable alkoxy group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative:

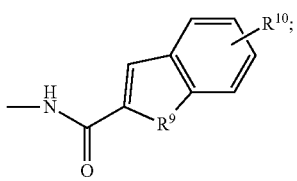

[Chemical Formula B]

wherein in the formula, $R^9$ represents O, NH, S, or Se, $R^{10}$ represents a substitutable alkyl group, a substitutable alkoxy group, a halo group, —$NO_2$, or —NHCOR, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

A sixth aspect of the example embodiments provides an anti-bacterial composition including
a selenophene-fused aromatic compound according to the first aspect of the example embodiments.

A seventh aspect of the example embodiments provides an indicator composition including
a selenophene-fused aromatic compound according to the first aspect of the example embodiments,
wherein the indicator composition may be used as an indicator of which color is changed
depending on a solvent.

An eighth aspect of the example embodiments provides a fluorescent composition including
a selenophene-fused aromatic compound according to the first aspect of the example embodiments.

A ninth aspect of the example embodiments provides an anticancer composition including a
selenophene-fused aromatic compound according to the first aspect of the example embodiments.

Effect of the Invention

In accordance with the example embodiments, it is possible to more easily and economically produce a benzoselenophene derivative containing various substituents. Further, since it is possible to easily and economically produce a selenophene-fused aromatic compound according to the example embodiments, the possibility of commercialization of the selenophene-fused aromatic compound as an anti-bacterial composition, an anticancer drug, and the like can be increased.

Meanwhile, by appropriately selecting a diselenide compound, a solvent, a reducing agent, and a base as materials required for producing the selenophene-fused aromatic compound, the selenophene-fused aromatic compound can be obtained at a high yield. Further, by diversifying kinds of aromatic starting materials for producing the selenophene-fused aromatic compound, kinds of the obtained selenophene-fused aromatic compound can also be diversified.

The selenophene-fused aromatic compound produced in accordance with to the example embodiments may have various useful properties depending on a specific chemical formula. By way of example, a selenophene-fused aromatic compound having an anti-bacterial property can be synthesized, and in this case, it can be used as a medical material. Further, a selenophene-fused aromatic compound having a property that causes a change in color formation depending on a solvent can be synthesized, and in this case, it can be used as an indicator. Furthermore, some selenophene-fused aromatic compounds may have a fluorescent property, and in this case, they can be used as an intermediate for synthesizing organic semiconductors by using the fluorescent property. Moreover, the selenophene-fused aromatic compound can be usefully used as an anticancer drug or a precursor thereof. The selenophene-fused aromatic compound may exhibit an anticancer effect through DNA alkylation. It is confirmed that as a result of cytotoxicity tests carried out to various cancer cells, the selenophene-fused aromatic compound has an $IC_{50}$ value in nM or pM exhibits a potent anticancer effect. Further, the selenophene-fused aromatic compound can be applied to various cancers such as breast cancer, central nervous system cancer, colorectal cancer, non-small cell lung cancer, renal cancer, prostate cancer, ovarian cancer, etc., and, thus, the selenophene-fused aromatic compound in accordance with the example embodiments is expected to be usefully used as an anticancer drug for various cancers.

BEST MODE FOR CARRYING OUT THE INVENTION

Figure 1:
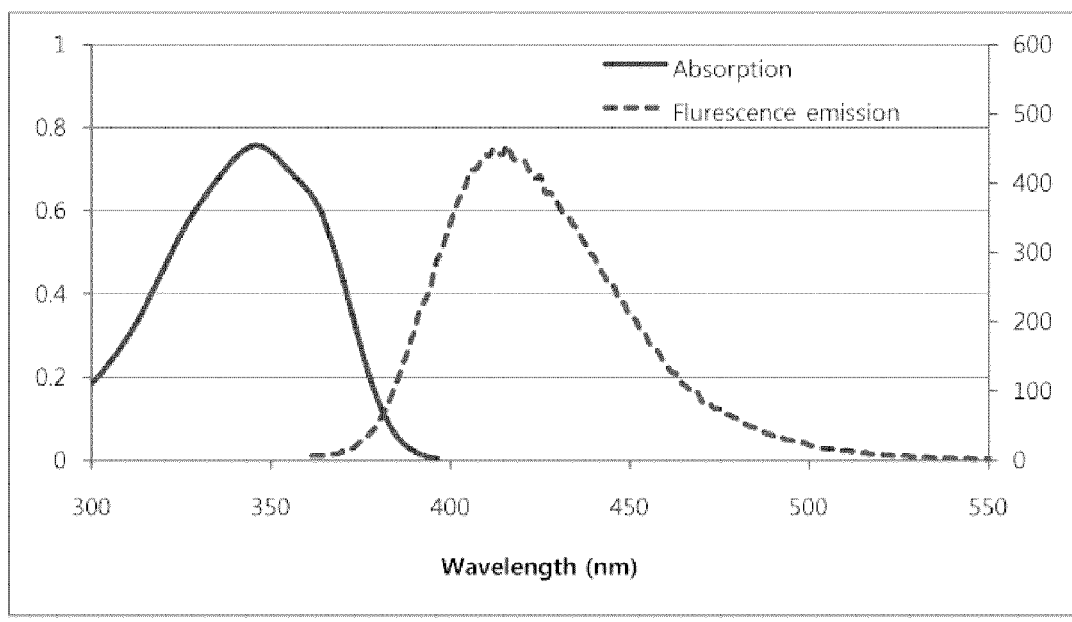
FIG. 1 is spectra showing a fluorescent property of a selenophene-fused aromatic compound produced according to Entry 26 of Example.

Hereinafter, example embodiments of the present disclosure will be described in detail with reference to the accompanying drawings so that the present disclosure may be readily implemented by those skilled in the art. However, it is to be noted that the present disclosure is not limited to the example embodiments but can be embodied in various other ways. In drawings, parts irrelevant to the description are omitted for the simplicity of explanation, and like reference numerals denote like parts through the whole document.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

The term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "on" that is used to designate a position of one element with respect to another element includes both a case that the one element is adjacent to the another element and a case that any other element exists between these two elements.

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, the term "halo" or "halo group" refers to, but not limited to F, Cl, Br, or I.

Through the whole document, the term "alkyl" or "alkyl group" refers to a linear or branched saturated or unsaturated alkyl group having 1 to 10, 1 to 7, or 1 to 5 carbon atoms, and may include, for example, but not limited to, methyl, ethyl, propyl, butyl, pentyl, hexyl, heptyl, octyl, nonyl, decyl, or isomers thereof. When the alkyl group is substituted, it may be substituted with four or less substituents as listed below at any binding point (any carbon atom). The alkyl group may be substituted with one or more substances of a hydroxyl group, carboxylate, oxo, halogen (for example, F, Cl, Br, I), haloalkyl (for example, $CCl_3$ or $CF_3$), alkyloxycarbonyl (—C(O)R), alkylcarbonyloxy (—OCOR), carbamoyl (—NHCOOR— or —OCONHR—), urea (—NHCONHR—), thiol, cyano, nitro, amino, acylamino, $C_1$-$C_6$ alkylthio, arylthio, $C_1$-$C_6$ alkyl, $C_1$-$C_6$ alkoxy, aryloxy, alkylcarbonyloxy, arylcarbonyloxy, $C_3$-$C_6$ cycloalkyl, $C_3$-$C_6$ cycloalkyloxy, $C_2$-$C_6$ alkenyl, $C_3$-$C_6$ alkynyl, aryl, amino carbonyl, $C_1$-$C_6$ alkyl carbonyl, $C_3$-$C_6$ cycloalkyl carbonyl, heterocyclyl carbonyl, aryl carbonyl, aryloxy carbonyl, $C_1$-$C_6$ alkoxy carbonyl, $C_3$-$C_6$ cycloalkyloxy carbonyl, heterocyclyloxy carbonyl, $C_1$-$C_6$ alkylsulfonyl, arylsulfonyl, a heterocyclyl group, etc. Meanwhile, when the alkyl group is substituted with another alkyl group, this is used to refer to "branched alkyl group". Desirably, the alkyl group contains 1 to 6 carbon atoms. An alkylene used herein refers to a cross-linked alkyl group having a chemical formula $(CH_2)_n$. By way of example, the alkylene may include $CH_2$, —$CH_2CH_2$—, —$CH_2CH_2CH_2$—, etc.

The term "aryl" or "aryl group" used herein alone or as part of another group includes a monocyclic or bicyclic aromatic ring, for example, phenyl and substituted phenyl and a fused group, for example, naphthyl, phenanthrenyl, indenyl, tetrahydronaphthyl, indanyl, and the like. By way of example, the "aryl" or "aryl group" may contain at least one ring having 6 or more atoms and may contain 5 or less rings having 22 or less atoms, and double bonds may exist alternately (resonantly) between adjacent carbon atoms or appropriate hetero atoms. The "aryl" or "aryl group" may be optionally substituted with one or more groups including, but not limited to, halogen, for example, F, Br, Cl, or I, alkyl, for example, methyl, ethyl, propyl, and alkoxy, for example, methoxy or ethoxy, hydroxy, carboxy, carbamoyl, alkyloxy carbonyl, nitro, alkenyloxy, trifluoromethyl, amino, cycloalkyl, aryl, heteroaryl, cyano, alkyl $S(O)_m$ (m=0, 1, 2), or thiol. By way of example, the "aryl" or "aryl group" may be phenyl, substituted phenyl as described above, phenyl, naphthyl, or substituted naphthyl as described above, but may not be limited thereto.

Through the whole document, the term "alkoxy" or "alkoxy group" may include, but is not limited to, an alkoxy group in which the above-defined "alkyl group" is bonded to an oxygen atom. The alkoxy group is bonded to a main chain, aryl, or heteroaryl group through an oxygen bridge. The alkoxy group may be a straight chained or branched although the straight-chain is preferred. Examples of the alkoxy group may include methoxy, ethyloxy, propoxy, butyloxy, t-butyloxy, i-propoxy, and the like. Desirably, the alkoxy group may contain 1 to 6 carbon atoms, and especially desirably, the alkoxy group may contain 1 to 3 carbon atoms.

Through the whole document, the term "alkylene-dioxy group" may include an alkylene group between two oxygen atoms. The "alkylene group" may be an alkylene group having 1 to 10, 1 to 7, or 1 to 5 carbon atoms, and may include, for example, but not limited to, methylene, ethylene, propylene, butylene, pentylene, hexylene, heptylene, octylene, nonylene, decylene, or isomers thereof.

The term "amine group" or "amino group" used herein alone or as part of another group refers to —$NH_2$. Further, the "amine group" or "amino group" may be optionally substituted with 1 or 2 substituents, which may be identical with or different from each other, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl, or carboxyl.

Through the whole document, the term "amino acid group" means an amino acid including α-amino acid, β-amino acid, and γ-amino acid. The amino acid may be a L-isomer or a D-isomer although the L-isomer is preferred. Examples of the amino acid may include, but may not be limited to, glycine, alanine, valine, leucine, isoleucine, methionine, proline, phenylalanine, tryptophan, serine, threonine, cysteine, thirosine, asparagine, glutamine, aspartic acid, glutamic acid, lysine, arginine, histidine, β-alanine, and ornithine. The term "peptide group" means a group generated through a reaction between lots of natural and/or non-natural amino acids.

Through the whole document, the term "carbohydrate" or "carbohydrate derivative" may be, for example, polyhydroxy aldehyde, polyhydroxy ketone, or polyol, or may be an organic group derived therefrom, and means a compound which can be changed into such a group through a simple chemical modification such as hydrolysis, oxidation, or reduction. Such a group may include, for example, but not limited to, sugar, starch, cellulose, and gum.

Through the whole document, the term "diOR" may include

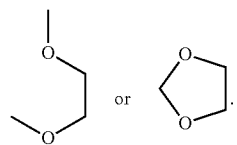

Through the whole document, the term "substitution" is intended to include all permissible substituents of organic compounds. The allowable substituents may include acyclic or cyclic, branched or unbranched, carbocyclic or heterocyclic, aromatic or nonaromatic substituents of organic compounds, and the permissible substituents may be one or more. The term "substituted" ", when in association with any of the foregoing groups, refers to a group substituted at one or more positions with substituents such as acyl, amino (including simple amino, mono and dialkylamino, mono and diarylamino, and alkylarylamino), acylamino (including carbamoyl, and ureido), alkylcarbonyloxy, aryl, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl, and the like, but may not be limited thereto. Any of the above-described substituents can be further substituted if permissible, for example, if the group contains an alkyl group, an aryl group, or other, but may not be limited thereto.

A first aspect of example embodiments provides a selenophene-fused aromatic compound represented by the following Chemical Formula 1:

[Chemical Formula 1]

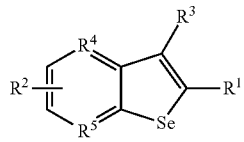

In the formula, $R^1$ represents —$CO_2H$, —$CO_2R$, 4-$NO_2$-Ph, 4-CN-Ph, 4-$RO_2C$-Ph, 4-X-Ph, or the following Chemical Formula A:

[Chemical Formula A]

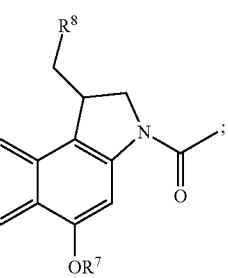

$R^2$ represents H, —$NO_2$, —NHCOR, $CX_3$, —OR, -diOR, a substitutable alkyl group, a substitutable alkoxy group, a substitutable alkylene-dioxy group, a substitutable amino group, a halo group, or a substituent represented by the following Chemical Formula B:

[Chemical Formula B]

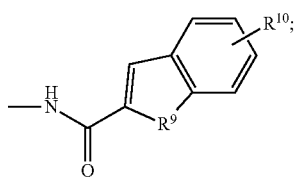

X represents a halo group, $R^3$ represents —H, —OH, —$NH_2$, a substitutable alkyl group, or a substitutable aryl group, each of $R^4$ and $R^5$ independently represents a substitutable N, O, S, C, bond or a non-bonding, $R^6$ represents H, or a substitutable alkoxy group, $R^7$ represents H, —$CONR^{17}R^{20}$, or

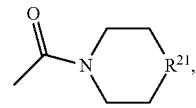

each of $R^{17}$ and $R^{29}$ independently represents H, or a substitutable alkyl group, $R^{21}$ represents C, O, N, or S, $R^8$ represents a halo group, $R^9$ represents O, NH, S, or Se, $R^{10}$ represents a substitutable alkyl group, a substitutable alkoxy group, a halo group, —$NO_2$, or —NHCOR, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

In accordance with an example embodiment, Chemical Formula 1 may be selected from, but not limited to, the following Chemical Formula 2 to Chemical Formula 6:

[Chemical Formula 2]

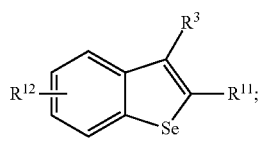

[Chemical Formula 3]

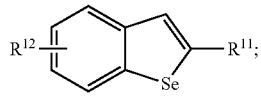

[Chemical Formula 4]

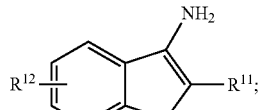

[Chemical Formula 5]

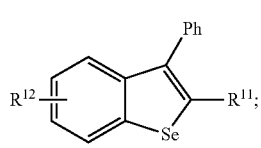

[Chemical Formula 6]

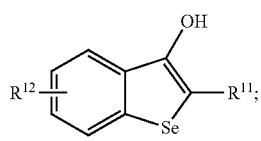

In the formulas, $R^3$ is the same as defined above in Chemical Formula 1, $R^{11}$ represents —$CO_2H$, —$CO_2R$, 4-$NO_2$-Ph, 4-CN-Ph, 4-$RO_2C$-Ph, or 4-X-Ph, $R^{12}$ represents H, —$NO_2$, —NHCOR, $CX_3$, —OR, -diOR, a substitutable alkoxy group, a substitutable alkylene-dioxy group, a substitutable amino group, or a halo group, X represents a halo group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

group, a substitutable $C_{1-7}$ alkoxy group, or a residue of a substitutable carbohydrate or carbohydrate derivative.

In accordance with an example embodiment, Chemical Formula 1 may be selected from, but not limited to, the following Chemical Formula 10 to Chemical Formula 12:

[Chemical Formula 10]

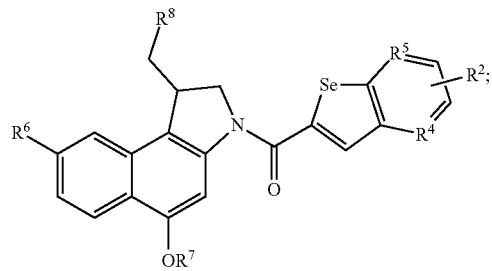

[Chemical Formula 11]

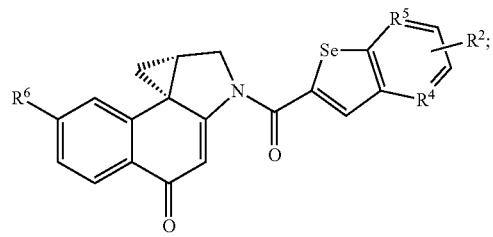

[Chemical Formula 12]

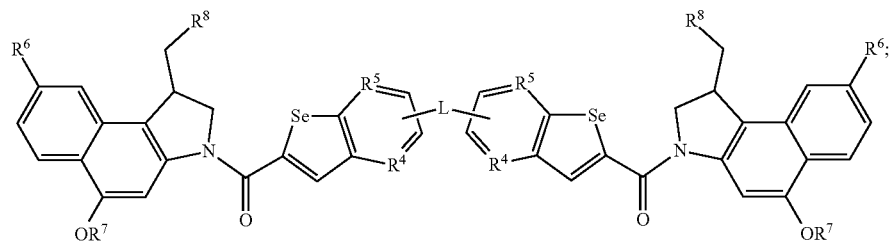

In accordance with an example embodiment, Chemical Formula 1 may be selected from, but not limited to, the following Chemical Formula 7 to Chemical Formula 9:

[Chemical Formula 7]

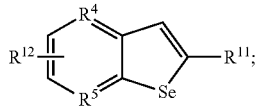

[Chemical Formula 8]

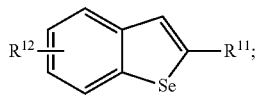

[Chemical Formula 9]

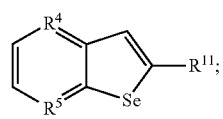

In the formulas,
each of $R^4$ and $R^5$ independently represents a substitutable N, O, S, C, bond or a non-bonding, $R^{11}$ represents —$CO_2H$, —$CO_2R$, 4-$NO_2$-Ph, 4-CN-Ph, 4-$RO_2C$-Ph, or 4-X-Ph, $R^{12}$ represents H, —$NO_2$, —NHCOR, $CX_3$, —OR, -diOR, a substitutable alkoxy group, a substitutable alkylene-dioxy group, a substitutable amino group, or a halo group, X represents a halo group, and R represents H, a substitutable alkyl group, a substitutable aryl group, a substitutable amino group, a substitutable amino acid group, a substitutable peptide In the formulas,
$R^2$ represents H, —$NO_2$, —NHCOR, $CX_3$, —OR, -diOR, a substitutable alkyl group, a substitutable
alkoxy group, a substitutable alkylene-dioxy group, a substitutable amino group, a halo group, or a substituent represented by the following Chemical Formula B:

[Chemical Formula B]

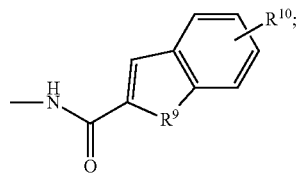

each of $R^4$ and $R^5$ independently represents a substitutable C, O, N, S, bond or a non-bonding, $R^6$ represents H, or a substitutable alkoxy group, $R^7$ represents H, —$CONR^{17}R^{20}$, or

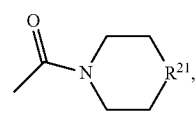

each of $R^{17}$ and $R^{29}$ independently represents H, or a substitutable alkyl group, $R^{21}$ represents C, O, N, or S, $R^8$ represents a halo group, $R^9$ represents O, NH, S, or Se, $R^{10}$ represents a substitutable alkyl group, a substitutable alkoxy group, a halo group, —$NO_2$, or —NHCOR, L represents a linker, X represents a halo group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

In accordance with an example embodiment, the linker includes —NHCO—$R^{19}$—CONH—, and in Chemical Formulas above, $R^{19}$ may be a $C_{1-7}$ alkyl group, but may not be limited thereto. By way of example, the linker may be —NHCO—$CH_2$—CONH—, —NHCO—$CH_2CH_2$—CONH—, —NHCO—$CH_2CH_2CH_2$—CONH—, —NHCO—$CH_2CH_2CH_2CH_2$—CONH—, —NHCO—$CH_2CH_2CH_2CH_2CH_2$—CONH—, —NHCO—$CH_2CH_2CH_2CH_2CH_2CH_2$—CONH—, or —NHCO—$CH_2CH_2CH_2CH_2CH_2CH_2CH_2$—CONH—, but may not be limited thereto.

By way of example, the selenophene-fused aromatic compound represented by Chemical Formula 12 above may be produced by, but not limited to, linking the two symmetric selenophene-fused aromatic compounds represented by Chemical Formula 10 above by the linker.

A second aspect of example embodiments provides a producing method of a selenophene-fused aromatic compound represented by the following Chemical Formula 2, the method including: preparing a reaction mixture containing a diselenide compound represented by a general formula $R^{11}$—$CH_2$—Se—Se—$CH_2$—$R^{11}$, a solvent, and a reducing agent; and adding an aromatic starting material represented by the following Chemical Formula 2a and a base to the reaction mixture to be reacted:

[Chemical Formula 2a]

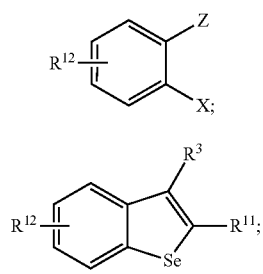

[Chemical Formula 2]

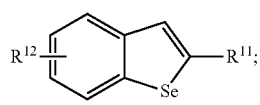

In the formulas,

Z represents —$COR^{15}$, or —CN, $R^{15}$ represents —H, a substitutable alkyl group, a substitutable aryl group, or a substitutable alkoxy group, $R^3$ represents —H, —OH, —$NH_2$, a substitutable alkyl group, or a substitutable aryl group, $R^{11}$ represents —$CO_2H$, —$CO_2R$, 4-$NO_2$-Ph, 4-CN-Ph, 4-$RO_2C$-Ph, or 4-X-Ph, $R^{12}$ represents H, —$NO_2$, —NHCOR, $CX_3$, —OR, -diOR, a substitutable alkoxy group, a substitutable alkylene-dioxy group, a substitutable amino group, or a halo group, X represents a halo group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

In accordance with an example embodiment, Chemical Formula 2a may include, but may not be limited to, the following Chemical Formula 3a, and Chemical Formula 2 may include, but may not be limited to, the following Chemical Formula 3:

[Chemical Formula 3a]

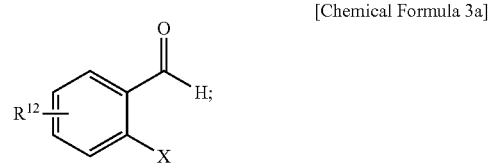

[Chemical Formula 3]

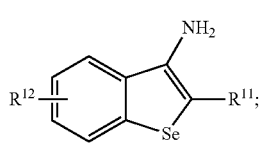

In the formulas,

X, $R^{11}$, and $R^{12}$ are the same as defined above in Chemical Formulas 2a and 2.

In accordance with an example embodiment, Chemical Formula 2a may include, but may not be limited to, the following Chemical Formula 4a, and Chemical Formula 2 may include, but may not be limited to, the following Chemical Formula 4:

[Chemical Formula 4a]

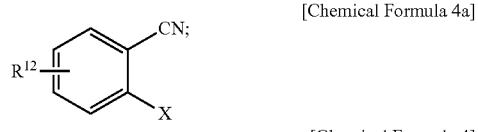

[Chemical Formula 4]

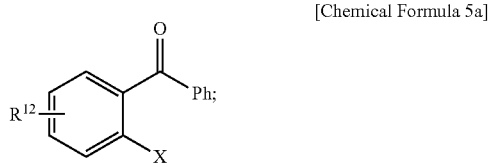

In the formulas,

X, $R^{11}$, and $R^{12}$ are the same as defined above in Chemical Formulas 2a and 2.

In accordance with an example embodiment, Chemical Formula 2a may include, but may not be limited to, the following Chemical Formula 5a, and Chemical Formula 2 may include, but may not be limited to, the following Chemical Formula 5:

[Chemical Formula 5a]

[Chemical Formula 5]

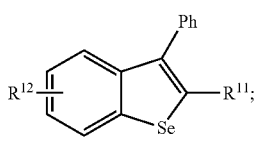

In the formulas,
X, $R^{11}$, and $R^{12}$ are the same as defined above in Chemical Formulas 2a and 2.

In accordance with an example embodiment, Chemical Formula 2a may include, but may not be limited to, the following Chemical Formula 6a, and Chemical Formula 2 may include, but may not be limited to, the following Chemical Formula 6:

[Chemical Formula 6a]

[Chemical Formula 6]

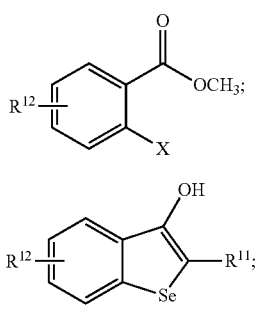

In the formulas,
X, $R^{11}$, and $R^{12}$ are the same as defined above in Chemical Formulas 2a and 2.

In accordance with an example embodiment, the base may be added subsequently after the aromatic starting material is added to the reaction mixture, but may not be limited thereto. By way of example, the base used for producing the selenophene-fused aromatic compound may be added subsequently after the aromatic starting material is added to the reaction mixture with stirring, but may not be limited thereto. The time for stirring may be about 10 minutes or more, but may not be limited thereto. By adding the base, the reducing agent containing a thiol group can be converted into a negatively charged thiolate anion($RS^-$) and a reducing power thereof can be improved.

By way of example, the reaction of producing the negatively charged thiolate anion by using a reducing agent containing a thiol group as the reducing agent can be schematized by a reaction mechanism shown below:

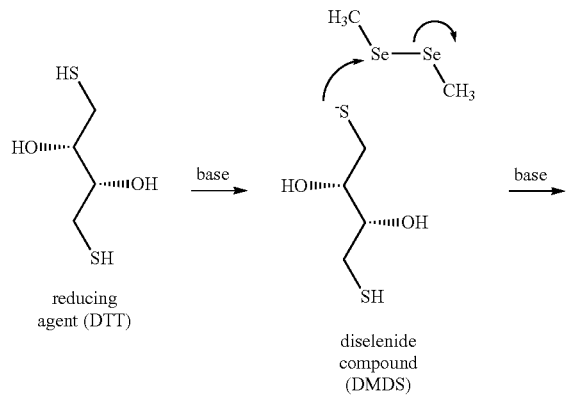

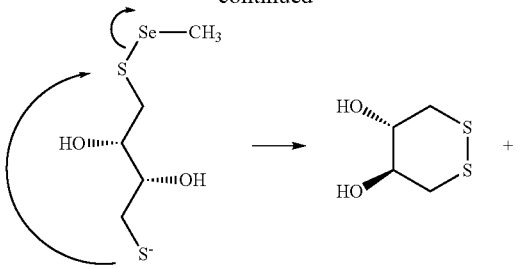

Meanwhile, if the negatively charged thiolate anion exists together with the aromatic starting material, it may compete with a selenolate nucleophile and cause a substitution reaction. Therefore, if the base is added from the first step of the reaction, i.e. the step where the reaction mixture is prepared, or if the base is added to the reaction mixture together with the aromatic starting material, the negatively charged thiolate anion reacts first with the diselenide compound rather than the aromatic starting material. Thus, a yield of a final target product may be decreased. Therefore, the aromatic starting material is added with stirring for a certain period of time, and then the base is added during the reaction, so that the above-described problem can be solved. Thus, the negatively charged thiolate anion can selectively make a nucleophilic substitution reaction first with the aromatic starting material, and a yield of the final target product can be improved.

For the reason described above, in an example embodiment, a producing method of a selenophene-fused aromatic compound including adding the aromatic starting material to the reaction mixture with stirring, and subsequently adding the base thereto, but may not be limited thereto. By way of example, it was observed that when the aromatic starting material was added to the reaction mixture containing the diselenide compound, the solvent, and the reducing agent with stirring for a certain period of time and then the base was added, a nucleophilic substitution reaction was preferably performed within a few minutes at a position of a halo group contained in the aromatic starting material and a desired reaction product, i.e. a selenophene-fused aromatic compound, was formed.

In accordance with an example embodiment, the solvent may be selected from the group consisting of dimethylformaldehyde (DMF), dimethylsulfoxide (DMSO), tetrahydrofuran (THF), $CH_2Cl_2$, $CH_3CN$, $CH_3NO_2$, $CHCl_3$, $ClCH_2CH_2Cl$, alcohols, an aromatic solvent, and combinations thereof, but may not be limited thereto. By way of example, the alcohols may include, but may not be limited to, methanol, ethanol, propanol, or butanol, and the aromatic solvent may include, but may not be limited to, benzene, toluene, or derivatives thereof. The solvent can be selectively used without particular limitation as long as it can easily dissolve the diselenide compound and the reducing agent contained in the reaction mixture.

In accordance with an example embodiment, the reducing agent may contain a thiol group, but may not be limited thereto. By way of example, the reducing agent may include a material containing one thiol group or more, but may not be limited thereto. By way of example, the reducing agent may include a material containing one or two thiol groups, and may include, for example, but not limited to, dithiothreitol (DTT), an isomer of dithiothreitol, cysteine, N-acetylcysteine, cysteine derivatives similar to N-Boc-cysteine, or alkandithiol such as 1,4-butandithiol or 1,6-hexandithiol. In order to prepare the selenophene-fused aromatic compound, in conventional methods, some reducing agents such as $NaBH_4$ or $LiEt_3BH$ that does not contain a thiol group have been used. Further, metals such as indium, lanthanum, and samarium, and salts thereof have been used for reducing a Se—Se bond of the diselenide compound to form a selenolate nucleophile. However, it is difficult to obtain the selenophene-fused aromatic compound by the above-described conventional methods. That is because according to the conventional methods, another functional group of the aromatic starting material may be reduced or converted at the same time when the Se—Se bond of the diselenide compound is reduced. In the example embodiments, instead of the above-described conventional methods, another functional group of the aromatic starting material was suppressed from being reduced or converted and the Se—Se bond of the diselenide compound was selectively reduced by using a material containing a thiol group as a reducing agent as described above, and, thus, a yield of the desired reaction product could be remarkably increased. That is, since the material containing a thiol group is used as the reducing agent, a yield of the selenophene-fused aromatic compound can be increased and unnecessary side reactions can be minimized.

In accordance with an example embodiment, the base may be selected from the group consisting of $K_2CO_3$, $KHCO_3$, $Na_2CO_3$, $NaHCO_3$, NaOEt, $NH_4OH$, DBU (1,8-diazabicyclo[5,4,0]undec-7-ene), KOH, NaOH, $Ca(OH)_2$, $Ba(OH)_2$, KOtBu, and combinations thereof, but may not be limited thereto. By way of example, the base may be a strong base selected from the group consisting of DBU(1,8-diazabicyclo[5,4,0]undec-7-ene), KOH, NaOH, $Ca(OH)_2$, $Ba(OH)_2$, KOtBu, and combinations thereof, but may not be limited thereto. By way of example, the base may be a weak base selected from the group consisting of $K_2CO_3$, $KHCO_3$, $Na_2CO_3$, $NaHCO_3$, NaOEt, $NH_4OH$, or combinations thereof, but may not be limited thereto. The selection of a base may affect a yield of the selenophene-fused aromatic compound. By way of example, if a material containing an electron donating substituent is used as the aromatic starting material, when a weak base such as NaOEt is used, it is difficult to obtain a desired product, whereas when a strong base such as DBU is used, it is possible to produce a desired product at a high yield, but the example embodiment may not be limited thereto.

In accordance with an example embodiment, preparing the reaction mixture and adding the aromatic starting material and the base to the reaction mixture to be reacted may be performed independently at a temperature of, but not limited to, from room temperature to about 100° C. The selection of a reaction temperature does not directly affect a high yield of the desired reaction product. Therefore, the reaction temperature can be selected without particular limitation as long it is in a range which does not greatly affect reactivity. By way of example, the reaction mixture is prepared and stirred at room temperature, the aromatic starting material is added to the reaction mixture with stirring at room temperature for a certain period of time, and then, the base is added thereto with stirring at room temperature, so that the selenophene-fused aromatic compound can be produced, but the example embodiment may not be limited thereto.

In accordance with an example embodiment, the diselenide compound as represented by the general formula $R^{11}$—$CH_2$—Se—Se—$CH_2$—$R^{11}$ is reduced by the reducing agent to form a selenolate nucleophile as represented by $R^{11}$—$CH_2$—Se$^-$, and the selenolate nucleophile makes a nucleophilic substitution reaction with the aromatic starting material to form the selenophene-fused aromatic compound, but the example embodiment may not be limited thereto. In the above-described example embodiment, the reaction in which the diselenide compound is reduced by the reducing agent and the selenolate nucleophile is formed has a reaction mechanism as represented by the following reaction formula. By way of example, in the following reaction formula, dimethyldiselenide (DMDS) is used as the diselenide compound and dithiothreitol (DTI) is used as the reducing agent, but the example embodiment may not be limited thereto:

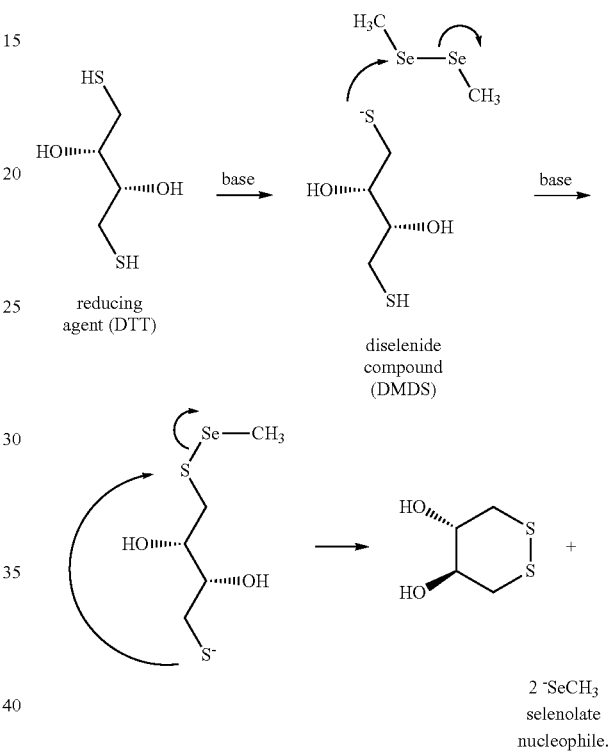

A third aspect of the example embodiments provides a producing method of a selenophene-fused aromatic compound represented by the following Chemical Formula 7, the method including: reacting an aromatic starting material represented by the following Chemical Formula 7a and $R^{11}CH_2X$ via heating to form a reaction intermediate represented by the following Chemical Formula 7b; and adding a solvent and a base to the reaction intermediate to be reacted:

[Chemical Formula 7a]

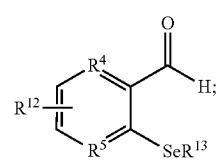

[Chemical Formula 7b]

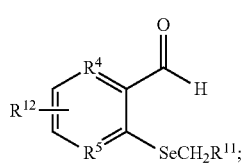

[Chemical Formula 7]

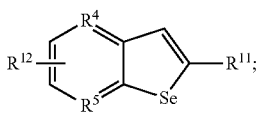

In the formulas, each of $R^4$ and $R^5$ independently represents a substitutable N, O, S, C, bond or a non-bonding, $R^{11}$ represents —$CO_2H$, —$CO_2R$, 4-$NO_2$-Ph, 4-CN-Ph, 4-$RO_2C$-Ph, or 4-X-Ph, $R^{12}$ represents H, —$NO_2$, —NHCOR, $CX_3$, —OR, -diOR, a substitutable alkoxy group, a substitutable alkylene-dioxy group, a substitutable amino group, or a halo group, X represents a halo group, $R^{13}$ represents a substitutable alkyl group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

Herein, if the $R^4$ is a "bond", two carbon atoms positioned on both sides of the $R^4$ are connected with each other through a direct carbon bond, and if the $R^5$ is a "bond", two carbon atoms positioned on both sides of the $R^5$ are connected with each other through a direct carbon bond.

Noticeable differences between the producing method in accordance of the third aspect of the example embodiments and the producing method in accordance with the second aspect of the example embodiments are that the reaction intermediate is formed in the producing method in accordance of the third aspect of the example embodiments and a reducing agent is not needed in the producing method in accordance of the third aspect of the example embodiments.

In accordance with an example embodiment, Chemical Formula 7a may include, but may not be limited to, the following Chemical Formula 8a, Chemical Formula 7b may include, but may not be limited to, the following Chemical Formula 8b, and Chemical Formula 7 may include, but may not be limited to, the following Chemical Formula 8:

[Chemical Formula 8a]

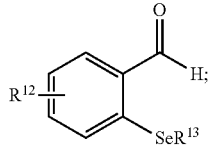

[Chemical Formula 8b]

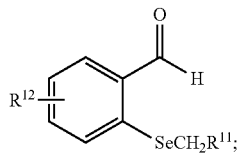

[Chemical Formula 8]

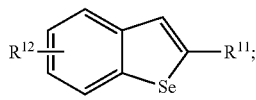

In the formulas, $R^{11}$, $R^{12}$, and $R^{13}$ are the same as defined above in Chemical Formula 7a, Chemical Formula 7b, and Chemical Formula 7.

In accordance with an example embodiment, Chemical Formula 7a may include, but may not be limited to, the following Chemical Formula 9a, Chemical Formula 7b may include, but may not be limited to, the following Chemical Formula 9b, and Chemical Formula 7 may include, but may not be limited to, the following Chemical Formula 9:

[Chemical Formula 9a]

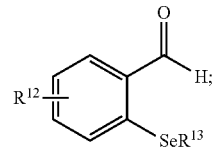

[Chemical Formula 9b]

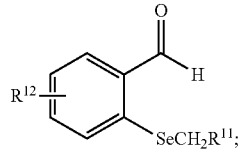

[Chemical Formula 9]

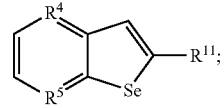

In the formulas, $R^4$, $R^5$, $R^{11}$, $R^{12}$, and $R^{13}$ are the same as defined above in Chemical Formula 7a, Chemical Formula 7b, and Chemical Formula 7.

In accordance with an example embodiment, the base may be added subsequently after the solvent is added to the reaction intermediate, but may not be limited thereto. As such, since the base is added after the solvent is added to the reaction intermediate, side reactions in which a thiol group is substituted with the starting material can be reduced.

In accordance with an example embodiment, the solvent may be selected from the group consisting of dimethylformaldehyde (DMF), dimethylsulfoxide (DMSO), tetrahydrofuran (THF), $CH_2Cl_2$, $CH_3CN$, $CH_3NO_2$, $CHCl_3$, $ClCH_2CH_2Cl$, alcohols, an aromatic solvent, and combinations thereof, but may not be limited thereto. By way of example, the alcohols may include, but may not be limited to, methanol, ethanol, propanol, or butanol, and the aromatic solvent may include, but may not be limited to, benzene, toluene, or derivatives thereof. The solvent can be selectively used without particular limitation as long as it can easily dissolve the reaction intermediate and the base.

In accordance with an example embodiment, the base may be selected from the group consisting of $K_2CO_3$, $KHCO_3$, $Na_2CO_3$, $NaHCO_3$, NaOEt, $NH_4OH$, DBU (1,8-diazabicyclo[5,4,0]undec-7-ene), KOH, NaOH, $Ca(OH)_2$, $Ba(OH)_2$, KOtBu, and combinations thereof, but may not be limited thereto. By way of example, the base may be a strong base selected from the group consisting of DBU(1,8-diazabicyclo[5,4,0]undec-7-ene), KOH, NaOH, $Ca(OH)_2$, $Ba(OH)_2$, KOtBu, and combinations thereof, but may not be limited thereto. By way of example, the base may be a weak base selected from the group consisting of $K_2CO_3$, $KHCO_3$, $Na_2CO_3$, $NaHCO_3$, NaOEt, $NH_4OH$, and combinations thereof, but may not be limited thereto. The selection of a base may affect a yield of the selenophene-fused aromatic compound. By way of example, if a material containing an electron donating substituent is used as the aromatic starting material, when a weak base such as NaOEt is used, it is difficult to obtain a desired product, whereas when a strong base such as DBU is used, it is possible to manufacture a desired product at a high yield, but the example embodiment may not be limited thereto.

In accordance with an example embodiment, the heating reaction to form the reaction intermediate may be performed at a temperature of, but not limited to, from about 100° C. to about 150° C. The heating reaction to form the reaction intermediate is performed at a temperature of, but not limited to, from about 100° C. to about 150° C. in order to form the reaction intermediate through an active reaction, the example embodiment may not be limited thereto.

A fourth aspect of the example embodiments provides a producing method of a selenophene-fused aromatic compound represented by the following Chemical Formula 10, the method including: reacting a MCBI (7-methoxy-1,2,9,9a-tetrahydrocyclopropa[c]benz[e]indol-4-one) compound represented by the following Chemical Formula 10a and a selenium-containing aromatic compound represented by the following Chemical Formula 10b:

[Chemical Formula 10a]

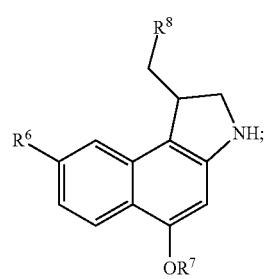

[Chemical Formula 10b]

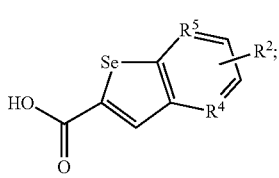

[Chemical Formula 10]

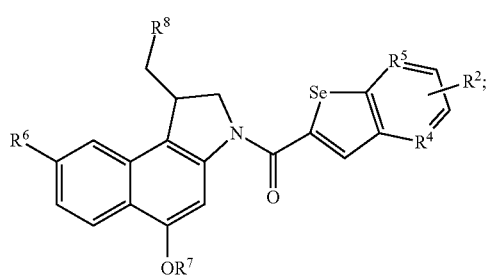

In the formulas,
R² represents a substitutable alkyl group, a substitutable alkoxy group, a halo group, —NO₂, —NHCOR, or a substituent represented by the following Chemical Formula B, each of R⁴ and R⁵ independently represents a substitutable C, O, N, S, bond or a non-bonding,
R⁶ represents H, or a substitutable alkoxy group,
R⁷ represents H, —CONR¹⁷R²⁰, or

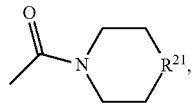

each of R¹⁷ and R²⁰ independently represents H, or a substitutable alkyl group,
R²¹ represents C, O, N, or S,
R⁸ represents a halo group, and
R represents H, a substitutable alkyl group, a substitutable aryl group, a substitutable amino group, a substitutable amino acid group, a substitutable peptide group, a substitutable C₁₋₇ alkoxy group, or a residue of a substitutable carbohydrate or carbohydrate derivative:

[Chemical Formula B]

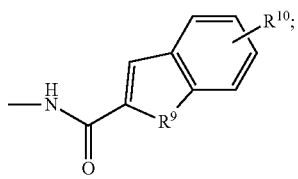

In the formula,
R⁹ represents O, NH, S, or Se,
R¹⁰ represents a substitutable alkyl group, a substitutable alkoxy group, a halo group, —NO₂, or —NHCOR,
R represents H, a substitutable alkyl group, a substitutable aryl group, a substitutable amino group, a substitutable amino acid group, a substitutable peptide group, a substitutable C₁₋₇ alkoxy group, or a residue of a substitutable carbohydrate or carbohydrate derivative.

By way of example, the selenophene-fused aromatic compound represented by Chemical Formula 10 above of the example embodiments may be easily produced by making a condensation polymerization reaction between NH of the MCBI represented by Chemical Formula 10a above and a carboxy group of the selenium-containing aromatic compound represented by Chemical Formula 10b in the presence of EDCI and a solvent, but may not be limited thereto. Since the selenophene-fused aromatic compound is easily and economically produced in accordance with the example embodiments, it is possible to promote commercialization of the selenophene-fused aromatic compound.

In accordance with an example embodiment, the MCBI compound represented by Chemical Formula 10a above may be produced from a MCBI compound represented by the following Chemical Formula 10c in an acidic condition, but may not be limited thereto:

[Chemical Formula 10c]

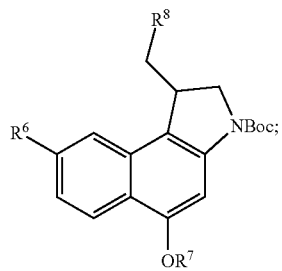

In the formula,

R⁶, R⁷, and R⁸ are the same as defined above in Chemical Formula 10a.

The MCBI compound represented by Chemical Formula 10c above is included in a "Boc-MCBI compound", and the MCBI compound represented by Chemical Formula 10a above is included in a "seco-MCBI compound". By way of example, the seco-MCBI compound may be produced by a typical method using the Boc-MCBI compound as a starting material, but may not be limited thereto. By way of example, the seco-MCBI compound may be easily produced by treating and reacting the Boc-MCBI compound with HCl and EtOAc, but may not be limited thereto.

In accordance with an example embodiment, the MCBI compound represented by Chemical Formula 10a above may be produced from the MCBI compound represented by Chemical Formula 10c above in an acidic condition, but may not be limited thereto. By way of example, the acidic condition may be formed through a treatment with an organic acid such as HCl or the like, but may not be limited thereto.

In accordance with an example embodiment, the selenium-containing aromatic compound represented by Chemical Formula 10b above may be produced from a selenium-containing aromatic compound represented by the following Chemical Formula 10d in a basic condition, but may not be limited thereto:

[Chemical Formula 10d]

In the formula,

R², R⁴, and R⁵ are the same as defined above in Chemical Formula 10b, and

R¹⁸ represents a substitutable alkyl group, a substitutable alkoxy group, —NO₂, or —NHCO₂H.

R¹⁸ may be an alkyl group, an alkoxy group, —NO₂, or —NHCO₂H, but may not be limited thereto. By way of example, the selenium-containing aromatic compound represented by Chemical Formula 10b above may be easily produced by hydrolyzing —CO₂R¹⁸ of the selenium-containing aromatic compound represented by Chemical Formula 10d above, but may not be limited thereto. By way of example, in order to perform the hydrolysis, LiOH and THF—H₂O-MeOH may be treated and reacted, but the example embodiment may not be limited thereto.

In accordance with an example embodiment, the selenium-containing aromatic compound represented by Chemical Formula 10b above may be produced from the selenium-containing aromatic compound represented by Chemical Formula 10d above in a basic condition, but may not be limited thereto. By way of example, the basic condition may be formed through a treatment with a basic material such as LiOH or the like, but may not be limited thereto.

In accordance with an example embodiment, the reaction between the MCBI compound represented by Chemical Formula 10a above and the selenium-containing aromatic compound represented by Chemical Formula 10b above may be performed in the presence of EDCI, but may not be limited thereto.

In accordance with an example embodiment, the reaction between the MCBI compound represented by Chemical Formula 10a above and the selenium-containing aromatic compound represented by Chemical Formula 10b above may be performed after the MCBI compound is dissolved in a solvent, but may not be limited thereto.

In accordance with an example embodiment, the solvent may be selected from the group consisting of dimethylformaldehyde (DMF), dimethylsulfoxide (DMSO), tetrahydrofuran (THF), CH₂Cl₂, CH₃CN, CH₃NO₂, CHCl₃, ClCH₂CH₂Cl, alcohols, an aromatic solvent, and combinations thereof, but may not be limited thereto. By way of example, the alcohols may include, but may not be limited to, methanol, ethanol, propanol, or butanol, and the aromatic solvent may include, but may not be limited to, benzene, toluene, or derivatives thereof. The solvent can be selectively used without particular limitation as long as it can easily dissolve the MCBI compound.

A fifth aspect of the example embodiments provides a producing method of a selenophene-fused aromatic compound represented by the following Chemical Formula 11, the method including: reacting a MCBI compound represented by the following Chemical Formula 11a and a selenium-containing aromatic compound represented by the following Chemical Formula 11b:

[Chemical Formula 11a]

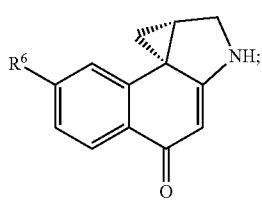

[Chemical Formula 11b]

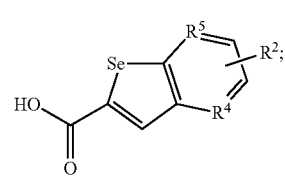

[Chemical Formula 11]

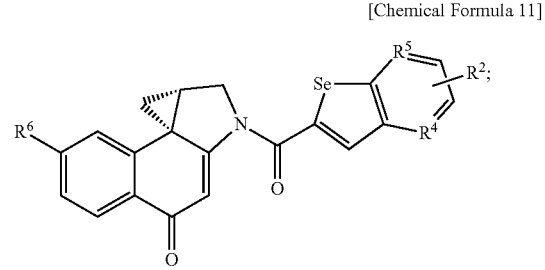

In the formulas,

R² represents a substitutable alkyl group, a substitutable alkoxy group, a halo group, —NO₂, — NHCOR, or a substituent represented by the following Chemical Formula B, each of R⁴ and R⁵ independently represents a substitutable C, O, N, S, bond or a non-bonding, R⁶ represents H, or a substitutable alkoxy group, and R represents H, a substitutable alkyl group, a substitutable aryl group, a substitutable amino group, a substitutable amino acid group, a substitutable peptide group, a substitutable C₁₋₇ alkoxy group, or a residue of a substitutable carbohydrate or carbohydrate derivative:

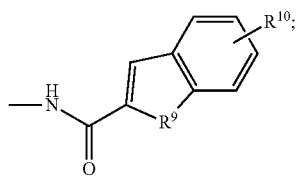

[Chemical Formula B]

In the formula, $R^9$ represents O, NH, S, or Se, $R^{10}$ represents a substitutable alkyl group, a substitutable alkoxy group, a halo group, —$NO_2$, or —NHCOR, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

By way of example, the selenophene-fused aromatic compound represented by Chemical Formula 11 above of the fifth aspect of the example embodiments may be easily produced by making a condensation polymerization reaction between NH of the MCBI represented by Chemical Formula 11a above and a carboxy group of the selenium-containing aromatic compound represented by Chemical Formula 11b in the presence of EDCI and a solvent, but may not be limited thereto. Since the selenophene-fused aromatic compound is easily and economically produced in accordance with the example embodiments, it is possible to promote commercialization of the selenophene-fused aromatic compound.

In accordance with an example embodiment, the MCBI compound represented by Chemical Formula 11a above may be produced from a MCBI compound represented by the following Chemical Formula 11c in an acidic condition, but may not be limited thereto:

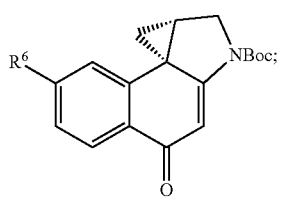

[Chemical Formula 11c]

In the formula, $R^6$ is the same as defined above in Chemical Formula 11a.

The MCBI compound represented by Chemical Formula 11c above is included in the "Boc-MCBI compound", and the MCBI compound represented by Chemical Formula 11a above is included in the "seco-MCBI compound". By way of example, the seco-MCBI compound may be produced by a typical method using the Boc-MCBI compound as a starting material, but may not be limited thereto. By way of example, the seco-MCBI compound may be easily produced by treating and reacting the Boc-MCBI compound with HCl and EtOAc, but may not be limited thereto.

In accordance with an example embodiment, the MCBI compound represented by Chemical Formula 11a above may be produced from the MCBI compound represented by Chemical Formula 11c above in an acidic condition, but may not be limited thereto. By way of example, the acidic condition may be formed through a treatment with an organic acid such as HCl or the like, but may not be limited thereto.

In accordance with an example embodiment, the selenium-containing aromatic compound represented by Chemical Formula 11b above may be produced from a selenium-containing aromatic compound represented by the following Chemical Formula 11d in a basic condition, but may not be limited thereto:

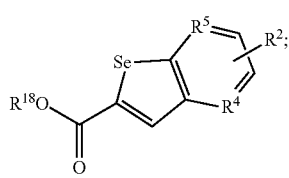

[Chemical Formula 11d]

In the formula, $R^2$, $R^4$, and $R^5$ are the same as defined above in Chemical Formula 11b, and $R^{18}$ represents a substitutable alkyl group, a substitutable alkoxy group, —$NO_2$, or —$NHCO_2H$.

$R^{18}$ may be an alkyl group, an alkoxy group, —$NO_2$, or —$NHCO_2H$, but may not be limited thereto. By way of example, the selenium-containing aromatic compound represented by Chemical Formula 11b above may be easily produced by hydrolyzing —$CO_2R^{18}$ of the selenium-containing aromatic compound represented by Chemical Formula 11d above, but may not be limited thereto. By way of example, in order to perform the hydrolysis, LiOH and THF—$H_2O$-MeOH may be treated and reacted, but the example embodiment may not be limited thereto.

In accordance with an example embodiment, the selenium-containing aromatic compound represented by Chemical Formula 11b above may be produced from the selenium-containing aromatic compound represented by Chemical Formula 11d above in a basic condition, but may not be limited thereto. By way of example, the basic condition may be formed through a treatment with a basic material such as LiOH or the like, but may not be limited thereto.

In accordance with an example embodiment, the reaction between the MCBI compound represented by Chemical Formula 11a above and the selenium-containing aromatic compound represented by Chemical Formula 11b above may be performed in the presence of EDCI, but may not be limited thereto.

In accordance with an example embodiment, the reaction between the MCBI compound represented by Chemical Formula 11a above and the selenium-containing aromatic compound represented by Chemical Formula 11b above may be performed after the MCBI compound is dissolved in a solvent, but may not be limited thereto.

In accordance with an example embodiment, the solvent may include a member selected from the group consisting of dimethylformaldehyde (DMF), dimethylsulfoxide (DMSO), tetrahydrofuran (THF), $CH_2Cl_2$, $CH_3CN$, $CH_3NO_2$, $CHCl_3$, $ClCH_2CH_2Cl$, alcohols, an aromatic solvent, and combinations thereof, but may not be limited thereto. By way of example, the alcohols may include, but may not be limited to, methanol, ethanol, propanol, or butanol, and the aromatic solvent may include, but may not be limited to, benzene, toluene, or derivatives thereof. The solvent can be selectively used without particular limitation as long as it can easily dissolve the MCBI compound.

A sixth aspect of the example embodiments provides an anti-bacterial composition including a selenophene-fused aromatic compound in accordance with the first aspect of the example embodiments. If the selenophene-fused aromatic compound has an anti-bacterial property, it can be used as an intermediate of a drug or a finished product.

A seventh aspect of the example embodiments provides an indicator composition including a selenophene-fused aromatic compound in accordance with the first aspect of the example embodiments, and the indicator may be used as an indicator of which color is changed depending on a solvent. A property of a substance to change color depending on a solvent is referred to as "solvatochromic", and a substance having the solvatochromic property can be used as an indicator, a solvatochromic ink, or the like. The selenophene-fused aromatic compound having the solvatochromic property may include, for example, the following compound. The following compound which has the solvatochromic property and thus can be used as an indicator corresponds to Entry 17 of [Table 1] shown in Example:

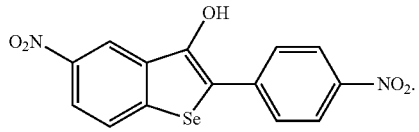 [SMILES: O=[N+]([O-])c1ccc(-c2[se]c3ccc([N+](=O)[O-])cc3c2O)cc1]

Figure 4:
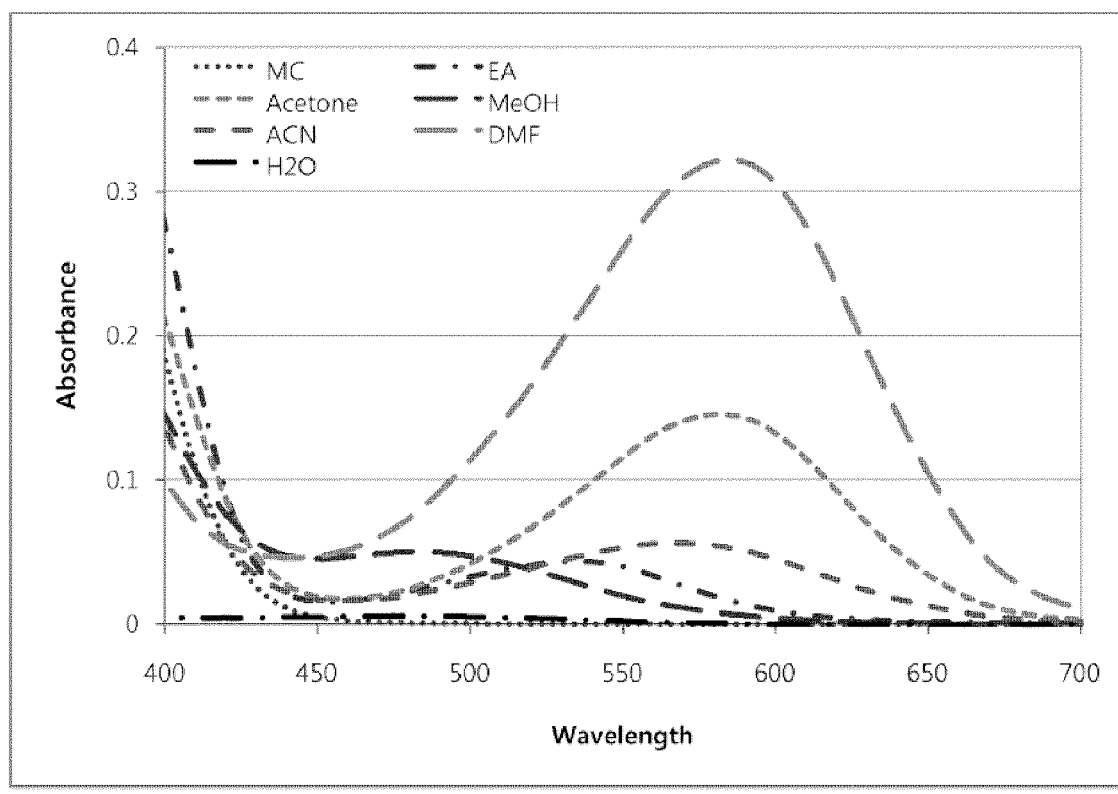
FIG. 4 is spectra showing a solvatochromic property of a selenophene-fused aromatic compound produced according to Entry 17 of Example.

In this regard, FIG. 4 is an absorption spectrum showing a solvatochromic property of a selenophene-fused aromatic compound produced according to Entry 17 of Example, and a concentration of the compound at the time of measuring the spectrum was about 60.4 µM.

An eighth aspect of the example embodiments provides a fluorescent composition including a selenophene-fused aromatic compound in accordance with the first aspect of the example embodiments. The selenophene-fused aromatic compound having a fluorescent property can be used as an intermediate for synthesizing organic semiconductors. The selenophene-fused aromatic compound having the fluorescent property may include, for example, the following compounds. The following compounds which have the fluorescent property and thus can be used as an intermediate for synthesizing organic semiconductors correspond to Entry 26, Entry 27, and Entry 30 of [Table 2] shown in Example:

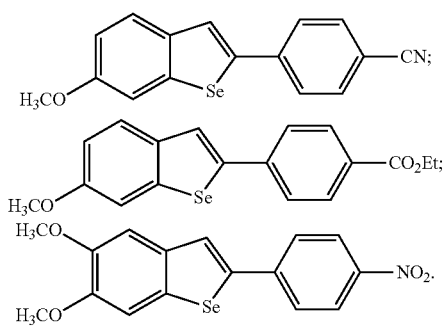

Figure 2:
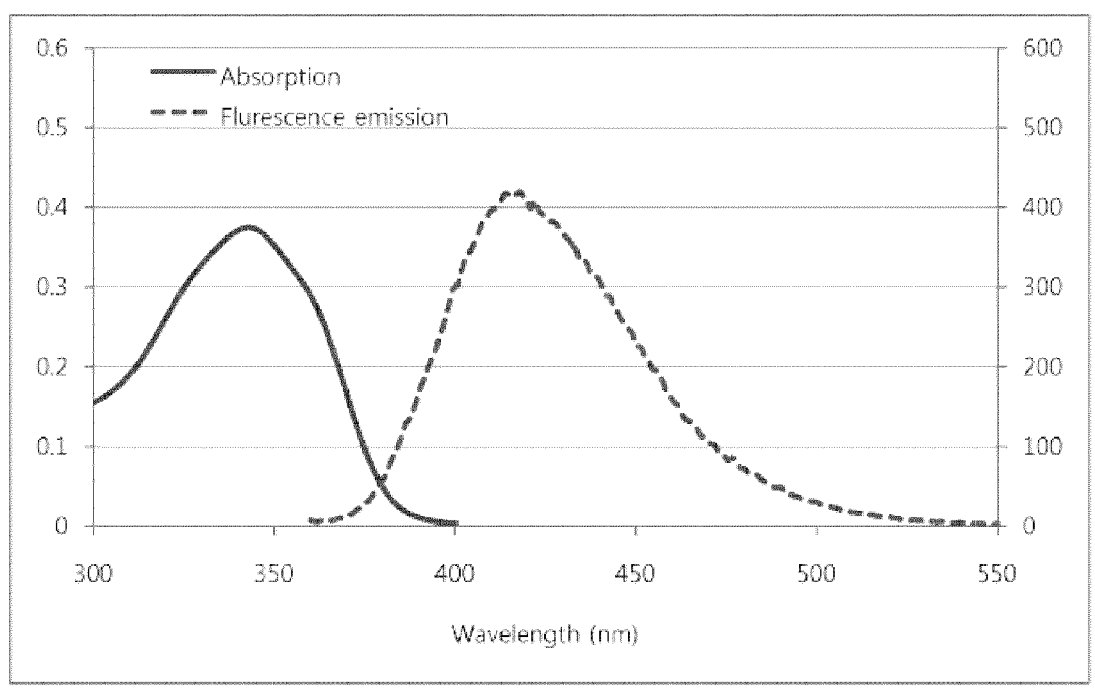
FIG. 2 is spectra showing a fluorescent property of a selenophene-fused aromatic compound produced according to Entry 27 of Example.
Figure 3:
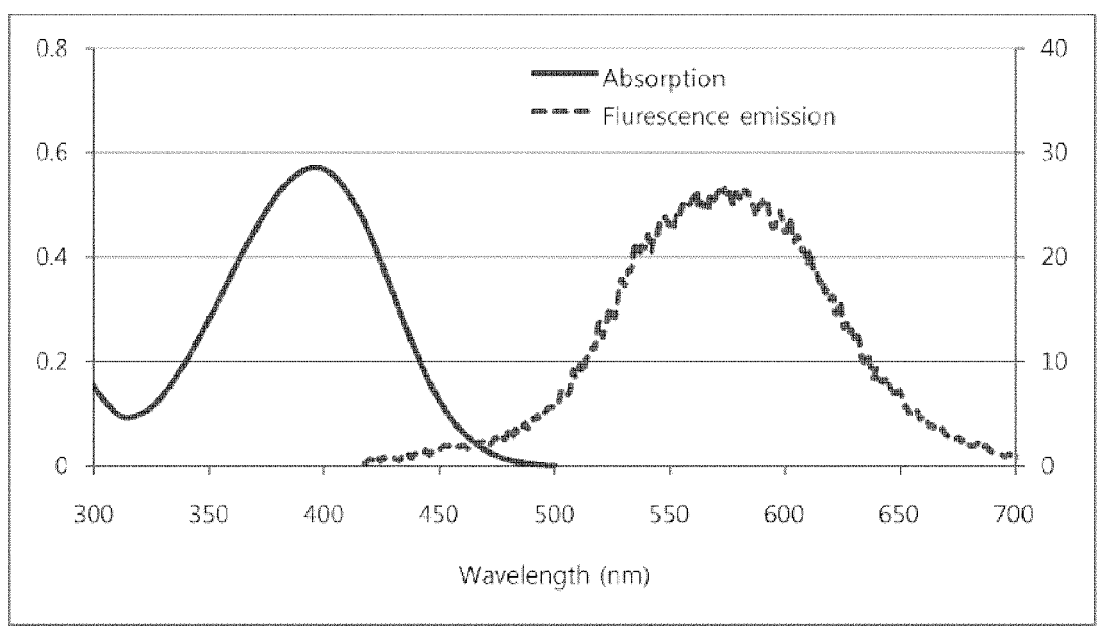
FIG. 3 is spectra showing a fluorescent property of a selenophene-fused aromatic compound produced according to Entry 30 of Example.

In this regard, FIG. 1 to FIG. 3 are spectra showing a fluorescent property of respective selenophene-fused aromatic compounds produced according to Entry 26, Entry 27, and Entry 30 of Example.

A ninth aspect of the example embodiments provides an anticancer composition including a selenophene-fused aromatic compound in accordance with the first aspect of the example embodiments. If the selenophene-fused aromatic compound has an anticancer property, it can be used as an intermediate of a drug or a finished product. The selenophene-fused aromatic compound can exhibit an anticancer effect though DNA alkylation. It is confirmed that as a result of cytotoxicity tests carried out to various cancer cells, the selenophene-fused aromatic compound has an $IC_{50}$ value in nM or pM exhibits a potent anticancer effect. Further, the selenophene-fused aromatic compound can be applied to various cancers such as breast cancer, central nervous system cancer, colorectal cancer, non-small cell lung cancer, renal cancer, prostate cancer, ovarian cancer, etc., and, thus, the selenophene-fused aromatic compound in accordance with the example embodiments is expected to be usefully used as an anticancer drug for various cancers.

MODE FOR CARRYING OUT THE INVENTION

Hereinafter, the example embodiments of the present disclosure will be described in more detail with reference to Example, but the present disclosure may not be limited thereto.

EXAMPLES

All reagents used in the present Example are commercially available and used as being unprocessed unless specific description is provided to contrary.

1. Producing Method of a Selenophene-Fused Aromatic Compound in Accordance With the Second Aspect of Example Embodiments In the present Example, a selenophene-fused aromatic compound in accordance with the second aspect of example embodiments was produced as follows.

In order to prepare a reaction mixture, a diselenide compound represented by a general formula $R^{11}$—$CH_2$—Se—Se—$CH_2$—$R^{11}$, a solvent, and a reducing agent were prepared. As the diselenide compound represented by the general formula $R^{11}$—$CH_2$—Se—Se—$CH_2$—$R^{11}$ of the reaction mixture, various substances such as $(SeCH_2COOEt)_2$, $(p\text{-}NO_2PhCH_2Se)_2$, $(p\text{-}CNPhCH_2Se)_2$, and the like were used. The diselenide compounds were as shown in [Table 1]. About 0.6 eq. of the diselenide compound was used. As the solvent, anhydrous dimethylformaldehyde (DMF) was used. Further, as the reducing agent, about 0.6 eq. of dithiothreitol (DTT) was used.

To be specific, the reaction mixture was prepared by adding the diselenide compound represented by the general formula $R^{11}$—$CH_2$—Se—Se—$CH_2$—$R^{11}$ and the reducing agent to 2 mL of the solvent. The reaction mixture was stirred for 1 hour at a constant temperature of 60° C.

After the reaction mixture was prepared, an aromatic compound as a starting material for producing the selenophene-fused aromatic compound was added to the reaction mixture at a time. Then, the reaction mixture was stirred for 30 minutes at a constant temperature of 60° C.

As the base to be added after the starting material is added to the reaction mixture with stirring, a weak base $K_2CO_3$ was used. 2.5 eq. of the base was added to the reaction mixture at room temperature with stirring for 24 hours at a constant temperature of 60° C.

After the base was added and the stirring was finished, it was observed that the starting material was completely consumed by using a thin layer chromatography in a mixture of ethyl acetate:hexane (EA:Hex). The solvent contained in the reaction mixture was removed in a vacuum, and a crude solid was extracted 3 times by using about 25 mL of a solvent including dichloromethane:water (1:1). An organic phase collected through the extraction process was dried in an anhydrous environment by using $MgSO_4$, and the solvent was evaporated in a vacuum. The residue was refined by column chromatography using a silica gel column. A pure product, i.e. the selenophene-fused aromatic compound produced in the present Example, was eluted by using ethyl acetate and hexane, and recrystallized by using methanol and then filtered.

In the present Example, a producing process of selenophene-fused aromatic compounds corresponding to Entry 1 to Entry 17 is shown in the following schemes. Herein, the term "Entry" refers to subdivision of the present Example according to the aromatic starting material and the diselenide compound used herein. The aromatic starting materials and the diselenide compounds used herein were as shown in [Table 1].

[Scheme 1] Entry 1 to Entry 11

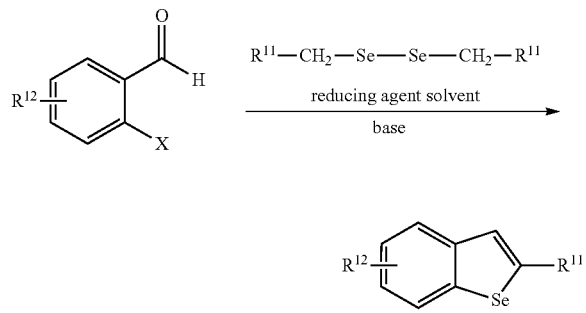

[Scheme 2] Entry 12 and Entry 13

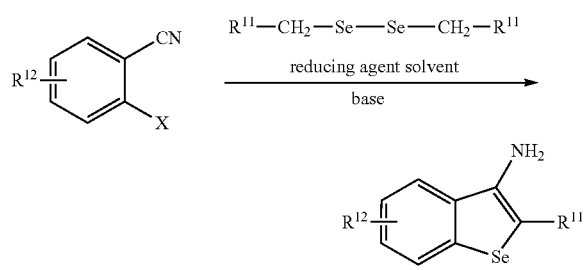

[Scheme 3] Entry 14 and Entry 15

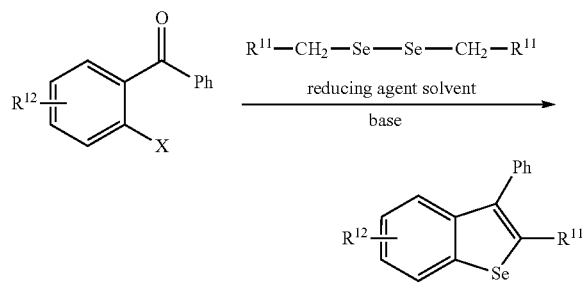

[Scheme 4] Entry 16 and Entry 17

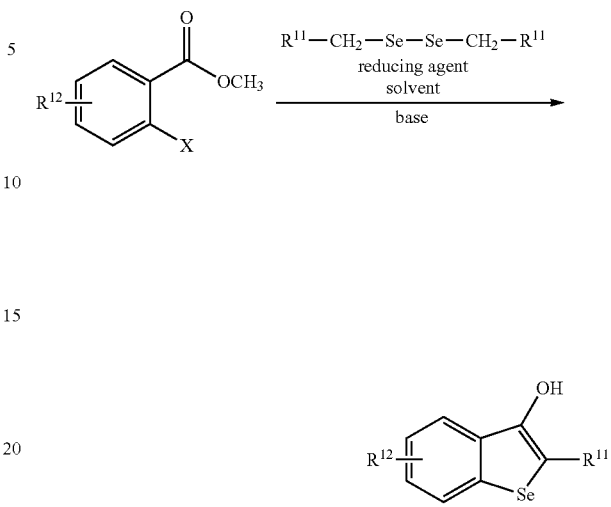

2. Producing Method of a Selenophene-Fused Aromatic Compound in Accordance with the Third Aspect of Example Embodiments In the present Example, a selenophene-fused aromatic compound in accordance with the third aspect of example embodiments was produced as follows.

In order to form a reaction intermediate, an aromatic starting material and $R^{11}CH_2X$ were prepared. 1 eq. of the aromatic starting material was used, and 20 eq. of the $R^{11}CH_2X$ was used. The aromatic starting materials and the diselenide compounds used herein were as shown in [Table 2].

In order to form the reaction intermediate, a mixture of the aromatic starting material and the $R^{11}CH_2X$ was put in a heating box and heated at 130° C. for 17 hours. Then, the solution was cooled and the solvent was removed in a vacuum condition, so that the reaction intermediate in a sold form was obtained.

Thereafter, the reaction intermediate was dissolved in anhydrous dimethylformaldehyde (DMF) as a solvent, and 2.5 eq. of a weak base $K_2CO_3$ was added thereto, and stirred at room temperature for 24 hours.

After the base was added and the stirring was finished, it was observed that the starting material was completely consumed by using a thin layer chromatography in a mixture of ethyl acetate:hexane (EA:Hex). The solvent contained in the reaction mixture was removed in a vacuum, and a crude solid was extracted 3 times by using 25 mL of a solvent including dichloromethane:water (1:1). An organic phase collected through the extraction process was dried in an anhydrous environment by using $MgSO_4$, and the solvent was evaporated in a vacuum. The residue was refined by a column chromatography using a silica gel column. A pure product, i.e. the selenophene-fused aromatic compound produced in the present Example, was eluted by using ethyl acetate and hexane, and recrystallized by using methanol and then filtered.

In the present Example, a producing process of selenophene-fused aromatic compounds corresponding to Entry 21 to Entry 37 is shown in the following scheme. Herein, the term "Entry" refers to subdivision of the present Example according to an aromatic starting material and $R^{11}CH_2X$ used herein. The aromatic starting materials and the $R^{11}CH_2X$ used herein were as shown in [Table 2].

[Scheme 5] Entry 21 to Entry 33

[Scheme 6] Entry 34 to Entry 37

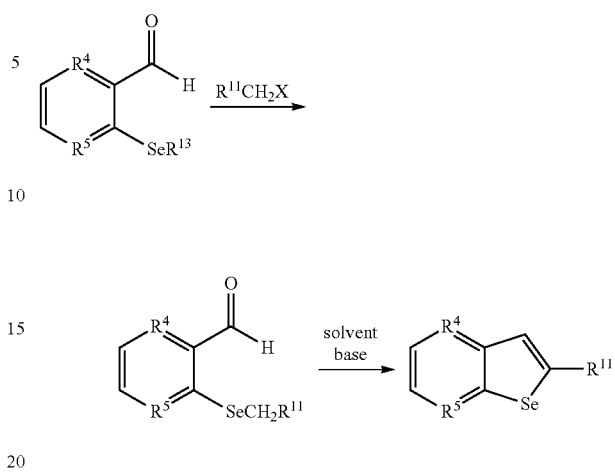

3. Producing Method of Selenophene-Fused Aromatic Compounds Corresponding to Entry 38 to Entry 41

In the present Example, a producing process of selenophene-fused aromatic compounds corresponding to Entry 38 to Entry 41 was as shown in the following scheme.

[Scheme 7] Entry 38 to Entry 41

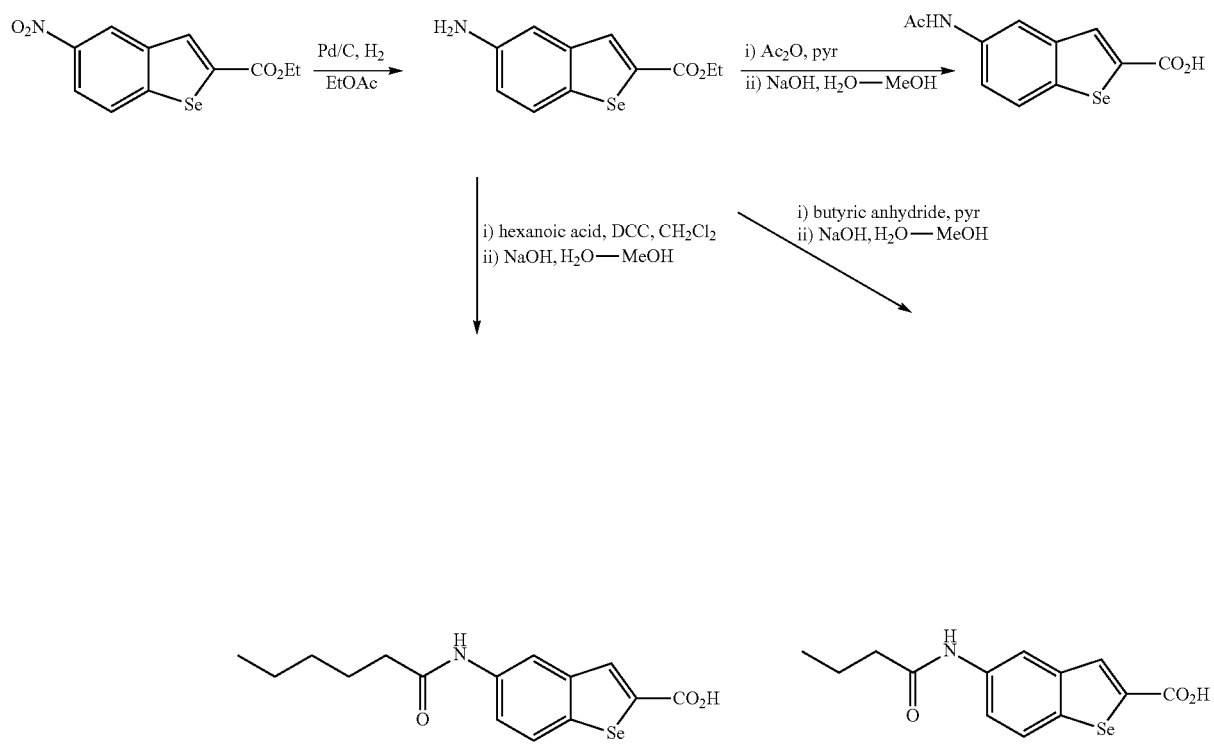

The selenophene-fused aromatic compounds corresponding to Entry 38 to Entry 41 were produced by performing an additional reaction to compounds containing a nitro group among the selenophene-fused aromatic compounds corresponding to Entry 1 to Entry 37, and a producing method was performed as follows.

In order to produce the selenophene-fused aromatic compound corresponding to Entry 38, 1.3 g of the compound corresponding to Entry 1 as a starting material was put into a 250 mL R.B. flask, and 100 mL of anhydrous ethyl acetate was added thereto, and then, the flask was filled with a nitrogen gas. 350 mg of 10% Pd/C was added to the compound, and a hydrogen gas was added with stirring for 24 hours. A catalyst was removed from the reaction compound through a silica pad, and the reaction compound was washed with ethyl acetate. Then, the obtained solution was concentrated under a depressurized condition. As a result, 1.11 g of a pure amino derivative was obtained. In this case, a yield was 98%.

Then, in order to produce the selenophene-fused aromatic compound corresponding to Entry 39, 0.691 g of the selenophene-fused aromatic compound corresponding to Entry 38 was dissolved in 10 mL of pyridine, and 0.48 mL of acetic anhydride was added thereto with stirring at room temperature. The reaction was checked by using a thin layer chromatography. The solvent was depressurized and removed, and the residue passed through a silica gel column, so that 765 mg of an amide derivative was obtained. This substance was hydrolyzed by using 20 mL of a mixed solution including a 2N—NaOH aqueous solution and MeOH at a ratio of 1:1. After the reaction was finished, the reaction solution was depressurized to remove MeOH and adjusted to be acidic by using a 2N HCl solution and then, the reaction product was extracted by using dichloromethane. Then, an organic solvent layer was concentrated, and by silica gel chromatography using EA/Hex (1:1), the compound corresponding to Entry 39 was obtained at a yield of 89%.

In order to produce the compound corresponding to Entry 40, a reaction was performed in a similar manner to the method for synthesizing the compound corresponding to Entry 39 from the compound corresponding to Entry 38. That is, 200 mg of an amine derivative was dissolved in 10 mL of pyridine, and 0.184 mL (1.5 eq.) of butyric anhydride was added thereto and reacted at room temperature, and then, the reaction product was refined. Thus, 227 mg of a butylamide derivative was obtained at a yield of 89%. 166 mg thereof was hydrolyzed by the same method as the synthesis of the compound corresponding to Entry 39. As a result, 150 mg of the compound corresponding to Entry 40 was obtained.

In order to produce the compound corresponding to Entry 41, 300 mg of an amine derivative was dissolved in 10 mL of pyridine, and 0.424 mL (3.0 eq.) of hexaenoic acid and 347 mg (1.5 eq.) of DCC were added thereto and reacted at room temperature for 4 hours, and then, extracted and refined in a similar manner to the synthesis of the compound corresponding to Entry 39. Thus, 264 mg of a hexyl amide derivative was obtained at a yield of 64%. This compound was hydrolyzed and refined by the same method as the synthesis of the compound corresponding to Entry 39. As a result, 232 mg of the compound corresponding to Entry 41 was obtained at a yield of 95%.

4. Producing Method of Selenophene-Fused Aromatic Compounds Corresponding to Entry 42 and Entry 43

In the present Example, a producing process of selenophene-fused aromatic compounds corresponding to Entry 42 and Entry 43 was as shown in the following scheme.

[Scheme 8] Entry 42 and Entry 43

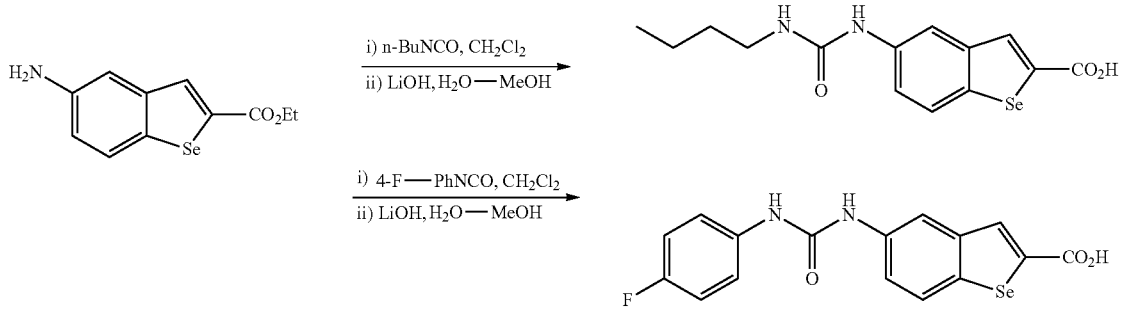

The selenophene-fused aromatic compounds corresponding to Entry 42 and Entry 43 were produced by performing an additional reaction to the selenophene-fused aromatic compounds corresponding to Entry 1 to Entry 37, and a producing method was performed as follows.

In order to synthesize the selenophene-fused aromatic compound corresponding to Entry 42, 50 mg of the compound corresponding to Entry 38 as an amine derivative was dissolved in 10 mL of anhydrous methylene chloride and nitrogen gas was added and then, cooled to 0° C. A solution in which 55 mg (3 eq.) of butyl isocyanate was dissolved in 60 mL of anhydrous methylene chloride was added to the reaction solution for 20 minutes with stirring at room temperature for 12 hours. The solvent was depressurized and removed, and a yellow solid was obtained and washed with a solution including pentane and ether (7:1), so that 55 mg of a yellow solid was obtained at a yield of 87%. This intermediate was dissolved in 1.5 mL of THF-MeOH—H₂O (4:1:1), and LiOH (3 eq.) was added thereto with stirring at room temperature for 18 hours. 6 mL of water was added thereto, and the reaction solution was acidified with a 10% HCl solution, and then, the reaction product was extracted by using methylene chloride. Then, an organic solvent layer was concentrated and separated by a silica gel chromatography using MeOH—CH₂Cl₂ (1:20), and 49 mg of the compound corresponding to Entry 42 was obtained at a yield of 91%.

In order to synthesize the selenophene-fused aromatic compound corresponding to Entry 43, 145 mg of urea as a brown solid intermediate was obtained by using 100 mg of the compound corresponding to Entry 38 and 4-fluorophenyl isocyanate (153 mg, 3 eq.) in a similar manner to the synthesis of the compound corresponding to Entry 42, and a reaction similar to the above-described hydrolysis was performed.

Then, through a separation and refinement process, 105 mg of the compound corresponding to Entry 43 was obtained in a brown solid form at a yield of 79%.

5. Producing Method of Selenophene-Fused Aromatic Compounds Corresponding to Entry 44 to Entry 46

In the present Example, a producing process of selenophene-fused aromatic compounds corresponding to Entry 44 to Entry 46 was as shown in the following scheme.

[Scheme 9] Entry 44 to Entry 46

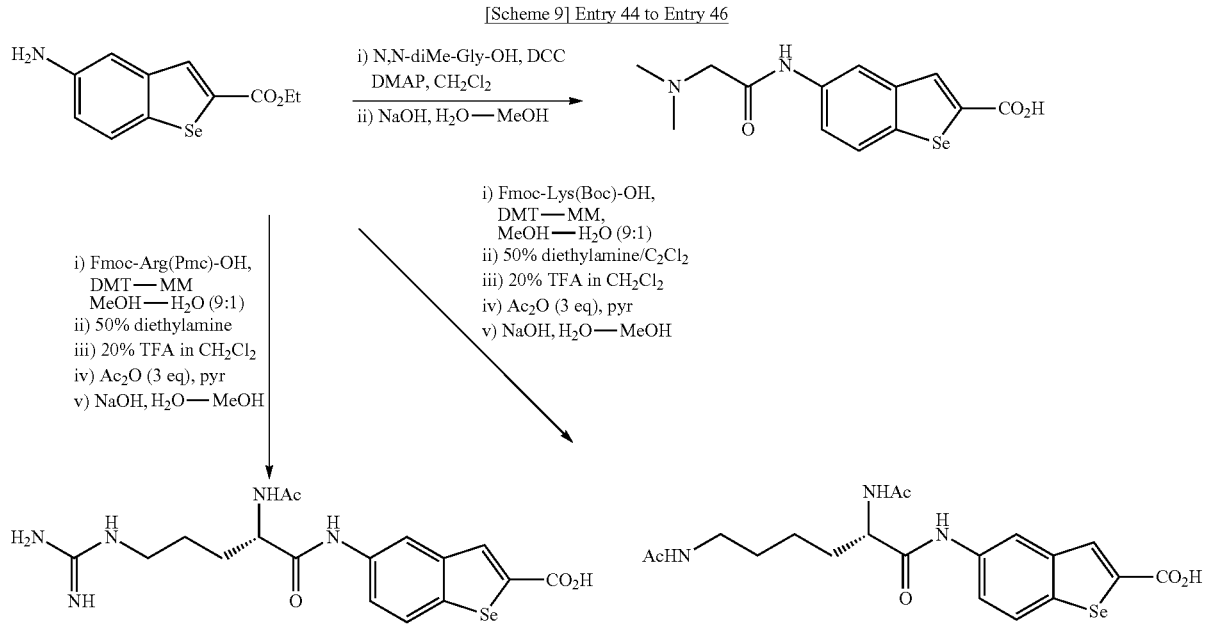

Producing Method:

In order to synthesize the selenophene-fused aromatic compound corresponding to Entry 44, 300 mg (3 eq.) of N,N-dimethylglycine was dissolved in 20 mL of anhydrous methylene chloride and DCC (206 mg, 4 eq.), DMAP (119 mg, 1 eq.), and pyridine (0.47 mL, 6 eq.) were added with stirring for 15 minutes. The compound (260 mg, 1 eq.) corresponding to Entry 38 as an amine derivative was added with stirring for 24 hours, and 50 mL of water was added, and then, the reaction product was extracted by using 200 mL of methylene chloride. Then, an organic solvent layer was concentrated and separated by a silica gel chromatography using EA-hex (1:1), and 420 mg of an intermediate was obtained at a yield of 80%. 400 mg of this intermediate was dissolved in 20 mL of MeOH—$H_2O$ (9:1) and NaOH (5 eq.) was added thereto with stirring at room temperature for 24 hours. The reaction solution was acidified with 2 mL of a 20% HCl solution and concentrated by using a lyophilizer and then separated by silica gel chromatography using MeOH—$CH_2Cl_2$ (1:4). As a result, 220 mg of the compound corresponding to Entry 44 was obtained at a yield of 60%.

In order to synthesize the selenophene-fused aromatic compound corresponding to Entry 45, 18 mL of methanol and 2 mL of water were added to Fmoc-Lys(Boc)-OH (436 mg) and amino benzoselenophene (300 mg, 1.2 eq.) with stirring for 15 minutes. Then, DMT-MM (385 mg, 1.5 eq.) was added thereto and reacted for 8 hours. 50 mL of water was added, and then, the reaction product was extracted by using 200 mL of methylene chloride. Then, an organic solvent layer was concentrated and separated by silica gel chromatography using EA-hex (1:1), and 586 mg of an intermediate was obtained at a yield of 88%. This intermediate was dissolved in 10 mL of a 20% TFA-methylene chloride (1:4) solution and reacted at 0° C. for 2 hours. The solvent was depressurized and concentrated and then dissolved in 50 mL of a DEA-methylene chloride (1:1) solution with stirring for about 2 hours. After the solvent was depressurized and concentrated, the solvent was dissolved in 10 mL of pyridine, and 0.24 mL (3 eq.) of anhydrous acetic acid was added thereto with stirring at room temperature for 3 hours. This reaction solution was depressurized and concentrated, and dissolved in 20 mL of MeOH—$H_2O$ (9:1), and then, NaOH (5 eq.) was added thereto with stirring at room temperature for 24 hours. The reaction solution was acidified with 2 mL of a 20% HCl solution and concentrated by using a lyophilizer and then separated by silica gel chromatography using MeOH—$CH_2Cl_2$ (1:4). As a result, 20 mg of the compound corresponding to Entry 45 was obtained.

In order to synthesize the selenophene-fused aromatic compound corresponding to Entry 46, 18 mL of methanol and 2 mL of water were added to Fmoc-Arg(Pmc)-OH (824 mg) and amino benzoselenophene (400 mg, 1.2 eq.) with stirring for 15 minutes. Then, DMT-MM (520 mg, 1.5 eq.) was added thereto and reacted for 8 hours. 50 mL of water was added, and then, the reaction product was extracted by using 200 mL of methylene chloride. Then, an organic solvent layer was concentrated and separated by silica gel chromatography using EA-hex (1:2), and 870 mg of an intermediate was obtained at a yield of 73%. 611 mg of this intermediate was dissolved in 10 mL of a DEA-methylene chloride (1:1) solution and reacted for 2 hours. The solvent was depressurized and concentrated and then dissolved in 10 mL of pyridine and 0.095 mL (1.5 eq.) of anhydrous acetic acid was added thereto with stirring at room temperature for 4 hours. This reaction solution was depressurized and concentrated, and dissolved in 10 mL of a 98% TFA-methylene chloride solution and reacted at 0° C. for 2 hours. The solvent was depressurized and concentrated and then dissolved in 20 mL of MeOH—$H_2O$ (9:1), and then, NaOH (5 eq.) was added thereto with stirring at room temperature for 24 hours. The reaction solution was acidified with 2 mL of a 20% HCl solution and concentrated by using a lyophilizer and then separated by a silica gel chromatography using MeOH—CH$_2$Cl$_2$ (1:1). As a result, 275 mg of the compound corresponding to Entry 46 was obtained.

6. Producing Method of Selenophene-Fused Aromatic Compounds Corresponding to Entry 47 to Entry 49

In the present Example, a producing process of selenophene-fused aromatic compounds corresponding to Entry 47 to Entry 49 was as shown in the following scheme.

solution and concentrated by using a lyophilizer and then separated by a silica gel chromatography using MeOH—CH$_2$Cl$_2$ (1:4). As a result, 153 mg of the compound corresponding to Entry 47 was obtained at a yield of 93%.

In order to synthesize the selenophene-fused aromatic compound corresponding to Entry 48, 167 mg of an intermediate was obtained at a yield of 77% by performing a reaction similar to the synthesis of the compound corresponding to Entry 47 by using 231 mg of a 6-methoxy benzoselenophene derivative and 864 mg (2.5 eq.) of tetrabutyl ammonium

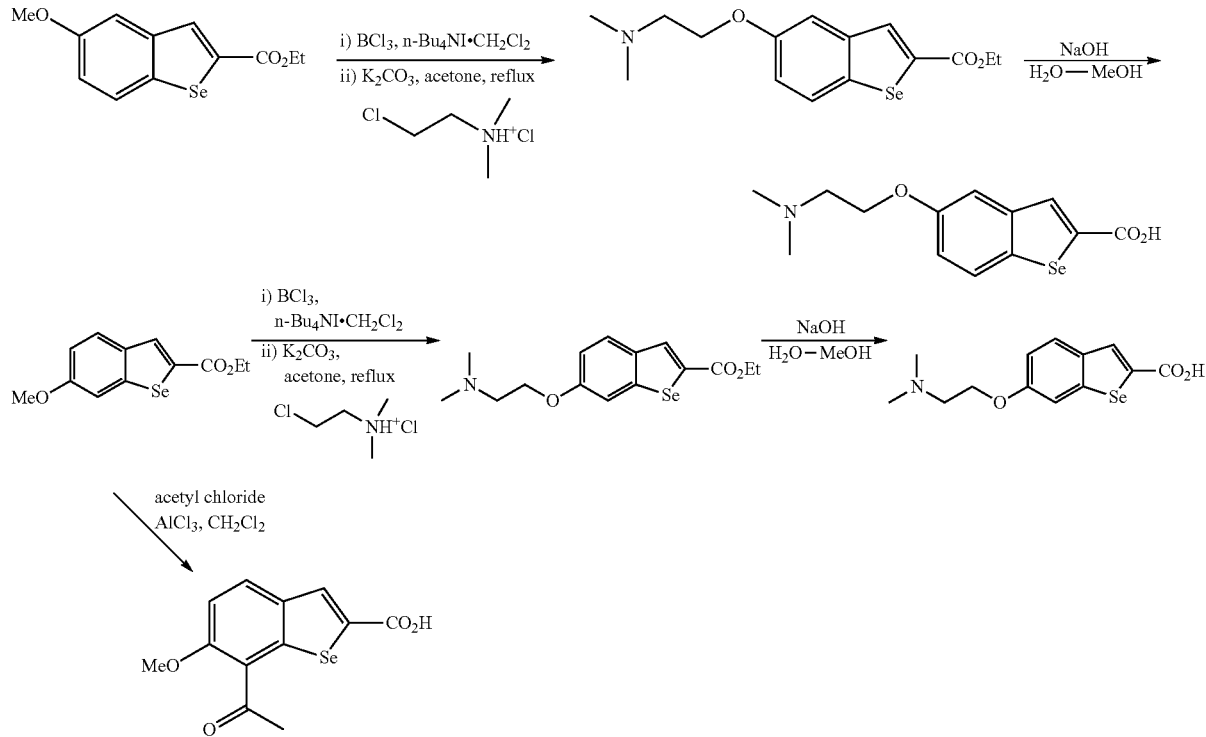

[Scheme 10] Entry 47 to Entry 49

Producing Method:

In order to synthesize the selenophene-fused aromatic compound corresponding to Entry 47, 770 mg of a 5-methoxy benzoselenophene derivative and 2.65 g (2.5 eq.) of tetrabutyl ammonium iodide were dissolved in 10 mL of anhydrous methylene chloride, and nitrogen was added thereto with stirring at −78° C. for 2 minutes. 7.7 mL of BCl$_3$ (1 M methylene chloride solution, 2.5 eq.) was added to this solution and then, reacted at 0° C. for 2 hours. 20 mL of ice water was added to this solution and then extracted 3 times by using 200 mL of methylene chloride. Then, an organic solvent layer was depressurized and concentrated and then dissolved in 50 mL of acetone. 988 mg (3 eq.) of N,N-dimethylethylamine and 2.13 g (5 eq.) of potassium carbonate were added to this solution with stirring at 65° C. for 7 hours. This solution was depressurized and concentrated and then extracted 3 times by using 200 mL of methylene chloride. An organic layer was concentrated and separated by silica gel chromatography using EA-hex (1:1), and 472 mg of an intermediate was obtained at a yield of 43%. 160 mg of this intermediate was dissolved in 20 mL of MeOH—H$_2$O (9:1), and NaOH (5 eq.) was added with stirring at room temperature for 24 hours. The reaction solution was acidified with 2 mL of a 20% HCl iodide. 160 mg of this intermediate was hydrolyzed in a similar manner to the synthesis of the compound corresponding to Entry 47 and refined. As a result, 148 mg of the compound corresponding to Entry 48 was obtained at a yield of 90%.

In order to synthesize the selenophene-fused aromatic compound corresponding to Entry 49, 50 mg of a 6-methoxy benzoselenophene derivative was dissolved in 10 mL of anhydrous methylene chloride, and 94 mg (4 eq.) of aluminum chloride and 0.037 mL (3 eq.) of acetyl chloride were added thereto with stirring for 3 hours. Water was added to the reaction solution, and the reaction product was extracted 3 times by using 200 mL of methylene chloride. An organic layer was concentrated and separated by silica gel chromatography using EA-hex (1:4). As a result, 8.7 mg of the compound corresponding to Entry 49 was obtained.

7. Producing Method of Selenophene-Fused Aromatic Compounds Corresponding to Entry 50 to Entry 58

In the present Example, a producing process of selenophene-fused aromatic compounds corresponding to Entry 50 to Entry 58 was as shown in the following scheme.

[Scheme 11] Entry 50 to Entry 58

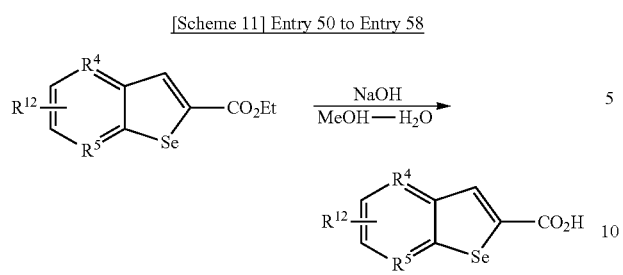

Producing Method:

General producing method by hydrolysis of benzoselenophene ethylester derivative An ethylester derivative was dissolved in 20 mL of MeOH—H$_2$O (9:1), and NaOH (5 eq.) was added thereto with stirring at room temperature for 24 hours. After the reaction was finished, MeOH was depressurized and concentrated and 20 mL of water was added. The reaction solution was adjusted to be acidic by adding 2 mL of a 20% HCl solution. A solid produced was filtered and separated by silica gel chromatography using MeOH—CH$_2$Cl$_2$ (1:4). As a result, the compounds corresponding to Entry 50 to Entry 58 were obtained at a yield in a range of from 49% to 98%.

8. Selenophene-Fused Aromatic Compound Produced in Accordance with Example

[Table 1] below shows aromatic starting materials and diselenide compounds used herein for producing a selenophene-fused aromatic compound in accordance with the second aspect and yields (%) of the selenophene-fused aromatic compound depending thereon:

TABLE 1

| Entry (example) | Aromatic starting material | Diselenide compound | Selenophene-fused aromatic compound | Yield (%) |
|---|---|---|---|---|
| | | Selenophene-fused aromatic compound produced in accordance with the second aspect | | |
| 1 | O$_2$N-C$_6$H$_3$(Cl)-CHO | (SeCH$_2$COOEt)$_2$ | O$_2$N-benzoselenophene-CO$_2$Et | 94 |
| 2 | | (p-NO$_2$PhCH$_2$Se)$_2$ | O$_2$N-benzoselenophene-C$_6$H$_4$-NO$_2$ | 85 |
| 3 | | (p-CNPhCH$_2$Se)$_2$ | O$_2$N-benzoselenophene-C$_6$H$_4$-CN | 65 |
| 4 | | (p-EtO$_2$CPhCH$_2$Se)$_2$ | O$_2$N-benzoselenophene-C$_6$H$_4$-CO$_2$Et | 31 |
| 5 | F$_3$C-C$_6$H$_3$(Cl)-CHO | (SeCH$_2$COOEt)$_2$ | F$_3$C-benzoselenophene-CO$_2$Et | 67 |
| 6 | | (p-NO$_2$PhCH$_2$Se)$_2$ | F$_3$C-benzoselenophene-C$_6$H$_4$-NO$_2$ | 50 |
| 7 | | (p-CNPhCH$_2$Se)$_2$ | F$_3$C-benzoselenophene-C$_6$H$_4$-CN | 83 |
| 8 | NO$_2$-C$_6$H$_3$(Cl)-CHO | (SeCH$_2$COOEt)$_2$ | NO$_2$-benzoselenophene-CO$_2$Et | 98 |

TABLE 1-continued

Selenophene-fused aromatic compound
produced in accordance with the second aspect

| Entry (example) | Aromatic starting material | Diselenide compound | Selenophene-fused aromatic compound | Yield (%) |
|---|---|---|---|---|
| 9 | | (p-NO₂PhCH₂Se)₂ | 4-NO₂-benzo[b]selenophene-2-yl-(4-nitrophenyl) | 65 |
| 10 | | (p-CNPhCH₂Se)₂ | 4-NO₂-benzo[b]selenophene-2-yl-(4-cyanophenyl) | 63 |
| 11 | | (p-EtO₂CPhCH₂Se)₂ | 4-NO₂-benzo[b]selenophene-2-yl-(4-CO₂Et-phenyl) | 62 |
| 12 | 4-O₂N, 2-Cl, CN benzene | (SeCH₂COOEt)₂ | 5-NO₂-3-NH₂-benzo[b]selenophene-2-CO₂Et | 71 |
| 13 | | (p-NO₂PhCH₂Se)₂ | 5-NO₂-3-NH₂-2-(4-nitrophenyl)-benzo[b]selenophene | 68 |
| 14 | 4-O₂N, 2-Cl, COPh benzene | (SeCH₂COOEt)₂ | 5-NO₂-3-Ph-benzo[b]selenophene-2-CO₂Et | 70 |
| 15 | | (p-NO₂PhCH₂Se)₂ | 5-NO₂-3-Ph-2-(4-nitrophenyl)-benzo[b]selenophene | 69 |
| 16 | 4-O₂N, 2-Cl, CO₂CH₃ benzene | (SeCH₂COOEt)₂ | 5-NO₂-3-OH-benzo[b]selenophene-2-CO₂Et | 62 |
| 17 | | (p-NO₂PhCH₂Se)₂ | 5-NO₂-3-OH-2-(4-nitrophenyl)-benzo[b]selenophene | 60 |
| 18 | 2,6-difluoro-CHO benzene | (SeCH₂COOEt)₂ | 4-F-benzo[b]selenophene-2-CO₂Et | 80 |

TABLE 1-continued

Selenophene-fused aromatic compound produced in accordance with the second aspect

| Entry (example) | Aromatic starting material | Diselenide compound | Selenophene-fused aromatic compound | Yield (%) |
|---|---|---|---|---|
| 19 | 5-Br, 2-F benzaldehyde (Br—C₆H₃(F)—CHO) | $(SeCH_2COOEt)_2$ | 5-Br-benzo[b]selenophene-2-CO₂Et | 31 |
| 20 | 2-Cl-pyridine-3-carbaldehyde | $(p\text{-}NO_2PhCH_2Se)_2$ | 2-(4-nitrophenyl)selenopheno[2,3-b]pyridine | 59 |

The selenophene-fused aromatic compound corresponding to Entry 17 among the selenophene-fused aromatic compounds shown in [Table 1] exhibited a solvatochromic property. When a concentration of the compound corresponding to Entry 17 is 60.4 μM, an absorption spectrum was as shown in FIG. 4.

Further, [Table 2] below shows aromatic starting materials and $R^{11}CH_2X$ used herein for producing a selenophene-fused aromatic compound in accordance with the third aspect and yields (%) of the selenophene-fused aromatic compound depending thereon. In [Table 2], Yield 1 represents a yield of a reaction intermediate, and Yield 2 represents a yield of a selenophene-fused aromatic compound as a reaction product:

TABLE 2

Selenophene-fused aromatic compound produced in accordance with the third aspect

| Entry (example) | Aromatic starting material | $R^1CH_2X$ | Yield 1 (%) | Selenophene-fused aromatic compound | Yield 2 (%) |
|---|---|---|---|---|---|
| 21 | 4-H₃CO, 2-SeMe benzaldehyde | $BrCH_2COOEt$ | 77 | 5-H₃CO-benzo[b]selenophene-2-CO₂Et | 68 |
| 22 | (same) | $O_2N\text{-}C_6H_4\text{-}CH_2Cl$ | 79 | 5-H₃CO-2-(4-nitrophenyl)benzo[b]selenophene | 72 |
| 23 | 2-SeMe, 3-OCH₃ benzaldehyde | $BrCH_2COOEt$ | 63 | 7-OCH₃-benzo[b]selenophene-2-CO₂Et | 79 |
| 24 | 4-H₃CO, 2-SeMe benzaldehyde | $BrCH_2COOEt$ | 95 | 6-H₃CO-benzo[b]selenophene-2-CO₂Et | 86 |
| 25 | (same) | $O_2N\text{-}C_6H_4\text{-}CH_2Cl$ | 72 | 6-H₃CO-2-(4-nitrophenyl)benzo[b]selenophene | 72 |
| 26 | (same) | $NC\text{-}C_6H_4\text{-}CH_2Cl$ | 60 | 6-H₃CO-2-(4-cyanophenyl)benzo[b]selenophene | 92 |

TABLE 2-continued

Selenophene-fused aromatic compound produced in accordance with the third aspect

| Entry (example) | Aromatic starting material | R¹CH₂X | Yield 1 (%) | Selenophene-fused aromatic compound | Yield 2 (%) |
|---|---|---|---|---|---|
| 27 | | 4-(EtO₂C)C₆H₄CH₂Cl | 94 | 6-methoxy-2-(4-ethoxycarbonylphenyl)benzo[b]selenophene | 91 |
| 28 | 4,5-dimethoxy-2-(methylselanyl)benzaldehyde | BrCH₂COOEt | 86 | 5,6-dimethoxy-2-(4-ethoxycarbonylphenyl)benzo[b]selenophene | 87 |
| 29 | | 4-ClC₆H₄CH₂Br | 65 | 5,6-dimethoxy-2-(4-chlorophenyl)benzo[b]selenophene | 50 |
| 30 | | 4-O₂NC₆H₄CH₂Cl | 69 | 5,6-dimethoxy-2-(4-nitrophenyl)benzo[b]selenophene | 54 |
| 31 | 6-(methylselanyl)benzo[d][1,3]dioxole-5-carbaldehyde | BrCH₂COOEt | 77 | ethyl [1,3]dioxolo-benzoselenophene-6-carboxylate | 86 |
| 32 | | 4-NCC₆H₄CH₂Cl | 64 | 2-(4-cyanophenyl)-[1,3]dioxolo-benzoselenophene | 68 |
| 33 | | 4-(EtO₂C)C₆H₄CH₂Cl | 94 | 2-(4-ethoxycarbonylphenyl)-[1,3]dioxolo-benzoselenophene | 77 |
| 34 | 2-(methylselanyl)nicotinaldehyde | BrCH₂COOEt | 88 | ethyl selenopheno[2,3-b]pyridine-2-carboxylate | 97 |
| 35 | | 4-O₂NC₆H₄CH₂Cl | 84 | 2-(4-nitrophenyl)selenopheno[2,3-b]pyridine | 91 |
| 36 | 3-(methylselanyl)furan-2-carbaldehyde | BrCH₂COOEt | 90 | ethyl selenopheno[2,3-b]furan-2-carboxylate | 73 |
| 37 | 3-(methylselanyl)thiophene-2-carbaldehyde | BrCH₂COOEt | 98 | ethyl selenopheno[2,3-b]thiophene-2-carboxylate | 95 |

The selenophene-fused aromatic compounds corresponding to Entry 26, Entry 27, and Entry 30 among the selenophene-fused aromatic compounds shown in [Table 2] exhibited a fluorescent property. Spectra showing a fluorescent property of the compounds were as shown in FIG. 1 to FIG. 3.

Further, [Table 3] below shows selenophene-fused aromatic compounds produced by performing an additional reaction to the selenophene-fused aromatic compounds corresponding to Entry 1 to Entry 37 and produced in accordance with the second aspect or the third aspect:

TABLE 3

<Selenophene-fused aromatic compounds produced by performing an additional reaction to selenophene-fused aromatic compounds corresponding to Entry 1 to Entry 37>

| Entry (example) | Selenophene-fused aromatic compound |
| --- | --- |
| 38 | $H_2N$-benzo[b]selenophene-2-$CO_2Et$ |
| 39 | AcHN-benzo[b]selenophene-2-$CO_2H$ |
| 40 | butyramide-benzo[b]selenophene-2-$CO_2H$ |
| 41 | hexanamide-benzo[b]selenophene-2-$CO_2H$ |
| 42 | butyl-urea-benzo[b]selenophene-2-$CO_2H$ |
| 43 | 4-fluorophenyl-urea-benzo[b]selenophene-2-$CO_2H$ |
| 44 | N,N-dimethylglycinamide-benzo[b]selenophene-2-$CO_2H$ |
| 45 | AcHN-lysine(NHAc)-amide-benzo[b]selenophene-2-$CO_2H$ |
| 46 | arginine(NHAc)-amide-benzo[b]selenophene-2-$CO_2H$ |
| 47 | (dimethylamino)ethoxy-benzo[b]selenophene-2-$CO_2H$ |
| 48 | (dimethylamino)ethoxy-benzo[b]selenophene-2-$CO_2H$ (isomer) |
| 49 | HO, acetyl-benzo[b]selenophene-2-$CO_2Et$ |
| 50 | methoxy-benzo[b]selenophene-2-$CO_2H$ |
| 51 | methoxy-benzo[b]selenophene-2-$CO_2H$ (isomer) |
| 52 | dimethoxy-benzo[b]selenophene-2-$CO_2H$ |
| 53 | methylenedioxy-benzo[b]selenophene-2-$CO_2H$ |
| 54 | pyrido-selenophene-2-$CO_2H$ |
| 55 | furo-selenophene-2-$CO_2H$ |
| 56 | thieno-selenophene-2-$CO_2H$ |
| 57 | methoxy-benzo[b]selenophene-2-$CO_2H$ |

TABLE 3-continued

<Selenophene-fused aromatic compounds produced by performing an additional reaction to selenophene-fused aromatic compounds corresponding to Entry 1 to Entry 37>

| Entry (example) | Selenophene-fused aromatic compound |
|---|---|
| 58 | $O_2N$-benzo[b]selenophene-2-$CO_2H$ |

<$^1$H NMR and $^{13}$C NMR data of selenophene-fused aromatic compounds corresponding to Entry 1 to Entry 58 shown in [Table 1] to [Table 3]>

[Entry 1] 5-Nitro-benzo[b]selenophene-2-carboxylic acid ethyl ester:
$^1$H NMR (500.1 MHz, CDCl$_3$) ∂ 1.42 (t, 3H), 4.42 (q, 2H), 8.04 (d, 1H, J=9), 8.21 (dd, 1H, J=8.5, 2), 8.38 (s, 1H), 8.74 (d, 1H, J=2); $^{13}$C NMR (125.7 MHz, CDCl$_3$) ∂; LCMS (ESI); m/z calcd for C$_9$H$_{11}$NO$_4$Se [M$^+$]: 298.97. found: 300.2.

[Entry 2] 5-Nitro-2-(4-nitro-phenyl)-benzo[b]selenophene:
$^1$H NMR (500.1 MHz, CDCl$_3$) ∂ 8.02 (d, 2H, J=9), 8.15 (dd, 1H, J=8.5, 2), 8.33 (d, 2H, J=9), 8.44 (d, 1H, J=9), 8.50 (s, 1H), 8.79 (d, 1H, J=2.5); $^{13}$C NMR (125.7 MHz, CDCl$_3$) ∂; 119.05, 120.97, 124.54, 126.92, 127.31, 127.72, 140.89, 142.80, 145.79, 147.22, 148.03, 148.55.

[Entry 3] 4-(5-Nitro-benzo[b]selenophen-2-yl)-benzonitrile:
$^1$H NMR (500.1 MHz, CDCl$_3$) ∂ 1.39 (t, 3H, J=7.0), 3.87 (s, 3H), 4.36 (q, 2H, J=2.5, 8.5), 6.99 (dd, 1H, J=2.5, 9.0), 7.36 (d, 1H, J=1.5), 7.74 (d, 1H, J=8.5), 8.19 (s, 1H); $^{13}$C NMR (125.7 MHz, CDCl$_3$) ∂ 12.60, 53.80, 59.68, 106.49, 113.37, 126.30, 131.53, 132.27, 133.30, 144.16, 157.47, 162.24.

[Entry 4] 4-(5-Nitro-benzo[b]selenophen-2-yl)-benzoic acid ethyl ester:
$^1$H NMR (500.1 MHz, CDCl$_3$) ∂ 3.90 (s, 3H), 7.01 (dd, 1H, J=2.0, 8.5), 7.40 (d, 1H, J=2.0), 7.71-7.72 (m, 3H), 7.80 (s, 1H), 8.24-8.26 (m, 2H); $^{13}$C NMR (125.7 MHz, CDCl$_3$) ∂ 54.54, 107.69, 114.44, 123.33, 124.99, 125.10, 126.08, 132.44, 141.53, 142.73, 144.59, 146.13, 157.23.

[Entry 5] 5-Trifluoromethyl-benzo[b]selenophene-2-carboxylic acid ethyl ester:
$^1$H NMR (500.1 MHz, CDCl$_3$) ∂ 1.42 (t, 3H), 4.41 (q, 2H), 7.58 (dd, 1H, J=8, 1.5), 8.02 (t, 1H), 8.14 (s, 1H), 8.33 (s, 1H); $^{13}$C NMR (125.7 MHz, CDCl$_3$) ∂ 13.28, 60.98, 121.77, 121.80, 123.24, 123.28, 125.50, 132.64, 138.05, 139.90, 146.32, 162.37; LCMS (ESI); m/z calcd for C$_{12}$H$_9$F$_3$O$_2$Se [M$^+$]: 321.97. found: 323.2.

[Entry 6] 2-(4-Nitro-phenyl)-5-trifluoromethyl-benzo[b]selenophene:
$^1$H NMR (500.1 MHz, CDCl$_3$) ∂ 7.54 (d, 1H, J=8.5), 7.77 (d, 2H, J=8.5), 7.91 (s, 1H), 8.01 (d, 1H, J=8.0), 8.09 (s, 1H), 8.29 (d, 2H, J=7.5); $^{13}$C NMR (125.7 MHz, CDCl$_3$) ∂ 119.67, 119.70, 119.73, 119.76, 120.93, 120.96, 120.14, 121.03, 121.35, 122.54, 123.51, 123.72, 124.14, 125.53, 126.06, 126.31, 139.78, 140.53, 143.26, 144.93, 145.67.

[Entry 7] 4-(5-Trifluoromethyl-benzo[b]selenophen-2-yl)-benzonitrile:
$^1$H NMR (500.1 MHz, CDCl$_3$) ∂ 7.51 (d, 1H, J=8.0), 7.69 (s, 4H), 7.83 (s, 1H), 7.97 (d, 1H, J=8.0), 8.05 (s, 1H); $^{13}$C NMR (125.7 MHz, CDCl$_3$) ∂ 112.06, 118.49, 121.18, 121.44, 121.47, 121.49, 121.53, 122.72, 122.76, 122.79, 122.82, 123.34, 125.05, 125.50, 126.04, 127.33, 127.60, 127.67, 127.86, 128.12, 128.38, 132.85, 139.79, 142.49, 144.97, 147.42.

[Entry 8] 4-Nitro-benzo[b]selenophene-2-carboxylic acid ethyl ester:
$^1$H NMR (500.1 MHz, CDCl$_3$) ∂ 1.41 (t, 3H), 4.40 (q, 2H), 7.28 (t, 1H), 7.38 (d, 1H, J=8), 7.76 (d, 1H, J=8), 8.47 (s, 1H); $^{13}$C NMR (125.7 MHz, CDCl$_3$) ∂ 14.44, 62.01, 124.42, 125.29, 127.56, 132.10, 132.35, 137.76, 139.61, 145.08, 163.66.

[Entry 9] 4-Nitro-2-(4-nitro-phenyl)-benzo[b]selenophene:
$^1$H NMR (500.1 MHz, CDCl$_3$) ∂ 7.40 (d, 1H, J=8), 7.79 (t, 3H), 8.09 (s, 1H), 8.29 (d, 2H, J=8.5); $^{13}$C NMR (125.7 MHz, CDCl$_3$) ∂ 123.97, 124.15, 124.45, 125.43, 126.23, 127.44, 130.98, 140.87, 142.01, 142.68, 145.51, 147.47.

[Entry 10] 4-(6-Nitro-benzo[b]selenophen-2-yl)-benzonitrile:
$^1$H NMR (500.1 MHz, CDCl$_3$) ∂ 7.23 (t, 1H, J=8.0), 7.38 (d, 1H, J=7.5), 7.67 (d, 2H, J=8.0), 7.71 (d, 2H, J=8.5), 7.75 (d, 1H, J=8.0), 8.01 (s, 1H); $^{13}$C NMR (125.7 MHz, CDCl$_3$) ∂ 111.87, 118.61, 123.52, 123.99, 125.40, 126.13, 127.34, 130.83, 132.81, 140.08, 140.87, 142.49, 146.12.

[Entry 11] 4-(6-Nitro-benzo[b]selenophen-2-yl)-benzoic acid ethyl ester:
$^1$H NMR (500.1 MHz, CDCl$_3$) ∂ 1.42 (t, 3H, J=7.0), 4.41 (q, 2H, J=7.0), 7.20 (t, 1H, J=7.5), 7.36 (d, 1H, J=8.0), 7.70 (d, 2H, J=8.0), 7.75 (d, 1H, J=8.0), 8.02 (s, 1H), 8.08 (d, 2H, J=8.0); $^{13}$C NMR (125.7 MHz, CDCl$_3$) ∂ 13.17 59.97 121.43 122.72 123.98 124.46 125.52 129.09 129.11 129.35 138.67 139.82 141.09 146.21 164.91.

[Entry 12] 3-Amino-5-nitro-benzo[b]selenophene-2-carboxylic acid ethyl ester:
$^1$H NMR (500.1 MHz, CDCl$_3$) ∂ 1.39 (t, 3H), 4.36 (q, 2H), 6.12 (bs, 2H, NH), 7.94 (d, 1H, J=8.5), 8.25 (dd, 1H, J=9, 2), 8.53 (d, 1H, J=2.5); $^{13}$C NMR (125.7 MHz, acetone-D6) ∂ 14.81, 61.21, 98.63, 120.45, 122.67, 128.53, 135.97, 146.77, 147.81, 152.15, 166.52.

[Entry 13] 5-Nitro-2-(4-nitro-phenyl)-benzo[b]selenophen-3-ylamine:
$^1$H NMR (500.1 MHz, CDCl$_3$) ∂ 7.89-7.92 (m, 2H), 8.20 (dd, 1H, J=8.5, 2), 8.27 (d, 2H, J=8.5), 8.30-8.32 (m, 2H), 8.86 (d, 1H, J=2); $^{13}$C NMR (125.7 MHz, CDCl$_3$) ∂ 111.84, 117.90, 118.90, 123.63, 126.24, 128.10, 136.81, 139.38, 142.36, 145.03, 145.07, 145.44.

[Entry 14] 5-Nitro-3-phenyl-benzo[b]selenophene-2-carboxylic acid ethyl ester:
$^1$H NMR (500.1 MHz, CDCl$_3$) ∂ 1.66 (t, 3H), 4.21 (q, 2H), 7.34 (dd, 2H, J=6.5, 4), 7.51-7.53 (m, 3H), 8.06 (d, 1H, J=8.5), 8.24 (dd, 1H, J=9, 2.5), 8.30 (d, 1H, J=2.5); $^{13}$C NMR (125.7 MHz, CDCl$_3$) ∂ 11.64, 59.63, 118.68, 120.66, 124.17, 126.21, 126.46, 127.09, 132.45, 133.00, 141.00, 143.00, 143.21, 144.00, 161.00; LCMS (ESI); m/z calcd for C$_{17}$H$_{13}$NO$_4$Se [M$^+$]: 375.00. found: 376.2.

[Entry 15] 5-Nitro-2-(4-nitro-phenyl)-3-phenyl-benzo[b]selenophene:
$^1$H NMR (500.1 MHz, CDCl$_3$) ∂ 7.60 (t, 2H), 7.72 (t, 1H), 7.82 (d, 2H, J=7.5), 8.15-8.21 (m, 2H), 8.54 (d, 1H, J=2.5); $^{13}$C NMR (125.7 MHz, CDCl$_3$) ∂ 125.20, 126.08, 127.89, 129.01, 131.74, 132.57, 134.91, 135.26, 143.55, 145.07, 194.34.

[Entry 16] 3-Hydroxy-5-nitro-benzo[b]selenophene-2-carboxylic acid ethyl ester:
$^1$H NMR (500.1 MHz, CDCl$_3$) ∂ 1.42 (t, 3H), 4.43 (q, 2H), 7.95 (d, 1H, J=9), 8.28 (dd, 1H, J=8.5, 2), 8.82 (d, 1H, J=2.5), 10.47 (bs, 1H, OH); $^{13}$C NMR (125.7 MHz, CDCl$_3$) ∂ 13.42, 60.95, 119.51, 121.49, 126.06, 132.55, 144.30, 144.92, 159.63, 166.74; LCMS (ESI); m/z calcd for $C_{11}H_3NO_5Se$ [M$^+$]: 314.96. found: 316.3.

[Entry 17] 5-Nitro-2-(4-nitro-phenyl)-benzo[b]selenophen-3-ol:

$^1$H NMR (500.1 MHz, CDCl$_3$) ∂ 8.11 (d, 1H, J=2), 8.13 (d, 1H, J=2), 8.20 (dd, 1H, J=8, 2), 8.28 (d, 1H, J=2), 8.3 (d, 1H, J=2), 8.86 (d, 1H, J=2); $^{13}$C NMR (125.7 MHz, CDCl$_3$) ∂ 119.35, 120.82, 121.21, 124.80, 128.11, 129.68, 137.76, 142.24, 144.26, 147.14, 147.17, 148.92.

[Entry 18] 4-Fluoro-benzo[b]selenophene-2-carboxylic acid ethyl ester:

$^1$H NMR (500.1 MHz, CDCl$_3$) ∂ 1.42 (t, 3H, J=7), 4.40 (q, 2H, J=7.0), 7.06 (dd, 1H, J=8, 10), 7.36 (td, 1H, J=5.5, 8), 7.66 (d, 1H, J=8), 8.41 (s, 1H); $^{13}$C NMR (125.7 MHz, CDCl$_3$) ∂ 14.32, 61.87, 110.09, 110.24, 121.60, 121.63, 128.02, 128.08, 128.57, 130.59, 130.73, 137.25, 145.80, 145.84, 158.98, 161.02, 163.53.

[Entry 19] 5-Bromo-benzo[b]selenophene-2-carboxylic acid ethyl ester:

$^1$H NMR (500.1 MHz, CDCl$_3$) ∂ 1.41 (t, 3H, J=7.5), 4.39 (q, 2H, J=7.5), 7.46 (dd, 1H, J=2.0, 8.5), 7.75 (d, 1H, J=8.5), 8.01 (d, 1H, J=1.5), 8.19 (s, 1H); $^{13}$C NMR (125.7 MHz, CDCl$_3$) ∂ 12.31, 59.89, 117.17, 125.21, 127.80, 127.84, 130.97, 136.56, 140.41, 140.84, 161.48.

[Entry 20] 2-(4-Nitrophenyl)-seleno[2,3-b]pyridine:

$^1$H NMR (500.1 MHz, CDCl$_3$) ∂ 7.36 (dd, 1H, J=4.5, 8.0), 7.76 (s, 1H), 7.79 (d, 2H, J=8.5), 8.06 (dd, 1H, J=1.5, 8.0), 8.30 (d, 2H, J=8.5), 8.54 (dd, 1H, J=1.5, 4.5); $^{13}$C NMR (125.7 MHz, CDCl$_3$) ∂ 118.68, 121.26, 122.61, 125.66, 131.05, 135.37, 140.28, 143.85, 145.29, 145.75, 163.59.

[Entry 21] 5-Methoxy-benzo[b]selenophene-2-carboxylic acid ethyl ester:

$^1$H NMR (500.1 MHz, CDCl$_3$) ∂ 1.39 (t, 3H), 3.84 (s, 3H), 4.37 (q, 2H), 7.02 (dd, 1H, J=8.5, 2.5), 7.31 (d, 1H, J=2), 7.72 (d, 1H, J=8.5), 8.20 (s, 1H); $^{13}$C NMR (125.7 MHz, CDCl$_3$) ∂ 12.04, 53.18, 59.29, 106.95, 114.95, 124.14, 131.72, 133.56, 135.27, 139.88, 155.72, 161.56; LCMS (ESI); m/z calcd for $C_{12}H_{12}O_3Se$ [M$^+$]: 284.00. found: 285.2.

[Entry 22] 5-Methoxy-2-(4-nitro-phenyl)-benzo[b]selenophene:

$^1$H NMR (500.1 MHz, CDCl$_3$) ∂ 3.88 (s, 3H), 6.97 (d, 1H, J=9), 7.31 (s, 1H), 7.74 (d, 3H, J=9), 7.80 (s, 1H), 8.26 (d, 2H, J=8.5); $^{13}$C NMR (125.7 MHz, CDCl$_3$) ∂ 54.54, 107.69, 114.44, 123.33, 124.99, 125.10, 126.08, 132.44, 141.53, 142.73, 144.59, 146.13, 157.23.

[Entry 23] 7-Methoxy-benzo[b]selenophene-2-carboxylic acid ethyl ester:

$^1$H NMR (500.1 MHz, CDCl$_3$) ∂ 1.40 (t, 3H), 3.99 (s, 3H), 4.38 (q, 2H), 6.81 (d, 1H, J=8), 7.37 (t, 1H), 7.50 (d, 1H, J=7.5), 8.29 (s, 1H); $^{13}$C NMR (125.7 MHz, CDCl$_3$) ∂ 14.61, 56.03, 61.89, 106.39, 120.06, 126.87, 133.38, 134.78, 137.21, 142.89, 156.51, 164.34.

[Entry 24] 6-Methoxy-benzo[b]selenophene-2-carboxylic acid ethyl ester:

$^1$H NMR (500.1 MHz, CDCl$_3$) ∂ 1.39 (t, 3H), 3.86 (s, 3H), 4.36 (q, 2H), 6.99 (dd, 1H, J=9, 2.5), 7.35 (d, 1H, J=1.5), 7.74 (d, 1H, J=8.5), 8.18 (s, 1H); $^{13}$C NMR (125.7 MHz, CDCl$_3$) ∂ 12.60, 53.80, 59.68, 106.49, 113.37, 126.30, 131.53, 132.27, 133.30, 144.16, 157.47, 162.24.

[Entry 25] 6-Methoxy-2-(4-nitro-phenyl)-benzo[b]selenophene:

$^1$H NMR (500.1 MHz, CDCl$_3$) ∂ 3.89 (s, 3H), 7.01 (dd, 1H, J=8.5, 2), 7.39 (d, 1H, J=2), 7.70 (d, 1H, J=8.5), 7.72 (d, 2H, J=2.0), 7.80 (s, 1H), 8.24 (s, 1H), 8.25 (d, 1H, J=1.5); $^{13}$C NMR (125.7 MHz, CDCl$_3$) ∂ 54.23, 107.06, 113.42, 122.81, 124.37, 125.21, 135.25, 140.01, 141.27, 141.97, 145.45, 156.91.

[Entry 26] 4-(6-Methoxy-benzo[b]selenophen-2-yl)-benzonitrile:

$^1$H NMR (500.1 MHz, CDCl$_3$) ∂ 3.87 (s, 3H), 6.99 (dd, 1H, J=8.5, 2), 7.37 (d, 1H, J=1.5), 7.63 (s, 4H), 7.67 (d, 1H, J=8.5), 7.71 (s, 1H); $^{13}$C NMR (125.7 MHz, CDCl$_3$) ∂ 55.63, 108.55, 110.76, 114.71, 118.82, 125.08, 126.53, 126.75, 132.67, 136.61, 140.69, 141.86, 143.07, 158.14.

[Entry 27] 4-(6-Methoxy-benzo[b]selenophen-2-yl)-benzoic acid ethyl ester:

$^1$H NMR (500.1 MHz, CDCl$_3$) ∂ 1.41 (t, 3H), 3.87 (s, 3H), 4.39 (q, 2H), 6.97 (dd, 1H, J=8.5, 2), 7.37 (d, 1H, J=1.5), 7.62 (d, 2H, J=8), 7.66 (d, 1H, J=8.5), 7.71 (s, 1H), 8.04 (d, 2H, J=8); $^{13}$C NMR (125.7 MHz, CDCl$_3$) ∂ 12.92, 54.15, 59.58, 107.10, 113.01, 112.76, 124.72, 124.87, 127.97, 128.75, 135.41, 139.07, 141.69, 156.40, 164.77.

[Entry 28] 5,6-Dimethoxy-benzo[b]selenophene-2-carboxylic acid ethyl ester:

$^1$H NMR (500.1 MHz, CDCl$_3$) ∂ 1.39 (t, 3H), 3.93 (s, 3H), 3.96 (s, 3H), 4.36 (q, 2H), 7.27 (s, 1H), 7.31 (s, 1H), 8.17 (s, 1H); $^{13}$C NMR (125.7 MHz, CDCl$_3$) ∂ 14.41, 56.03, 56.17, 61.42, 134.07, 134.18, 134.62, 137.31, 146.66, 150.28, 164.02.

[Entry 29] 2-(4-Chloro-phenyl)-5,6-dimethoxy-benzo[b]selenophene:

$^1$H NMR (500.1 MHz, CDCl$_3$) ∂ 3.94 (s, 3H), 3.95 (s, 3H), 7.21 (s, 1H), 7.30 (s, 1H), 7.34 (d, 2H, J=8), 7.49 (d, 2H, J=8), 7.55 (s, 1H); $^{13}$C NMR (125.7 MHz, CDCl$_3$) ∂ 56.18, 56.31, 107.14, 107.33, 123.34, 127.72, 129.17, 133.35, 133.66, 135.11, 136.54, 144.36, 148.46, 148.57.

[Entry 30] 5,6-Dimethoxy-2-(4-nitro-phenyl)-benzo[b]selenophene:

$^1$H NMR (500.1 MHz, CDCl$_3$) ∂ 3.95 (s, 3H), 3.97 (s, 3H), 7.26 (s, 1H), 7.34 (s, 1H), 7.70 (d, 2H, J=9), 7.77 (s, 1H), 8.24 (d, 2H, J=8.5); $^{13}$C NMR (125.7 MHz, CDCl$_3$) ∂ 56.09, 56.22, 107.06, 107.06, 107.31, 124.40, 125.91, 126.63, 134.51, 136.15, 142.40, 142.73, 146.74, 148.71, 149.13.

[Entry 31] 1,3-Dioxa-5-selena-s-indacene-6-carboxylic acid ethyl ester:

$^1$H NMR (500.1 MHz, CDCl$_3$) ∂ 1.37 (t, 3H), 4.34 (q, 2H), 6.01 (s, 2H), 6.99 (dd, 1H, J=9, 2.5), 7.20 (s, 1H), 7.23 (s, 1H), 8.10 (s, 1H); $^{13}$C NMR (125.7 MHz, CDCl$_3$) ∂ 14.43, 32.31, 60.95, 102.33, 110.00, 113.79, 128.82, 129.37, 129.87, 130.75, 131.23, 142.60, 148.12, 152.89, 166.37, 191.35.

[Entry 32] 4-(1,3-Dioxa-5-selena-s-indacen-6-yl)-benzonitrile:

$^1$H NMR (500.1 MHz, CDCl$_3$) ∂ 6.03 (s, 2H), 7.02 (s, 1H), 7.27 (s, 1H), 7.65 (d, 4H, J=2), 7.69 (s, 1H); $^{13}$C NMR (125.7 MHz, CDCl$_3$) ∂ 99.49, 102.64, 102.79, 108.81, 116.76, 123.11, 124.63, 130.69, 133.04, 134.87, 138.59, 141.12, 145.26, 145.40.

[Entry 33] 4-(1,3-Dioxa-5-selena-s-indacen-6-yl)-benzoic acid ethyl ester:

$^1$H NMR (500.1 MHz, CDCl$_3$) ∂ 1.41 (t, 3H), 4.39 (q, 2H), 6.02 (s, 2H), 7.18 (s, 1H), 7.27 (s, 1H), 7.60 (s, 1H), 7.61 (d, 1H, J=1.5), 7.67 (s, 1H), 8.03 (s, 1H), 8.04 (d, 1H, J=2); $^{13}$C NMR (125.7 MHz, CDCl$_3$) ∂ 14.27, 60.96, 101.31, 104.46, 104.74, 124.25, 125.97, 129.36, 130.15, 134.61, 137.00, 140.34, 144.36, 147.00, 147.03, 166.15.

[Entry 34] Selenolo[2,3-b]pyridine-2-carboxylic acid ethyl ester:

$^1$H NMR (500.1 MHz, CDCl$_3$) ∂ 1.39 (t, 3H, J=7.0), 4.38 (q, 2H, J=7.0), 7.33 (dd, 1H, J=4.5, 8.0), 8.09 (d, 1H, J=2.0, 8.0), 8.16 (s, 1H), 8.58 (dd, 1H, J=1.5, 4.5); $^{13}$C NMR (125.7

MHz, CDCl₃) ∂ 14.31, 61.94, 120.29, 131.34, 134.39, 135.63, 137.47, 148.62, 163.62, 166.95.

[Entry 35] 2-(4-Nitro-phenyl)-selenolo[2,3-b]pyridine:
¹H NMR (500.1 MHz, CDCl₃) ∂ 7.35 (dd, 1H, J=5.0, 7.5), 7.75 (s, 1H), 7.78 (d, 1H, J=8.0), 8.05 (d, 1H, J=7.5), 8.28 (d, 1H, J=8.0); ¹³C NMR (125.7 MHz, CDCl₃) ∂ 118.68, 121.26, 122.61, 125.66, 131.05, 135.37, 140.28, 143.85, 145.29, 145.75, 163.59.

[Entry 36] Selenolo[3,2-b]furan-5-carboxylic acid ethyl ester:
¹H NMR (500.1 MHz, CDCl₃) ∂ 1.37 (t, 3H, J=7.0), 4.35 (q, 2H, J=7.5), 6.81 (s, 1H), 7.63 (d, 1H, J=1.0), 8.06 (s, 1H); ¹³C NMR (125.7 MHz, CDCl₃) ∂ 14.38 1.40 109.39 119.38 128.64 136.03 147.83 157.43 163.81.

[Entry 37] Selenolo[3,2-b]thiophene-5-carboxylic acid ethyl ester:
¹H NMR (500.1 MHz, CDCl₃) ∂ 1.39 (t, 3H, J=7.0), 4.37 (q, 2H, J=7.0), 7.33 (d, 1H, J=5.5), 7.55 (d, 1H, J=5.0), 8.24 (s, 1H); ¹³C NMR (125.7 MHz, CDCl₃) ∂ 14.39, 61.49, 123.01, 128.30, 131.00, 138.52, 140.18, 143.77, 163.76.

[Entry 38] Ethyl 5-Amino-benzo[b]selenophene-2-carboxylate:
M.P. 78-80° C.; ¹H NMR (500.1 MHz, CDCl₃) ∂ 1.39 (t, 3H), 3.74 (s, 1H), 4.36 (q, 2H), 6.81 (dd, 1H, J=5.7, 3.6), 7.16 (d, 1H, J=1.2), 7.63 (d, 1H, J=5.1), 8.11 (s, 1H); ¹³C NMR (125.7 MHz, CDCl₃) ∂ 14.35, 61.51, 111.78, 117.32, 126.32, 133.65, 136.03, 136.98, 137.34, 142.38, 144.33, 164.09. HRMS (ESI); m/z calcd for C₁₁H₁₁NO₂Se [M⁺]: 269. found: 270.0017 (M+1).

[Entry 39 intermediate] Ethyl-5-Acetamido-benzo[b]selenophene-2-carboxylate:
M.P. 160° C.; ¹H NMR (500.1 MHz, CDCl₃) ∂ 1.40 (t, 3H), 2.22 (s, 3H), 4.38 (q, 2H), 7.40 (d, 1H, J=5.1), 7.81 (d, 1H, J=5.1), 8.20 (s, 1H), 8.23 (s, 1H); ¹³C NMR (125.7 MHz, CDCl₃) ∂ 14.43, 24.75, 61.82, 118.20, 120.02, 126.23, 134.16, 135.56, 137.89, 139.42, 141.90, 163.88, 168.47. HRMS (ESI); m/z calcd for C₁₁H₁₁NO₂Se [M⁺]: 311.0061. found: 312.0114 (M+1).

[Entry 39] 5-Acetamido-benzo[b]selenophene-2-carboxylic acid:
¹H NMR (500.1 MHz, MeOD-d4) ∂ 2.16 (s, 3H), 7.50 (dd, 1H, J=2.0, 8.0), 7.88 (d, 1H, J=8.5), 8.17 (s, 1H), 8.22 (d, 1H, J=2.0); ¹³C NMR (125.7 MHz, MeOD-d4) ∂ 23.83, 119.13, 121.28, 127.20, 134.80, 134.82, 137.70, 140.54, 143.43, 171.79, 175.67.

[Entry 40 intermediate] 5-Butyrylamino-benzo[b]selenophene-2-carboxylic acid ethyl ester:
¹H NMR (500.1 MHz, CDCl₃) ∂ 0.95 (t, 3H, J=7.0), 1.36 (t, 3H, J=7.0), 1.74 (q, 2H, J=7.0), 2.34 (t, 2H, J=7.0), 4.34 (q, 2H, J=7.5), 7.40 (d, 1H, J=8.5), 7.66 (d, 1H, J=8.5), 8.04 (s, 1H), 8.15 (s, 1H), 8.40 (bs, 1H, NH); ¹³C NMR (125.7 MHz, CDCl₃) ∂ 11.92, 12.48, 17.30, 37.56, 59.90, 116.65, 118.71, 124.07, 132.27, 134.02, 135.57, 137.36, 139.77, 162.10, 170.42.

[Entry 40] 5-Butyrylamino-benzo[b]selenophene-2-carboxylic acid:
¹H NMR (500.1 MHz, MeOD-d₄) ∂ 0.96 (t, 3H, J=7.5), 1.69 (q, 2H, J=7.0), 2.33 (t, 2H, J=7.0), 7.42 (d, 1H, J=8.5), 7.77 (d, 1H, J=8.5), 8.07 (s, 1H), 8.16 (s, 1H); ¹³C NMR (125.7 MHz, MeOD-d₄) ∂ 14.11, 20.39, 39.92, 119.10, 121.23, 127.16, 134.86, 137.64, 140.44, 140.88, 143.37, 167.71, 174.72.

[Entry 41 intermediate] 5-Hexanoylamino-benzo[b]selenophene-2-carboxylic acid ethyl ester:
¹H NMR (500.1 MHz, CDCl₃) ∂ 0.87 (s, 3H), 1.32 (s, 4H), 1.38 (t, 3H, J=7.0), 1.72 (s, 2H), 2.36 (t, 2H, J=7.5), 4.36 (q, 2H, J=8.5), 7.41 (d, 1H, J=8.5), 7.72 (d, 1H, J=8.5), 7.95 (s, 1H), 8.12 (s, 1H), 8.18 (s, 1H, NH); ¹³C NMR (125.7 MHz, CDCl₃) ∂ 13.94, 14.33, 22.45, 25.37, 31.47, 37.66, 61.74, 118.27, 120.30, 126.00, 134.14, 135.82, 137.55, 139.20, 141.71, 163.93, 172.09.

[Entry 41] 5-Hexanoylamino-benzo[b]selenophene-2-carboxylic acid:
¹H NMR (500.1 MHz, MeOD-d₄) ∂ 0.94 (t, 3H, J=8.5), 1.38-1.40 (m, 4H), 1.72 (t, 2H, J=7.0), 2.40 (t, 2H, J=7.5), 7.46 (dd, 1H, J=1.5, 8.5), 7.83 (d, 1H, J=9.0), 8.05 (s, 1H), 8.17 (s, 1H); ¹³C NMR (125.7 MHz, MeOD-d₄) ∂ 14.32, 23.51, 26.70, 32.63, 38.04, 118.94, 120.70, 127.04, 132.83, 133.65, 137.38, 140.19, 143.87, 174.87.

[Entry 42 intermediate] 5-(3-Butyl-ureido)-benzo[b]selenophene-2-carboxylic acid ethyl ester:
¹H NMR (500.1 MHz, DMSO) ∂ 8.55 (s, 1H), 8.297 (s, 1H), 8.107 (s, 1H), 7.930 (d, 1H, J=9 Hz), 7.39 (d, 1H, 10.5 Hz), 6.150 (d, 1H, J=5.5 Hz), 4.318 (qr, 2H, J=6.75 Hz), 3.096 (qr, 2H, J=6.5 Hz), 1.425 (t, 2H, J=6.5 Hz), 1.32 (t, 5H, J=7.5 Hz, 0.90 (t, 3H, 7 Hz).

[Entry 42] 5-(3-Butyl-ureido)-benzo[b]selenophene-2-carboxylic acid:
¹H NMR (500.1 MHz, DMSO) ∂ 8.55 (s, 1H), 8.297 (s, 1H), 8.107 (s, 1H), 7.930 (d, 1H, J=9 Hz), 7.39 (d, 1H, 10.5 Hz), 6.150 (d, 1H, J=5.5 Hz), 3.096 (qr, 2H, J=6.5 Hz), 1.425 (t, 2H, J=6.5 Hz), 1.32 (t, 2H, J=7.5 Hz), 0.90 (t, 3H, 7 Hz).

[Entry 43 intermediate] 5-[3-(4-Fluoro-phenyl)-ureido]-benzo[b]selenophene-2-carboxylic acid ethyl ester:
¹H NMR (500.1 MHz, DMSO) ∂ 8.353 (s, 1H), 8.182 (s, 1H), 8.008 (d, 1H, J=8 Hz), 7.494 (t, 3H, J=9 Hz), 7.125 (t, 2H, J=8.5 Hz), 4.327 (qr, 2H, J=7.5 Hz), 1.327 (t, 3H, J=7.0 Hz)

[Entry 43] 5-[3-(4-Fluoro-phenyl)-ureido]-benzo[b]selenophene-2-carboxylic acid:
¹H NMR (500.1 MHz, DMSO) ∂ 8.78 (s, 1H), 8.75 (s, 1H), 8.158 (s, 1H), 7.974 (d, 1H, J=7.5 Hz), 7.480 (m, 4H), 7.132 (d, 2H, J=9.0 Hz)
¹³C NMR (125.7 MHz, ACETONE-d₆) ∂ 23.23, 65.12, 113.26, 113.44, 114.0, 117.14, 118.01, 118.07, 124.42, 134.31, 135.62, 140.13, 150.96

[Entry 44 intermediate] 5-(2-Dimethylamino-acetylamino)-benzo[b]selenophene-2-carboxylic acid ethyl ester:
¹H NMR (500.1 MHz, CDCl₃) ∂ 1.40 (t, 3H, J=7.5), 2.40 (s, 6H), 3.11 (s, 2H), 4.39 (q, 2H, J=7.0), 7.51 (dd, 1H, J=1.5, 8.5), 7.82 (d, 1H, J=9.0), 8.24 (s, 1H), 8.30 (d, 1H, J=1.5), 9.23 (bs, 1H, NH); ¹³C NMR (125.7 MHz, CDCl₃) ∂ 14.34, 46.06, 61.69, 63.67, 117.49, 119.63, 126.13, 134.17, 135.50, 137.67, 139.09, 141.82, 163.82, 168.96.

[Entry 44] 5-(2-Dimethylamino-acetylamino)-benzo[b]selenophene-2-carboxylic acid:
¹H NMR (500.1 MHz, MeOD-d₄) ∂ 2.43 (s, 6H), 3.26 (s, 2H), 7.45 (dd, 1H, J=1.5, 8.5), 7.80 (d, 1H, J=8.5), 8.01 (s, 1H), 8.15 (s, 1H); ¹³C NMR (125.7 MHz, MeOD-d₄) ∂ 45.84, 63.68, 118.90, 120.29, 127.12, 131.69, 136.47, 140.44, 144.10, 148.63, 170.39, 172.00.

[Entry 45 intermediate] 5-[6-tert-Butoxycarbonylamino-2-(9,9a-dihydro-4-aH-fluoren-9-ylmethoxycarbonylamino)-hexanoylamino]-benzo[b]selenophene-2-carboxylic acid ethyl ester:
¹H NMR (500.1 MHz, CDCl₃) ∂ 1.38-1.41 (m, 12H), 1.51 (s, 2H), 1.77 (s, 1H), 1.97-2.04 (m, 2H), 3.06-3.14 (m, 2H), 4.16 (t, 1H, J=7.0), 4.35-4.39 (m, 5H), 4.72 (bs, 1H, NH), 5.91 (bs, 1H, NH), 7.24 (d, 2H, J=6.0), 7.34 (d, 3H, J=7.5), 7.52 (d, 1H, J=7.5), 7.55 (d, 1H, J=7.5), 7.67 (d, 1H, J=8.0), 7.72 (d, 2H, J=7.5), 8.10 (s, 1H), 8.18 (s, 1H), 8.92 (bs, 1H, NH); ¹³C NMR (125.7 MHz, CDCl₃) ∂ 14.36, 22.55, 28.46, 29.53, 31.80, 39.63, 47.08, 55.61, 61.72, 67.35, 79.38, 118.16, 120.03, 120.08, 125.03, 126.04, 127.13, 127.80, 134.12, 135.46, 137.66, 139.44, 141.29, 141.66, 143.61, 143.68, 156.42, 163.84, 170.69.

[Entry 46 intermediate] Fmoc-Arg(Pmc)-benzoselenophene-ester:

$^1$H NMR (500.1 MHz, CDCl$_3$) ∂ 1.25 (s, 6H), 1.38 (t, 3H, J=7.5), 1.72 (t, 2H, J=7.0), 1.74-1.81 (m, 1H), 1.98-2.00 (m, 1H), 2.06 (s, 3H), 2.53 (s, 6H), 2.57 (s, 3H), 3.29-3.39 (m, 2H), 4.11 (t, 1H, J=7.0), 4.34-4.38 (m, 5H), 4.52 (bs, 1H, NH), 6.08 (bs, 1H), 6.23 (s, 2H), 7.20-7.24 (m, 2H), 7.34 (d, 2H, J=3.0), 7.53 (d, 3H, J=7.0), 7.65 (d, 1H, J=9.0), 7.71 (d, 2H, J=7.5), 8.09 (s, 1H), 8.22 (s, 1H), 9.27 (bs, 1H, NH); $^{13}$C NMR (125.7 MHz, CDCl$_3$) ∂ 12.16, 14.35, 17.63, 18.65, 21.46, 25.47, 26.73, 30.99, 32.73, 33.08, 40.63, 47.15, 56.17, 61.70, 68.42, 73.87, 118.21, 118.60, 119.99, 120.60, 124.36, 125.11, 125.93, 127.03, 127.71, 130.36, 132.77, 134.27, 135.02, 135.54, 135.64, 137.39, 139.46, 141.25, 141.29, 141.58, 143.63, 143.75, 153.95, 156.75, 163.86.

[Entry 46]

$^1$H NMR (500.1 MHz, MeOD-d$_4$) ∂ 1.28 (t, 2H, J=7.5), 1.78-1.97 (m, 2H), 2.05 (s, 3H), 3.26 (t, 2H, J=7.0), 4.53 (dd, 1H, J=5.5, 8.5), 7.47 (dd, 1H, J=2.0, 9.0), 7.83 (d, 1H, J=9.0), 7.99 (s, 1H), 8.17 (d, 1H, J=2.0).

[Entry 47 intermediate] 5-(2-Dimethylamino-ethoxy)-benzo[b]selenophene-2-carboxylic acid ethyl ester:

$^1$H NMR (500.1 MHz, CDCl$_3$) ∂ 1.39 (t, 3H, J=7.0), 2.34 (s, 6H), 2.75 (t, 2H, J=5.5), 4.10 (t, 2H, J=5.5), 4.37 (q, 2H, J=7.0), 7.06 (dd, 1H, J=2.5, 9.0), 7.34 (d, 1H, J=2.0), 7.73 (d, 1H, J=8.5), 8.19 (s, 1H); $^{13}$C NMR (125.7 MHz, CDCl$_3$) ∂ 14.34, 45.94, 58.30, 61.62, 66.39, 110.17, 117.78, 126.47, 134.06, 135.98, 137.53, 142.16, 157.27, 163.95.

[Entry 47] 5-(2-Dimethylamino-ethoxy)-benzo[b]selenophene-2-carboxylic acid:

$^1$H NMR (500.1 MHz, DMSO-d$_6$) ∂ 2.82 (s, 6H), 3.50 (t, 2H, J=4.0), 4.43 (t, 2H, J=4.0), 7.14 (dd, 1H, J=1.5, 8.5), 7.64 (d, 1H, J=2.0), 7.99 (d, 1H, J=8.5), 8.21 (s, 1H); $^{13}$C NMR (125.7 MHz, DMSO-d$_6$) ∂ 42.71, 55.07, 62.77, 110.83, 117.03, 127.12, 133.12, 135.68, 140.19, 142.32, 155.82, 164.85.

[Entry 48 intermediate] 6-(2-Dimethylamino-ethoxy)-benzo[b]selenophene-2-carboxylic acid ethyl ester:

$^1$H NMR (500.1 MHz, CDCl$_3$) ∂ 1.37 (t, 3H, J=7.0), 2.33 (s, 6H), 2.74 (t, 2H, J=5.5), 4.10 (t, 2H, J=5.5), 4.34 (q, 2H, J=7.0), 7.01 (dd, 1H, J=2.5, 9.0), 7.35 (d, 1H, J=2.0), 7.72 (d, 1H, J=9.0), 8.16 (s, 1H); $^{13}$C NMR (125.7 MHz, CDCl$_3$) ∂ 15.34, 46.87, 59.17, 62.40, 67.38, 109.97, 116.56, 129.01, 134.29, 135.00, 136.07, 146.80, 159.46, 164.96.

[Entry 48] 6-(2-Dimethylamino-ethoxy)-benzo[b]selenophene-2-carboxylic acid:

$^1$H NMR (500.1 MHz, MeOD-d$_4$) ∂ 2.98 (s, 6H), 3.64 (s, 2H), 4.43 (s, 2H), 7.09 (d, 1H, J=8.0), 7.60 (s, 1H), 7.76 (d, 1H, J=7.0), 8.04 (s, 1H); $^{13}$C NMR (125.7 MHz, MeOD-d$_4$) ∂ 44.18, 57.68, 63.84, 111.00, 116.25, 129.08, 133.57, 137.89, 139.87, 146.89, 158.29, 169.32.

[Entry 49] 7-Acetyl-6-methoxy-benzo[b]selenophene-2-carboxylic acid ethyl ester:

$^1$H NMR (500.1 MHz, CDCl$_3$) ∂ 1.40 (t, 3H, J=7.5), 2.79 (s, 3H), 4.06 (s, 3H), 4.37 (q, 2H, J=7.0), 7.18 (d, 1H, J=8.5), 8.01 (d, 1H, J=9.0), 8.27 (s, 1H); $^{13}$C NMR (125.7 MHz, CDCl$_3$) ∂ 14.37, 32.80, 56.23, 61.27, 110.58, 121.67, 132.77, 133.07, 135.72, 138.31, 146.50, 161.18, 164.71, 196.75.

[Entry 50] 5-Methoxy-benzo[b]selenophene-2-carboxylic acid:

$^1$H NMR (CDCl$_3$, 500 MHz) ∂ 8.20 (d, J=7 Hz, 1H), 7.79 (d, J=9, 1H), 7.43 (d, J=2.5 Hz, 1H), 7.04 (dd, J=9.0, 2.5 Hz, 1H), 3.84 (s, 3H); $^{13}$C NMR (125.7 MHz, CDCl$_3$), ∂ 167.18, 159.61, 143.87, 139.54, 137.22, 135.39, 127.55, 118.37, 110.27, 55.98.

[Entry 51] 6-Methoxy-benzo[b]selenophene-2-carboxylic acid:

$^1$H NMR (500.1 MHz, DMSO-d$_6$) ∂ 3.87 (s, 3H), 7.03 (dd, 1H, J=2.0, 8.5), 7.67 (d, 1H, J=2.0), 7.86 (d, 1H, J=9.0), 8.16 (s, 1H); $^{13}$C NMR (125.7 MHz, DMSO-d$_6$) ∂ 55.48, 108.90, 114.84, 128.06, 132.83, 135.11, 136.32, 145.14, 158.56, 165.17.

[Entry 52] 5,6-Dimethoxy-benzo[b]selenophene-2-carboxylic acid:

$^1$H NMR (500.1 MHz, MeOD-d$_4$) ∂ 3.87 (s, 3H), 3.90 (s, 3H), 7.40 (s, 1H), 7.48 (s, 1H), 8.10 (s, 1H); $^{13}$C NMR (125.7 MHz, MeOD-d$_4$) ∂ 56.53, 56.64, 108.56, 109.55, 134.79, 134.93, 136.49, 138.81, 150.07, 151.56, 168.46.

[Entry 53] 1,3-Dioxa-5-selena-s-indacene-6-carboxylic acid:

$^1$H NMR (500.1 MHz, MeOD-d$_4$) ∂ 6.02 (s, 2H), 7.30 (s, 1H), 7.37 (s, 1H), 8.11 (s, 1H); $^{13}$C NMR (125.7 MHz, MeOD-d$_4$) ∂ 103.26, 105.82, 106.41, 135.30, 136.17, 137.03, 140.02, 148.90, 150.35, 166.97.

[Entry 54] Selenolo[2,3-b]pyridine-2-carboxylic acid:

$^1$H NMR (500.1 MHz, MeOD-d$_4$) ∂ 7.48 (dd, 1H, J=5.0, 8.0), 8.18 (s, 1H), 8.31 (d, 1H, J=8.0), 8.56 (d, 1H, J=9.5); $^{13}$C NMR (125.7 MHz, MeOD-d$_4$) ∂ 121.43, 129.10, 135.78, 148.20, 148.35, 166.87, 170.94.

[Entry 55] Selenolo[3,2-b]furan-5-carboxylic acid:

$^1$H NMR (500.1 MHz, MeOD-d$_4$) ∂ 6.85 (s, 1H), 7.70 (s, 1H), 7.94 (s, 1H); $^{13}$C NMR (125.7 MHz, MeOD-d$_4$) ∂ 110.51, 119.76, 129.76, 140.01, 149.31, 158.81, 168.25.

[Entry 56] Selenolo[3,2-b]thiophene-5-carboxylic acid:

$^1$H NMR (500.1 MHz, MeOD-d$_4$) ∂ 7.34 (d, 1H, J=5.0), 7.63 (d, 1H, J=5.0), 8.17 (s, 1H); $^{13}$C NMR (125.7 MHz, MeOD-d$_4$) ∂ 124.27, 129.65, 132.43, 140.26, 141.54, 145.42, 167.01.

[Entry 57] 7-Methoxy-benzo[b]selenophene-2-carboxylic acid(60%):

$^1$H NMR (500.1 MHz, MeOD-d$_4$) ∂ 3.99 (s, 3H), 7.01 (d, 1H, J=7.5), 7.41-7.44 (m, 1H), 7.60 (d, 1H, J=7.5), 8.28 (s, 1H); $^{13}$C NMR (125.7 MHz, MeOD-d$_4$) ∂ 55.85, 106.79, 119.89, 126.92, 131.36, 133.73, 139.11, 142.62, 155.68, 164.82.

[Entry 58] 5-Nitro-benzo[b]selenophene-2-carboxylic acid:

$^1$H NMR (500.1 MHz, MeOD-d$_4$) ∂ 8.22-8.23 (m, 2H), 8.42 (s, 1H), 8.85 (d, 1H, J=1.5); $^{13}$C NMR (125.7 MHz, MeOD-d$_4$) ∂ 118.80, 121.04, 125.76, 140.74, 145.22, 147.80, 149.50, 153.14, 171.24.

9. Producing Method of Selenophene-Fused Aromatic Compounds in Accordance with Fourth Aspect of Example Embodiments The producing method of selenophene-fused aromatic compounds in accordance with the fourth aspect of the example embodiments has been explained in detail, but the example embodiments may not be limited thereto.

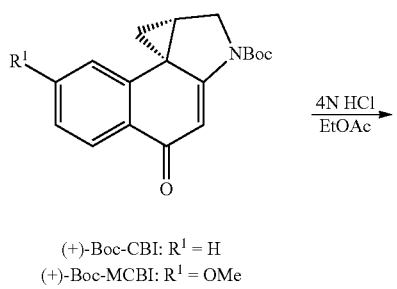

(+)-Boc-CBI: R¹ = H
(+)-Boc-MCBI: R¹ = OMe

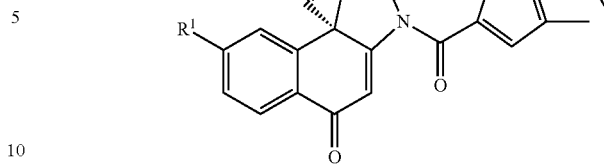

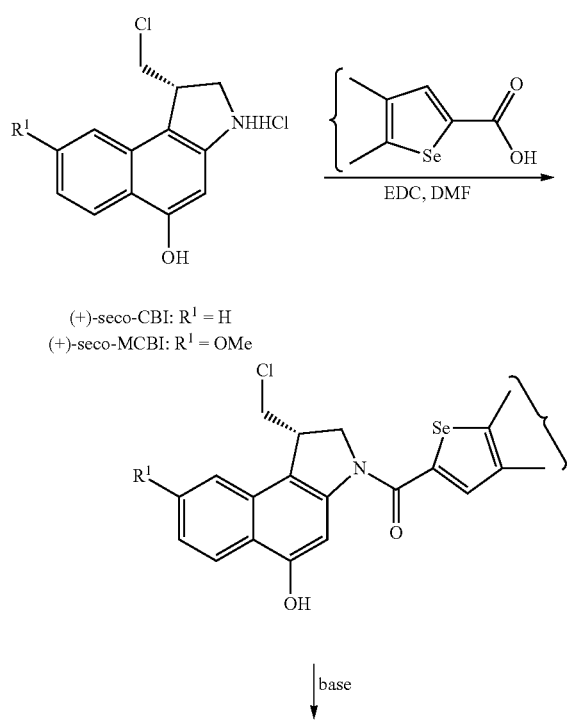

(+)-seco-CBI: R¹ = H
(+)-seco-MCBI: R¹ = OMe

Selenophene-fused aromatic compounds corresponding to Entry 59 to Entry 84 were produced in accordance with the fourth aspect of the example embodiments as follows.

(+)-Boc-MCBI and (+)-Boc-CBI were synthesized by the method as reported in J. Org. Chem. 1996, 61, 1710. 30 mg or 50 mg of a starting material was mixed with 3 mL of 4N HCl-EtOAc and stirred at −40° C. for 30 minutes and then left as it was at room temperature for 30 minutes. Thereafter, nitrogen gas was added thereto to concentrate the reaction solution, and the residue was dried for 15 minutes or more under a depressurized condition.

1.0 mL of DMF was added thereto with addition of 1.1 eq. of benzoselenophene-2-carboxylic acid and 3.0 eq. of EDCI to produce a reaction mixture. The reaction mixture was stirred at 25° C. for 10 hours. After the stirring, 3 mL of water was added to the reaction mixture, the reaction product was extracted by using 4×5 mL of EtOAc. During this process, an organic layer was collected and dried by using $Na_2SO_4$ and then concentrated under a depressurized condition.

The selenophene-fused aromatic compounds corresponding to Entry 59 to Entry 84 as reaction products were refined by a thin layer chromatography (methanol-methylene chloride developing solvent) and synthesized at a yield of from 15% to 55%. Structures of the compounds were as shown in [Table 4] below. Further, NMR experiments were performed to the respective compounds, and data thereof were as described under [Table 4].

TABLE 4

<Structures of compound in accordance with Comparative Example 1 and selenophene-fused aromatic compounds corresponding to Entry 59 to Entry 84>

| | Selenophene-fused aromatic compound |
|---|---|
| Comparative Example 1 | 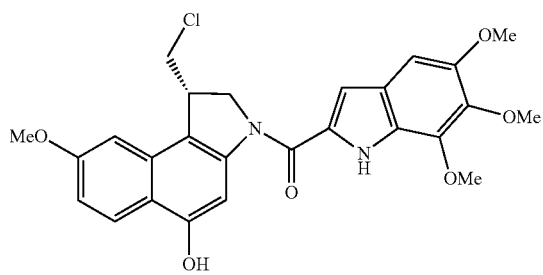 [SMILES: COc1ccc2c(O)cc3c(c2c1)[C@H](CCl)CN3C(=O)c1cc2cc(OC)c(OC)c(OC)c2[nH]1] |

TABLE 4-continued

<Structures of compound in accordance with Comparative
Example 1 and selenophene-fused aromatic compounds
corresponding to Entry 59 to Entry 84>

Selenophene-fused aromatic compound

Entry 59

Entry 60

Entry 61

Entry 62

Entry 63

Entry 64

TABLE 4-continued
<Structures of compound in accordance with Comparative
Example 1 and selenophene-fused aromatic compounds
corresponding to Entry 59 to Entry 84>
Selenophene-fused aromatic compound
Entry 66
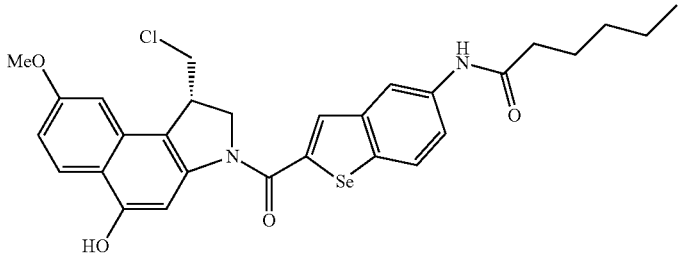 [SMILES: CCCCCC(=O)Nc1ccc2[se]c(C(=O)N3C[C@@H](CCl)c4c3cc(O)c3ccc(OC)cc43)cc2c1]
Entry 67
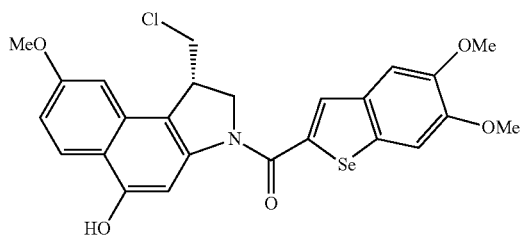 [SMILES: COc1ccc2c(O)cc3c(c2c1)[C@H](CCl)CN3C(=O)c1cc2cc(OC)c(OC)cc2[se]1]
Entry 68
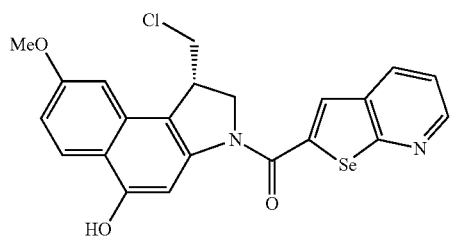 [SMILES: COc1ccc2c(O)cc3c(c2c1)[C@H](CCl)CN3C(=O)c1cc2cccnc2[se]1]
Entry 69
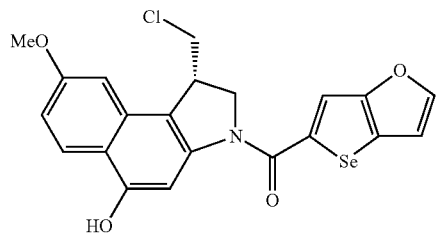 [SMILES: COc1ccc2c(O)cc3c(c2c1)[C@H](CCl)CN3C(=O)c1cc2occc2[se]1]
Entry 70
Comparative
Example 2
(CBI-TMI)
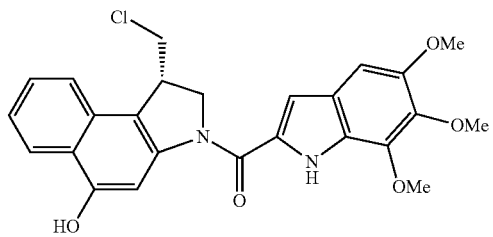 [SMILES: COc1cc2cc(C(=O)N3C[C@@H](CCl)c4c3cc(O)c3ccccc43)[nH]c2c(OC)c1OC]
Entry 71
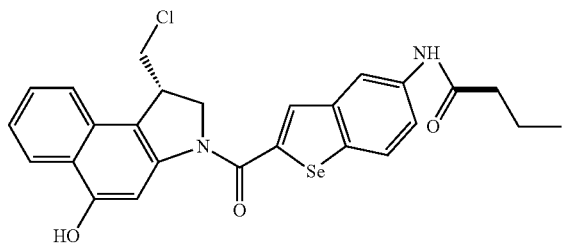

TABLE 4-continued
<Structures of compound in accordance with Comparative Example 1 and selenophene-fused aromatic compounds corresponding to Entry 59 to Entry 84>
Selenophene-fused aromatic compound
Entry 72
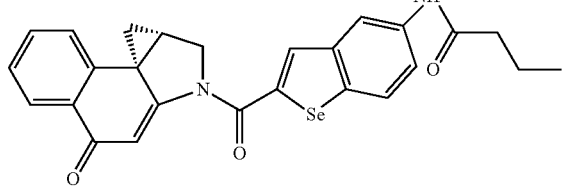
Entry 73
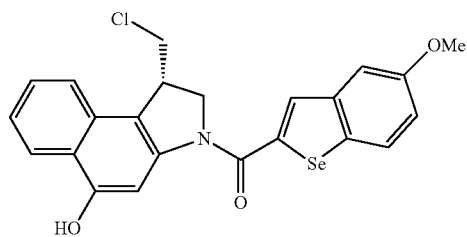 [SMILES: COc1ccc2[se]c(C(=O)N3C[C@@H](CCl)c4c3cc(O)c3ccccc43)cc2c1]
Entry 74
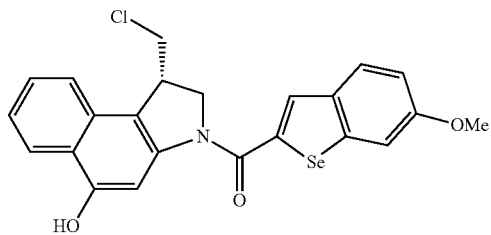 [SMILES: COc1ccc2cc(C(=O)N3C[C@@H](CCl)c4c3cc(O)c3ccccc43)[se]c2c1]
Entry 75
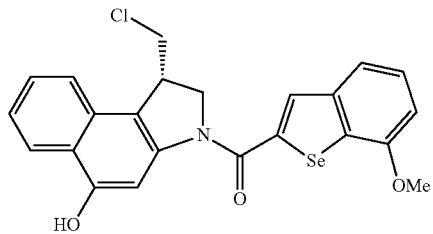 [SMILES: COc1cccc2cc(C(=O)N3C[C@@H](CCl)c4c3cc(O)c3ccccc43)[se]c12]
Entry 76
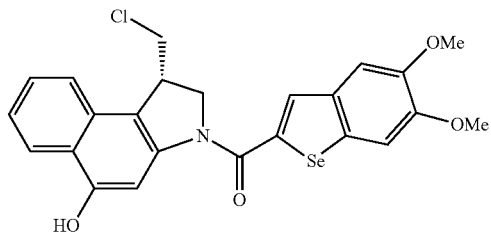 [SMILES: COc1cc2cc(C(=O)N3C[C@@H](CCl)c4c3cc(O)c3ccccc43)[se]c2cc1OC]
Entry 77
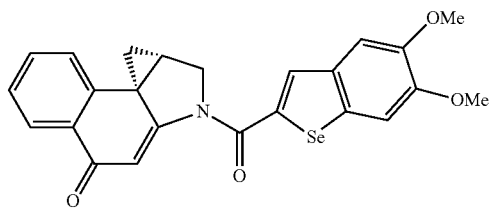 [SMILES: COc1cc2cc(C(=O)N3C[C@H]4C[C@@]45C3=CC(=O)c3ccccc35)[se]c2cc1OC]

TABLE 4-continued
<Structures of compound in accordance with Comparative Example 1 and selenophene-fused aromatic compounds corresponding to Entry 59 to Entry 84>
Selenophene-fused aromatic compound
Entry 78 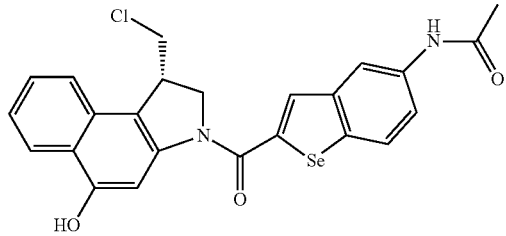 [SMILES: CC(=O)Nc1ccc2[se]c(C(=O)N3C[C@@H](CCl)c4c3cc(O)c3ccccc43)cc2c1]
Entry 79 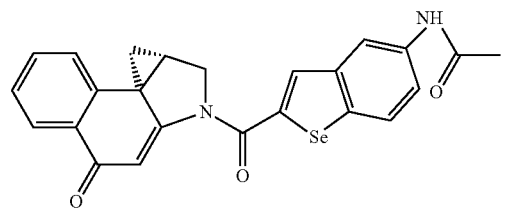
Entry 80 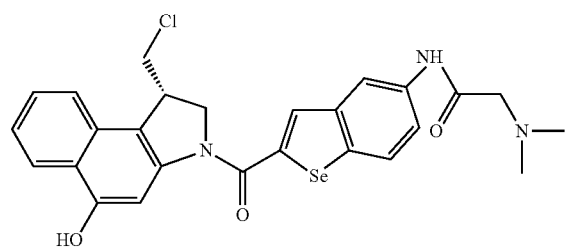 [SMILES: CN(C)CC(=O)Nc1ccc2[se]c(C(=O)N3C[C@@H](CCl)c4c3cc(O)c3ccccc43)cc2c1]
Entry 81 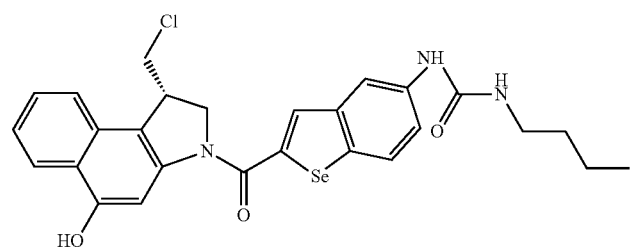 [SMILES: CCCCNC(=O)Nc1ccc2[se]c(C(=O)N3C[C@@H](CCl)c4c3cc(O)c3ccccc43)cc2c1]
Entry 82 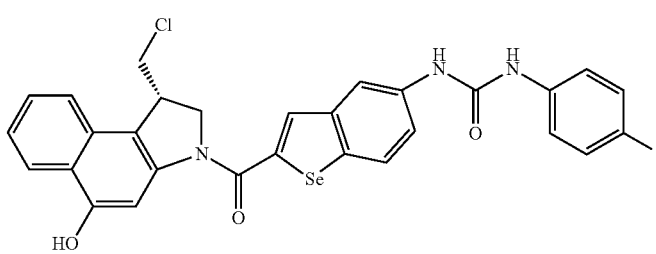
Entry 83 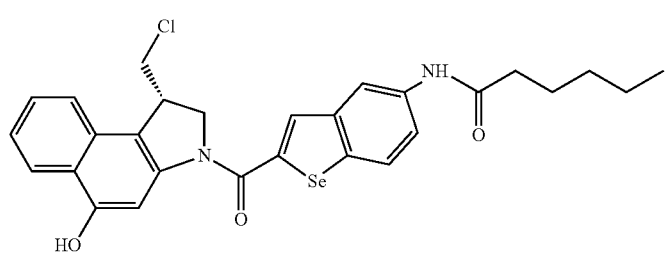 [SMILES: CCCCCC(=O)Nc1ccc2[se]c(C(=O)N3C[C@@H](CCl)c4c3cc(O)c3ccccc43)cc2c1]

TABLE 4-continued

<Structures of compound in accordance with Comparative
Example 1 and selenophene-fused aromatic compounds
corresponding to Entry 59 to Entry 84>

Selenophene-fused aromatic compound

Entry 84

<NMR data of a compound in accordance with Comparative Example 1 and selenophene-fused aromatic compounds corresponding to Entry 59 to Entry 84 shown in [Table 4]>

Comparative Example 1 seco-MCBI-TMI $^1$H NMR (DMSO-d6, 500 MHz) ∂ 11.41 (s, 1H, NH), 10.35 (s, 1H, OH), 8.02 (d, J=9.0 Hz, 1H), 7.72 (br s, 1H), 7.10 (d, J=2.5 Hz, 1H), 7.05 (d, J=2.0 Hz, 1H), 6.99 (dd, J=9.2, 2.4 Hz, 1H), 6.96 (s, 1H), 4.71 (t, J=10 Hz, 1H), 4.46 (d, J=10 Hz, 1H), 4.15-4.10 (m, 1H), 4.05 (dd, J=11.0, 3.5 Hz, 1H), 3.94 (s, 3H, OCH$_3$), 3.91 (s, 3H, OCH$_3$), 3.82 (s, 3H, OCH$_3$), 3.80 (s, 3H, OCH$_3$), 3.78-3.80 (m, 1H); LCMS, m/e 497.1 (M$^+$+H).

[Entry 59] seco-MCBI-Nitro-Selenophene:
$^1$H NMR (DMSO-d$_6$, 500 MHz) ∂ 10.36 (s, 1H, OH), 8.93 (d, J=2.5 Hz, 1H), 8.54 (s, 1H), 8.45 (d, J=9.0 Hz, 1H), 8.23 (dd, J=9.0, 2.5 Hz, 1H), 8.03 (d, J=9.5 Hz, 1H), 7.72 (br s, 1H), 7.13 (d, J=2.0 Hz, 1H), 7.02 (dd, J=9.5, 2.5 Hz, 1H), 4.72 (m, 1H), 4.47 (d, J=10 Hz, 1H), 4.22 (m, 1H), 4.04 (dd, J=11.0, 3.0 Hz, 1H), 3.92 (s, 3H, OCH$_3$), 3.92-3.88 (m, 1H); LCMS, m/e 517.1 (M$^+$+H).

[Entry 60] seco-MCBI-Methoxy-Selenophene:
$^1$H NMR (DMSO-d6, 500 MHz) ∂ 10.34 (s, 1H, OH), 8.23 (s, 1H), 8.02 (d, J=9.0 Hz, 1H), 7.99 (d, J=8.5 Hz, 1H), 7.67 (br s, 1H), 7.56 (d, J=2.5 Hz, 1H), 7.12 (d, J=2.0 Hz, 1H), 7.08 (dd, J=9.0, 2.5 Hz, 1H), 7.01 (dd, J=9.0, 2.0 Hz, 1H), 4.73 (t, J=9.5 Hz, 1H), 4.48 (m, 1H), 4.18 (m, 1H), 4.04 (dd, J=14.5, 7.0 Hz, 1H), 3.91 (s, 3H, OCH$_3$), 3.82- (s, 3H, OCH$_3$), 3.85 3.81 (m, 1H); LCMS, m/e 502.2 (M$^+$+H).

[Entry 61] seco-MCBI-Acetamino-Selenophene:
$^1$H NMR (DMSO-d6, 500 MHz) ∂ 10.32 (s, 1H, OH), 10.09 (s, 1H, NH), 8.44 (s, 1H), 8.27 (s, 1H), 8.02 (d, J=4.5 Hz, 1H), 8.01 (d, 4.5 Hz, 1H), 7.68 (br s, 1H), 7.46 (dd, J=8.5, 2 Hz, 1H), 7.12 (d, J=2.0 Hz, 1H), 7.01 (d, J=9.0, 2.5 Hz, 1H), 4.77 (t, J=9.5 Hz, 1H), 4.45 (d, J=11.5 Hz, 1H), 4.17 (m, 1H), 4.03 (dd, J=11.5, 3.5 Hz, 1H), 3.91 (s, 3H, OCH$_3$), 3.89-3.80 (dd, J=11.0, 4.0 Hz, 1H); LCMS, m/e 529.2 (M$^+$+H).

[Entry 62]
$^1$H NMR (500.1 MHz, ACETONE-d$_6$) ∂ 9.32 (s, 1H), 8.508 (d, 1H, J=2.0 Hz), 8.22 (s, 1H), 8.025 (d, 1H, J=8.5 Hz), 7.98 (d, 1H, J=9.0 Hz), 7.509 (dd, 1H, J=2, 8.5 Hz), 6.98 (dd, 1H, J=2.5, 9 Hz), 6.765 (s, 1H), 6.68 (dd, 1H, J=2.5 Hz), 4.6 (dd, 1H, J=5.0, 10.0 Hz), 4.44 (d, 1H, J=10.5 Hz), 3.9 (s, 3H), 3.18 (m, 1H), 2.08 (s, 3H), 1.82 (dd, 2H, J=4 Hz, 7.5 Hz)

[Entry 63]
$^1$H NMR (500.1 MHz, CDCl$_3$) ∂ 3.43 (t, 1H, J=11.3), 3.88 (m, 1H), 3.90 (s, 3H), 3.98 (m, 1H), 4.56 (m, 1H), 4.64 (d, 1H, J=11.3), 6.85 (d, 1H, J=2.8), 7.02 (dd, 1H, J=2.8, 9.4), 7.31 (s, 1H), 7.34 (s, 1H), 7.96 (s, 1H), 8.07 (s, 1H), 8.21 (d, 1H, J=9.4), 8.94 (s, 1H); $^{13}$C NMR (125.7 MHz, CDCl$_3$) ∂ 42.82, 45.60, 55.35, 56.17, 99.07, 100.93, 106.39, 114.97, 115.60, 118.20, 125.78, 130.77, 131.22, 134.63, 136.11, 138.80, 141.81, 148.50, 149.76, 155.01, 164.30.

[Entry 64]
$^1$H NMR (500.1 MHz, CDCl$_3$) ∂ 3.48 (t, 1H, J=11.3), 3.90 (m, 1H), 3.91 (s, 3H), 3.95 (s, 3H), 4.00 (m, 1H), 4.60 (t, 1H, J=9.4), 4.69 (d, 1H, J=10.7), 6.92 (s, 1H), 7.05 (m, 2H), 7.43 (d, 1H, J=1.6), 7.79 (d, 1H, J=8.8), 7.82 (m, 1H), 7.97 (s, 1H), 8.17 (d, 1H, J=10.1)

[Entry 65]
$^1$H NMR (500.1 MHz, CDCl$_3$) ∂ 1.05 (t, 3H, J=7.6), 1.81 (m, 2H), 2.39 (t, 2H, J=7.9), 3.36 (m, 1H), 3.79 (m, 1H), 3.86 (m, 1H), 3.91 (s, 3H), 4.18 (m, 1H), 4.38 (d, 1H, J=7.8), 6.7 (dd, 1H, J=2.8, 36.5), 7.02 (m, 1H), 7.34 (d, 1H, J=8.8), 7.49 (s, 1H) 7.75 (d, 1H, J=9.1), 7.87 (s, 1H), 8.11 (s, 1H), 8.21 (d, 1H, J=9.4)

[Entry 66]
$^1$H NMR (500.1 MHz, CDCl$_3$) ∂ 0.94 (t, 3H, J=7.6), 1.40 (m, 4H), 1.79 (m, 2H), 2.41 (t, 2H, J=8.1), 3.35 (m, 1H), 3.66 (m, 1H), 3.80 (d, 1H, J=12.6), 3.91 (s, 3H), 4.39 (m, 2H), 6.76 (s, 1H), 7.03 (d, 1H, J=9.4), 7.34 (d, 1H, J=8.5), 7.49 (m, 1H) 7.74 (d, 1H, J=11.9), 7.88 (s, 1H), 8.13 (s, 1H), 8.20 (d, 1H, J=9.4)

[Entry 67]
$^1$H NMR (500.1 MHz, CDCl$_3$) ∂ 3.46 (t, 1H, J=11.3), 3.90 (d, 1H, J=3.1), 3.93 (s, 3H), 3.96 (s, 3H), 3.97 (m, 1H), 3.99 (s, 3H), 4.58 (m, 1H), 4.67 (dd, 1H, J=1.6, 11.0), 6.89 (d, 1H, J=2.8), 7.04 (dd, 1H, J=2.8, 9.4), 7.32 (s, 1H), 7.36 (s, 1H), 7.97 (s, 1H), 7.98 (d, 1H, J=9.4), 8.20 (d, 1H, J=9.4)

[Entry 68]
$^1$H NMR (500.1 MHz, ACETONE-d$_6$) ∂ 9.4 (s, 1H), 8.605 (dd, 1H, J=4.5, 1 Hz), 8.32 (dd, 1H, J=1.8 Hz), 8.162 (d, 1H, J=2 Hz), 7.65 (brs, 1H), 7.492 (dd, 1H, J=4.5, 8.0 Hz), 7.187 (d, 1H, J=2.5 Hz), 7.035 (dd, 1H, J=2.5, 9), 4.717 (t, 1H, J=10.0 Hz), 4.635 (d, 1H, J=11.0 Hz), 4.18 (m, 1H), 4.048 (dd, 1H, J=3.5, 11.5 Hz), 3.9 (s, 3H), 3.832 (m, 1H). $^{13}$C NMR (125.7 MHz, ACETONE-d$_6$) ∂ 42.85, 47.39, 55.76, 56.50, 99.50, 102.27, 116.01, 116.28, 116.67, 118.73, 121.43, 125.99, 128.31, 132.80, 135.29, 137.25, 143.53, 149.03, 155.34, 160.19, 162.83, 163.08, 166.26

[Entry 69]
$^1$H NMR (500.1 MHz, CDCl$_3$) ∂ 3.47 (m, 1H), 3.92 (m, 1H), 3.94 (s, 3H), 4.02 (t, 1H, J=11.0), 4.60 (m, 1H), 4.68 (d, 1H, J=11.0), 6.88 (d, 1H, J=2.2), 6.91 (d, 1H, J=2.8), 7.05 (m, 1H), 7.66 (d, 1H, J=2.5), 7.79 (s, 1H), 7.93 (s, 1H), 8.15 (d, 1H, J=9.1)

[Entry 70]
$^1$H NMR (500.1 MHz, DMSO) ∂ 10.46 (s, 1H, OH), 8.12 (d, 1H, J=8.5 Hz, C6-H), 7.90 (br s, 1H, C4-H), 7.84 (d, 1H, J=8.5 Hz, C9-H), 7.52 (t, 1H, J=8.0 Hz, C8-H), 7.36 (t, 1H, J=8.0 Hz, C7-H), 7.06 (s, 1H, C3'-H), 6.97 (s, 1H, C4'-H), 4.74 (apparent t, 1H, J=10.4 Hz, C2-H), 4.46 (d, 1H, J=11.2 Hz, C2-H), 4.17 (m, 1H, C1-H), 4.01 (d, 1H, J=10.6 Hz, CHHCl), 3.94 (s, 3H, OCH3), 3.83 (s, 3H, OCH$_3$), 3.82 (d, 1H, J=11.2 Hz, CHHCl), 3.79 (s, 3H, OCH$_3$)

[Entry 71]
$^1$H NMR (500.1 MHz, DMSO) ∂ 10.4 (s, 1H), 10.0 (s, 1H), 8.48 (s, 1H), 8.3 (s, 1H), 8.15 (d, 1H, J=8.5 Hz), 8.05 (d, 1H, J=8.5 Hz), 7.88 (d, 1H, J=8 Hz), 7.86 (brs 1H), 7.56 (t, 1H, J=8 Hz), 7.5 (dd, 1H, J=8.5, 2 Hz), 7.4 (t, 1H, J=8.0 Hz), 7.4 (t, 1H, J=8.0 Hz), 4.8 (t, 1H, J=9.5 Hz), 4.45 (dd, 1H, J=11.0, 2.0 Hz), 4.2 (m, 1H), 4.01 (dd, 1H, 3.0, J=11.0 Hz), 3.89 (m, 1H), 2.3 (t d, 2H, J=7.5, 1.5 Hz), 1.6 (qr, 2H, J=7.5 Hz), 0.9 (t, 1H, J=3.0, 11.0 Hz). $^{13}$C NMR (125.7 MHz, Acetone) ∂ 13.96, 14.11, 19.72, 24.41, 42.75, 47.91, 54.67, 101.58, 115.48, 117.07, 118.01, 120.03, 123.35, 123.62, 123.76, 124.34, 128.21, 128.40, 143.0, 130.92, 137.44, 143.66, 155.22, 163.58, 169.85, 172.13

[Entry 72]
$^1$H NMR (500.1 MHz, ACETONE-d$_6$) ∂ 9.26 (s, 1H), 8.537 (d, 1H, J=8.5 Hz), 8.23 (s, 1H), 8.1 (d, 1H, J=1.0 Hz), 7.98 (d, 1H, J=8.5 Hz), 7.55 (m, 2H), 7.4 (m, 1H), 7.2 (d, 1H, J=8 Hz), 6.834 (s, 1H), 4.621 (dd, 1H, J=10.5, 5 Hz), 4.46 (d, 1H, J=10.5 Hz), 3.17 (m, 1H), 2.366 (t, 1H, J=7.5 Hz), 1.81 (t, 2H, J=2 Hz), 1.69 (m, 2H), 0.96 (t, 3H, J=7.5 Hz). $^{13}$C NMR (125.7 MHz, Acetone) ∂ 14.14, 19.75, 25.32, 33.60, 39.78, 55.72, 112.31, 117.57, 118.22, 120.52, 123.00, 123.22, 126.71, 126.95, 127.04, 127.30, 132.56, 132.93, 133.79, 138.55, 141.74, 143.13, 143.45, 161.44, 165.22, 172.15, 185.56

[Entry 73]
$^1$H NMR (500.1 MHz, Acetone) ∂ 10.4 (s, 1H), 8.2 (s, 1H), 8.1 (d, 1H, J=8.0 Hz), 8.0 (d, 1H, J=8.5 Hz), 7.8 (d, 1H, J=8.5 Hz), 7.58 (s, 1H), 7.56 (t, 1H, J=8.5 Hz), 7.4 (t, 1H, J=8 Hz), 7.1 (d, 1H, J=9.0 Hz), 4.8 (t, 1H, J=10.0 Hz), 4.45 (d, 1H, J=11.0 Hz), 4.2 (m, 1H) 4.01 (qr, 1H, J=7 Hz), 3.89 (m, 1H), 3.80 (s, 3H). $^{13}$C NMR (125.7 MHz, Acetone) ∂ 43.14, 47.72, 55.96, 56.77, 101.64, 110.34, 117.54, 123.67, 123.75, 124.38, 124.40, 127.26, 128.49, 130.74, 131.43, 143.29, 144.36, 155.24, 159.34, 163.57

[Entry 74]
$^1$H NMR (500.1 MHz, Acetone) ∂ 9.4 (s, 1H), 8.25 (d, 1H, J=8.5 Hz), 8.2 (s, 1H), 7.9 (m, 4H), 7.68 (s, 1H), 7.54 (td, 1H, J=6.5, 1 Hz), 7.4 (td 1H, J=10, 1 Hz), 7.01 (dd, 1H, J=2, 8.5 Hz), 4.8 (t, 1H, J=10.0 Hz), 4.7 (dd, 1H, J=1.5, 10.5 Hz), 4.2 (m, 1H) 4.01 (dd, 1H, J=3.5, 11.5 Hz), 3.90 (s, 3H), 3.80 (m, 1H). $^{13}$C NMR (125.7 MHz, Acetone) ∂ 43.21, 47.73, 56.13, 56.17, 101.69, 109.18, 115.93, 116.92, 123.64, 124.30, 124.38, 128.45, 129.05, 130.77, 137.13, 137.39, 143.46, 145.4, 155.19, 160.16, 163.49

[Entry 75]
$^1$H NMR (500.1 MHz, Acetone) ∂ 9.5 (s, 1H), 8.25 (d, 1H, J=5 Hz), 8.23 (s, 1H), 7.9 (s, 1H), 7.9 (d, 1H, J=8.5 Hz), 7.6 (d, 1H, J=7.5 Hz), 7.5 (t, 1H, J=8.0 Hz), 7.43 (t, 1H, J=8.0 Hz), 7.4 (t, 1H, J=7.0 Hz), 4.8 (t, 1H, J=10.5 Hz), 4.68 (dd, 1H, J=1.5, 10.5 Hz), 4.25 (m, 1H) 4.01 (dd, 1H, J=3.5, 11.5 Hz), 4.01 (s, 3H), 3.82 (dd, 1H, J=8.5, 11 Hz). $^{13}$C NMR (125.7 MHz, Acetone) ∂ 43.14, 47.74, 56.47, 56.79, 107.13, 117.13, 120.72, 123.69, 124.41, 127.89, 128.50, 131.05, 131.44, 131.89, 143.28, 144.67, 155.25, 157.31, 163.55

[Entry 76]
$^1$H NMR (500.1 MHz, Acetone) ∂ 9.25 (s, 1H), 8.3 (d, 1H, J=8.5 Hz), 8.2 (s, 1H), 7.9 (s, 1H), 7.8 (d, 1H, J=8.5 Hz), 7.68 (s, 1H), 7.55 (m, 1H), 7.52 (s, 1H) 7.4 (m, 1H), 4.8 (t, 1H, J=11.0 Hz), 4.7 (dd, 1H, J=2, 11.0 Hz), 4.3 (m, 1H) 4.05 (dd, 1H, J=3.5, 11.5 Hz), 3.94 (s, 3H), 3.89 (s, 3H), 3.8 (dd, 1H, J=9, 11.5 Hz). $^{13}$C NMR (125.7 MHz, Acetone) ∂ 41.71, 46.17, 54.77, 54.88, 54.93, 100.18, 101.99, 106.74, 108.12, 115.32, 122.08, 122.73, 122.84, 126.9, 129.46, 135.08, 141.98, 148.55, 149.86, 153.65, 162.01

[Entry 77]
$^1$H NMR (500.1 MHz, ACETONE-d$_6$) ∂ 8.17 (s, 1H), 8.099 (dd, 1H, J=7.5, 1 Hz), 7.64 (s, 1H), 7.60 (m, 1H), 7.489 (s, 1H), 7.422 (m, 1H), 7.18 (d, 1H, 7.5 Hz), 6.78 (s, 1H), 4.58 (dd, 1H, J=10.5, 5 Hz), 4.42 (d, 1H, J=10.0 Hz), 3.92 (s, 3H), 3.86 (s, 3H), 3.16 (m, 1H), 1.802 (m, 2H)

[Entry 78]
$^1$H NMR (500.1 MHz, Acetone) ∂ 9.3 (s, 1H), 8.5 (s, 1H), 8.22 (d, 1H, J=8.5 Hz), 8.2 (s, 1H), 7.98 (d, 1H, J=9 Hz), 7.9 (d, 1H, J=8.5 Hz), 7.58 (m, 2H), 7.4 (t, 1H, J=8.0 Hz), 4.8 (t, 1H, J=11.0 Hz), 4.7 (dd, 1H, J=2, 11.0 Hz), 4.24 (m, 1H) 4.05 (dd, 1H, J=3.5, 11.5 Hz), 3.85 (dd, 3H, J=9, 11.5 Hz), 2.1 (s, 3H). $^{13}$C NMR (125.7 MHz, Acetone) ∂ 24.11, 43.53, 48.13, 57.17, 102.99, 117.18, 118.39, 120.64, 123.30, 124.38, 126.45, 128.45, 131.05, 132.77, 137.13, 138.39, 143.46, 144.4, 155.29, 164.16, 168.49

[Entry 79]
$^1$H NMR (505.1 MHz, ACETONE-d$_6$) ∂ 9.32 (d, 1H, J=7), 8.51 (s, 1H), 8.24 (s, 1H), 8.09 (d, 1H, J=8.0), 7.98 (d, 1H, 8.5 Hz), 7.581 (t, 1H, J=7.5 Hz), 7.51 (d, 1H, J=8.5 Hz), 7.428 (t, 1H, 7.5 Hz), 7.198 (d, 1H, J=8 Hz), 6.82 (s, 1H), 4.63 (dd, 1H, J=5.5, 10.5 Hz), 4.47 (d, 1H, J=10.5 Hz), 3.175 (d, 1H, J=5.5 Hz), 2.109 (s, 3H), 1.8 (d, 2H, J=5.5 Hz)

[Entry 80]
$^1$H NMR (500.1 MHz, Acetone) ∂ 9.8 (bs, 1H), 9.3 (s, 1H), 8.5 (s, 1H), 8.2 (d, 2H, J=9.5 Hz), 8.0 (d, 1H, J=8.5 Hz), 7.9 (s, 1H), 7.85 (d, 2H, J=8.5 Hz), 7.7 (dd, 1H, J=2, 8.5 Hz), 7.4 (t, 1H, J=8 Hz), 4.8 (t, 1H, J=11.0 Hz), 4.7 (dd, 1H, J=2, 11.0 Hz), 4.24 (m, 1H) 4.05 (dd, 1H, J=3.5, 11.5 Hz), 3.85 (m, 1H), 3.25 (s, 2H), 2.5 (s, 6H).

[Entry 81]
$^1$H NMR (500.1 MHz, Acetone) ∂ 9.3 (s, 1H), 8.32 (s, 1H), 8.28 (d, 1H, J=8.5 Hz), 8.18 (s, 1H), 8.10 (s, 1H), 7.9 (dd, 3H, J=4, 9 Hz), 7.53 (t, 1H, J=7 Hz), 7.52 (m, 1H), 5.85 (bs, 1H), 4.8 (t, 1H, J=11.0 Hz), 4.68 (dd, 1H, J=2, 11.0 Hz), 4.24 (m, 1H), 4.05 (dd, 1H, J=3.5, 11.5 Hz), 3.8 (dd, 1H, J=8.5, 11.5 Hz), 3.25 (q, 2H, J=7 Hz), 1.5 (m, 2H), 1.38 (m, 2H), 0.92 (t, 3H, J=7.5 Hz)

[Entry 82]
$^1$H NMR (500.1 MHz, Acetone) ∂ 9.3 (s, 1H), 8.92 (s, 1H), 8.86 (s, 1H), 8.37 (s, 1H), 8.25 (d, 1H, J=8.5Hz), 8.20 (s, 1H), 7.94 (d, 1H, J=8.5 Hz), 7.88 (d, 1H, J=8.5 Hz), 7.618 (dd, 3H, J=5, 9 Hz), 7.542 (m, 2H), 7.4 (t, 1H, J=7 Hz), 7.043 (t, 1H, 9 Hz) 4.8 (t, 1H, J=11.0 Hz), 4.67 (d, 1H, J=11.5 Hz), 4.24 (t, 1H, J=8.5 Hz), 4.05 (dd, 1H, J=3, 11 Hz), 3.848 (dd, 1H, J=8.5, 11 Hz).

[Entry 83]
$^1$H NMR (500.1 MHz, ACETONE-d$_6$) ∂ 9.25 (s, 1H), 8.527 (s, 1H), 8.25 (d, 1H, J=8.5 Hz), 8.21 (s, 1H), 7.97 (d, 1H, J=9 Hz), 7.88 (d, 1H, J=8.5 Hz), 7.54 (t, 2H, J=8 Hz), 7.40 (t, 1H, J=8 Hz), 4.8 (t, 1H, J=11.0 Hz), 4.67 (d, 1H, J=11.0 Hz), 4.23 (m, 1H), 4.04 (dd, 1H, J=3, 11 Hz), 3.82 (dd, 1H, J=8.5, 11 Hz), (t, 2H, J=7.5 Hz), 1.7 (t, 2H, J=7.0 Hz), 1.4 (m, 4H), 0.9 (m, 3H)

[Entry 84]

$^1$H NMR (500.1 MHz, ACETONE-$d_6$) ∂ 9.6 (s, 1H), 8.44 (s, 1H), 8.238 (d, 1H, J=8.5 Hz), 8.19 (s, 1H), 7.97 (d, 1H, J=8.5 Hz), 7.87 (d, 1H, J=8.5 Hz), 7.597 (d, 1H, J=1.5 Hz), 7.53 (d, 1H, J=7 Hz), 7.4 (d, 1H, J=7.5 Hz), 7.2 (s, 1H), 4.87 (t, 1H, J=11.0 Hz), 4.65 (d, 1H, J=11.0 Hz), 4.523 (dd, 1H, J=8, 13 Hz), 4.21 (t, 1H, J=8.5 Hz), 4.03 (dd, 1H, J=3.5, 11 Hz), 3.8 (m, 1H), 3.76 (t, 1H, J=6.5 Hz), 3.183 (m, 2H), 2.08 (s, 3H), 1.99 (s, 3H), 1.51-1.44 (m, 6H)

Experimental Example

1. Cancer Cell Proliferation Inhibition Effect of Synthesized Compounds

Meanwhile, in the present Example, proliferation inhibition effect of the compound in accordance with Comparative Example 1 and the compounds corresponding to Entry 59 to Entry 72 on SK-OV-3 cancer cells were checked, and a result thereof was as shown in [Table 5].

<Experiment Method of Proliferation Inhibition Effect>

SK-OV-3 cells floated on McCoy's 5A Medium in which 10% FBS and 1% P/S were added were inoculated into a 96-Well plate at a concentration of 3×10$^4$/100 µl per Well and cultured at 37° C. for 4 hours and then, treated with 100 µl of each compound, so that a final concentration of 10 nM was attained. Then, the cells were cultured at 37° C. for 72 hours. As a control, the cells were treated with DMSO as a solvent of the compounds to attain a final concentration of 0.1%. Each well was treated with 10 µl of a WST-1 assay reagent (iTSBio, Korea), and cultured at 37° C. for 2 hours. Then, absorbance was measured with an automatic Microplate Reader at 450 nm. A cell growth inhibition level was calculated by $\{(A450_{control}-A450_{compound})/A450_{control}\}*100$.

TABLE 5

<SK-OV-3 cell proliferation inhibition effect of compound in accordance with Comparative Example 1 and selenophene-fused aromatic compounds corresponding to Entry 59 to Entry 72 (IC$_{50}$)>

| Material | Proliferation inhibition effect (10 nM; %) |
|---|---|
| Comparative Example 1 | 80 |
| Entry 59 | 74 |
| Entry 60 | 78 |
| Entry 61 | 81 |
| Entry 62 | 86 |
| Entry 63 | 78 |
| Entry 64 | 85 |
| Entry 65 | 85 |
| Entry 66 | 87 |
| Entry 67 | 78 |
| Entry 68 | 82 |
| Entry 69 | 73 |
| Entry 70 | 80 |
| Entry 71 | 73 |
| Entry 72 | 75 |

The above description of the present disclosure is provided for the purpose of illustration, and it would be understood by those skilled in the art that various changes and modifications may be made without changing technical conception and essential features of the present disclosure. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A selenophene-fused aromatic compound comprising: a compound represented by the following Chemical Formula 1:

[Chemical Formula 1]

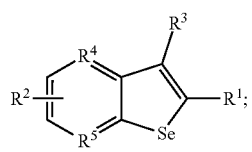

wherein R$^1$ is selected from the group consisting of —CO$_2$H, —CO$_2$R, 4-NO$_2$-Ph, 4-CN-Ph, 4-RO$_2$C-Ph, 4-X-Ph, or the following Chemical Formula A:

[Chemical Formula A]

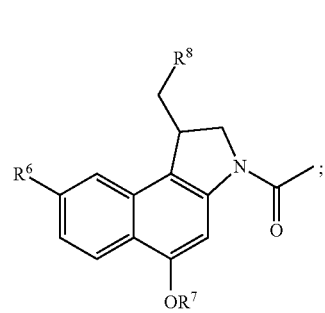

R$^2$ is selected from the group consisting of —NHCOR, —CX$_3$, —OR, -diOR, —OH, a substitutable alkylenedioxy group, a substitutable amino group, or a halo group;

X represents a halo group,

R$^3$ is selected from the group consisting of —OH, or —NH$_2$;

R$^4$ and R$^5$ are C;

R$^6$ represents H, or a substitutable alkoxy group,

R$^7$ represents H,

R$^8$ represents a halo group, and

R is selected from the group consisting of H, a substitutable alkyl group, a substitutable aryl group, a substitutable amino group, a substitutable amino acid group, a substitutable peptide group, a substitutable C$_{1-7}$ alkoxy group, or a residue of a substitutable carbohydrate or carbohydrate derivative.

2. The selenophene-fused aromatic compound of claim 1, wherein Chemical Formula 1 is selected from the following Chemical Formula:

[Chemical Formula 6]

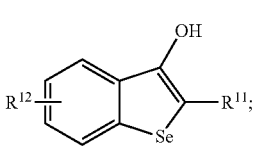

wherein in the formula, $R^{11}$ represents —$CO_2H$, —$CO_2R$, 4-$NO_2$-Ph, 4-CN-Ph, 4-$RO_2C$-Ph, or 4-X-Ph, $R^{12}$ represents —NHCOR, —$CX_3$, —OR, -diOR, —OH, a substitutable alkylene-dioxy group, a substitutable amino group, or a halo group, X represents a halo group, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

3. A selenophene-fused aromatic compound comprising:
a compound represented by the following Chemical Formula 1:

[Chemical Formula 1]

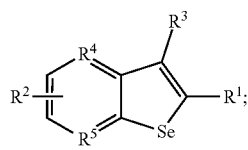

wherein $R^1$ is selected from the group consisting of —$CO_2R^a$, 4-$NO_2$-Ph, 4-CN-Ph, 4-$RO_2C$-Ph, 4-X-Ph, or the following Chemical Formula A:

[Chemical Formula A]

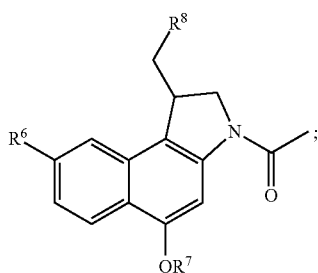

$R^2$ is selected from the group consisting of —NHCOR, —$CX_3$, —OR, -diOR, —OH, a substitutable alkylene-dioxy group, a substitutable amino group, or a halo group;

X represents a halo group, $R^3$ is selected from the group consisting of H, —OH, or —$NH_2$, $R^4$ and $R^5$ are C;

$R^6$ represents H, or a substitutable alkoxy group, $R^7$ represents H, $R^8$ represents a halo group, $R^a$ is selected from the group consisting of H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative; and, R is selected from the group consisting of H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

4. The selenophene-fused aromatic compound of claim 3, wherein Chemical Formula 1 is selected from Chemical Formulas 7 and 8:

[Chemical Formula A]

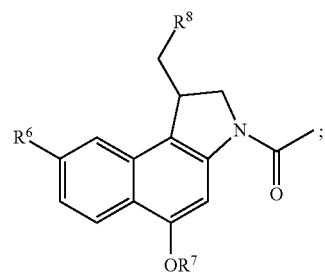

wherein in the formulas, $R^4$ and $R^5$ are C;

$R^{11}$ is selected from the group consisting of —$CO_2R^a$, 4-$NO_2$-Ph, 4-CN-Ph, 4-$RO_2C$-Ph, or 4-X-Ph, $R^{12}$ is selected from the group consisting of —NHCOR, —$CX_3$, —OR, -diOR, —OH, a substitutable alkylene-dioxy group, a substitutable amino group, or a halo group, X represents a halo group, $R^a$ is selected from the group consisting of H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative, and, R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

5. The selenophene-fused aromatic compound of claim 3, wherein Chemical Formula 1 is selected from Chemical Formulas 10 to 12:

[Chemical Formula 10]

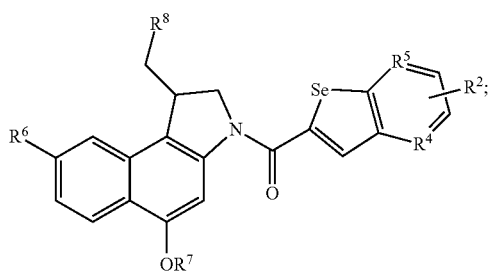

-continued

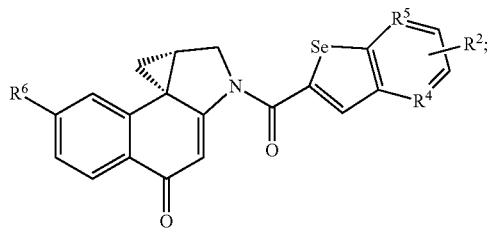

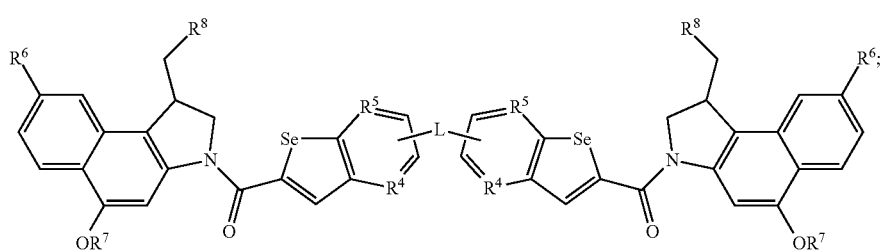

wherein in the formulas, $R^2$ is selected from the group consisting of —NHCOR, —$CX_3$, —OR, -diOR, —OH, a substitutable alkylenedioxy group, a substitutable amino group, or a halo group, $R^4$ and $R^5$ are C;

$R^6$ represents H, or a substitutable alkoxy group, $R^7$ represents H, $R^8$ represents a halo group, L represents a linker, and R represents H, a substitutable alkyl group, a substitutable aryl group, a substitutable amino group, a substitutable amino acid group, a substitutable peptide group, a substitutable $C_{1-7}$ alkoxy group, or a residue of a substitutable carbohydrate or carbohydrate derivative.

6. An anti-bacterial composition, an indicator composition, a fluorescent composition or an anticancer composition comprising a selenophene-fused aromatic compound according to claim 1.

7. A method of producing the selenophene-fused aromatic compound represented by Chemical Formula 4 of claim 2, the method comprising:

preparing a reaction mixture containing a diselenide compound represented by a general formula of $R^{11}$—$CH_2$—Se—Se—$CH_2$—$R^{11}$, a solvent, and a reducing agent; and adding an aromatic starting material represented by Chemical Formula 4a and a base to the reaction mixture to be reacted:

[Chemical Formula 4a]

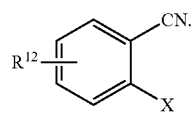

8. A method of producing the selenophene-fused aromatic compound represented by Chemical Formula 6 of claim 2, the method comprising:

preparing a reaction mixture containing a diselenide compound represented by a general formula of $R^{11}$—$CH_2$—Se—Se—$CH_2$—$R^{11}$, a solvent, and a reducing agent; and adding an aromatic starting material represented by Chemical Formula 6a and a base to the reaction mixture to be reacted:

[Chemical Formula 6a]

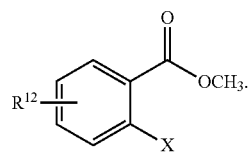

9. The method of claim 7, wherein the reducing agent contains a thiol group.

10. A producing method of producing the selenophene-fused aromatic compound represented by Chemical Formula 7 according to claim 4, the method comprising:

reacting an aromatic starting material represented by Chemical Formula 7a and $R^{11}CH_2X$ via heating to form a reaction intermediate represented by Chemical Formula 7b; and adding a solvent and a base to the reaction intermediate to be reacted:

[Chemical Formula 7a]

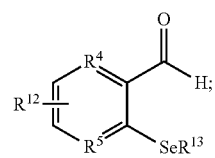

[Chemical Formula 7b]

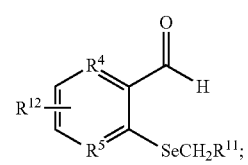

wherein $R^{13}$ represents a substitutable alkyl group.

11. A method of producing the selenophene-fused aromatic compound represented by Chemical Formula 8 of claim 4, the method comprising:

reacting an aromatic starting material represented by Chemical Formula 8a and $R^{11}CH_2X$ via heating to form a reaction intermediate represented by Chemical Formula 8b; and adding a solvent and a base to the reaction intermediate to be reacted:

[Chemical Formula 8a]

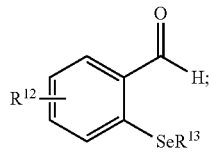

[Chemical Formula 8b]

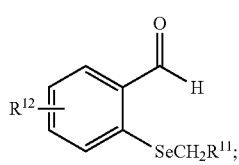

wherein in the formulas, $R^{13}$ represents a substitutable alkyl group.

12. A method of producing the selenophene-fused aromatic compound represented by Chemical Formula 10 according to claim 5, the method comprising:

reacting a MCBI (7-methoxy-1,2,9,9a-tetrahydrocyclopropa[c]benz[e]indol-4-one) compound represented by Chemical Formula 10a and a selenium-containing aromatic compound represented by Chemical Formula 10b:

[Chemical Formula 10a]

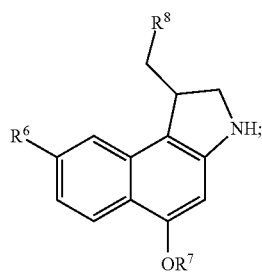

[Chemical Formula 10b]

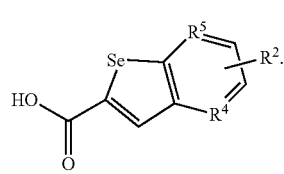

13. The method of claim 12, wherein the MCBI compound represented by Chemical Formula 10a is produced from a MCBI compound represented by Chemical Formula 10c in an acidic condition:

[Chemical Formula 10c]

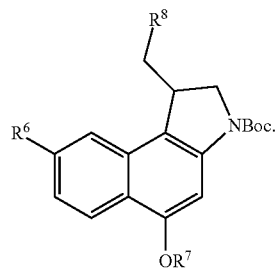

14. The method of claim 12, wherein the selenium-containing aromatic compound represented by Chemical Formula 10b is produced from a selenium-containing aromatic compound represented by Chemical Formula 10d in a basic condition:

[Chemical Formula 10d]

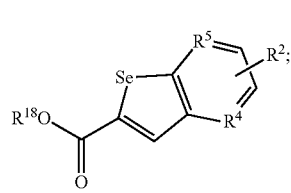

wherein $R^{18}$ represents a substitutable alkyl group, a substitutable alkoxy group, $-NO_2$, or $-NHCO_2H$.

15. A method of producing the selenophene-fused aromatic compound represented by Chemical Formula 11 according to claim 5, the method comprising:

reacting a MCBI compound represented by Chemical Formula 11a and a selenium-containing aromatic compound represented by Chemical Formula 11b:

[Chemical Formula 11a]

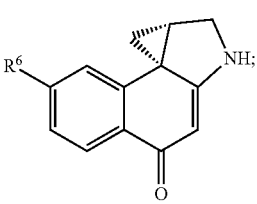

[Chemical Formula 11b]

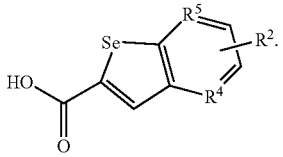

16. The method of claim 15, wherein the MCBI compound represented by Chemical Formula 11a is produced from a MCBI compound represented by Chemical Formula 11c in an acidic condition:

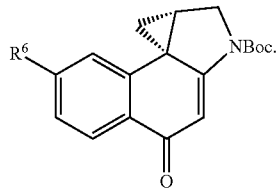
[Chemical Formula 11c]
17. The method of claim 15,
wherein the selenium-containing aromatic compound represented by Chemical Formula 11b is produced from a selenium-containing aromatic compound represented by Chemical Formula 11d in a basic condition:
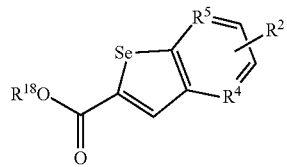
[Chemical Formula 11d]
wherein
$R^{18}$ represents a substitutable alkyl group, a substitutable alkoxy group, —$NO_2$, or —$NHCO_2H$.
* * * * *